United States Patent [19]

Havel

[11] Patent Number: 4,647,217

[45] Date of Patent: Mar. 3, 1987

[54] VARIABLE COLOR DIGITAL TIMEPIECE

[76] Inventor: Karel Havel, 15 Kensington Rd., Apt. #704, Bramalea, Ontario, Canada, L6T 3W2

[21] Appl. No.: 817,114

[22] Filed: Jan. 8, 1986

[51] Int. Cl.[4] .......................... G04B 47/00; A61B 5/02

[52] U.S. Cl. .......................... 368/10; 368/82; 128/689

[58] Field of Search .......................... 368/10, 11, 82–84, 368/223, 228, 239, 241, 242

[56] References Cited

U.S. PATENT DOCUMENTS

| | | | |
|---|---|---|---|
| 3,760,174 | 9/1973 | Boenning et al. | 240/1 R |
| 3,937,004 | 2/1976 | Natori et al. | 368/11 |
| 3,978,849 | 9/1976 | Geneen | 128/2.05 T |
| 4,044,546 | 8/1977 | Koike | 368/239 |
| 4,086,514 | 4/1978 | Havel | 313/500 |
| 4,181,134 | 1/1980 | Mason et al. | 128/690 |
| 4,451,157 | 5/1984 | Reap | 368/11 |

*Primary Examiner*—Vit W. Miska

[57] ABSTRACT

A timepiece with variable color digital display indicates time in digital format and in a color variable in accordance with the output of a transducer. In the preferred embodiment, the color of the timepiece display is controlled, either in a plurality of steps or substantially continuously, in accordance with the functioning of a heart beating within the body of a timepiece user.

11 Claims, 65 Drawing Figures

ICI CHROMATICITY DIAGRAM

| COUNT | HEART RATE PER MINUTE | COLOR |
|---|---|---|
| 128 to 191 | 39.3 to 58.6 | GREEN |
| 64 to 127 | 59.0 to 117.2 | YELLOW |
| < 63 | > 119.0 | RED |

| COUNT | HEART RATE PER MINUTE | COLOR |
|---|---|---|
| > 224 | < 33.5 | BLUE |
| 192 to 223 | 33.6 to 39.0 | PURPLE |
| 160 to 191 | 39.2 to 46.9 | BLUE-GREEN |
| 128 to 159 | 47.0 to 58.6 | GREEN |
| 96 to 127 | 59.0 to 78.1 | YELLOW |
| 64 to 95 | 79.0 to 117.0 | WHITE |
| 32 to 63 | 119.0 to 234.0 | RED |

VARIABLE COLOR DIGITAL TIMEPIECE

CROSS-REFERENCE TO RELATED APPLICATIONS

This relates to my application Ser. No. 664,426, filed on Mar. 8, 1976, entitled Electronic Timepiece with Transducer, abandoned.

BACKGROUND OF THE INVENTION

1. Field of the Invention

This invention relates to timepieces utilizing variable color digital display.

2. Description of the Prior Art

A display device that can change color and selectively display digits and characters is described in my U.S. Pat. No. 4,086,514, entitled Variable Color Display Device and issued on Apr. 25, 1978. This display device includes display areas arranged in a suitable display font, such as well known 7-segment display font, which may be selectively energized in groups to display all known characters. Each display segment includes three light emitting diodes for emitting light signals of respectively different primary colors, which are blended within the display segment to form a composite light signal. The color of the composite light signal can be controlled by selectively varying the portions of the primary light signals.

Timepieces with monochromatic digital display are well known and extensively used. Such timepieces, however, have a defect in that they are capable of indicating only values of time. They are not capable of simultaneously indicating values of time and values of another quantities.

Although the possibility of a variable color digital display has been previously considered, no practical system utilizing such a display has been made available to public use.

SUMMARY OF THE INVENTION

In a broad sense, it is the principal object of this invention to provide a timepiece with a variable color digital display.

The present invention provides a new dimension in the digital display art. Completely new, unexpected and heretofore impossible, features may be obtained when a well known monochromatic digital display is substituted with a variable color digital display. In the preferred embodiment, the invention was advantageously incorporated into a timepiece. However, the invention is not limited to timepieces and may be utilized in a wide variety of devices, without imposing any limitations.

It is another object of the invention to provide step variable 2-primary and 3-primary color control circuit which is capable of illuminating the display in a selected one of several possible colors.

It is further object of the invention to provide continuously variable 2-primary and 3-primary color converter, for converting an input voltage to variable color, which is capable of illuminating the display in any color of the spectrum, in accordance with the magnitude of the input voltage.

In summary, the electronic timepiece of the present invention is provided with a variable color digital display, in lieu of a commercially well known monochromatic digital display, to indicate time in digital format. The timepiece also includes a transducer for measuring certain physical quantities and for developing output electrical signals related to the measured physical quantities. The color of the time display is controlled in accordance with the output electrical signals of the transducer. In the most preferred embodiment, a timepiece with a variable color digital display is disclosed which can indicate time in digital format and in a color variable in accordance with the heart rate of its user.

The nature and functions of electronic timekeeping devices are well known to those having ordinary skill in the art and do not constitute a limitation on the present invention.

BRIEF DESCRIPTION OF THE DRAWINGS

In the drawings in which are shown several possible embodiments of the invention.

Throughout the drawings, like characters indicate like parts.

BRIEF DESCRIPTION OF THE TABLES

In the tables which show examples of a relationship between an input voltage, memory contents, and resulting color in the color converter of the present invention, TABLE 1 shows the characteristic of a step variable 2-primary color converter.

TABLE 2 shows a rainbow-like characteristic of a continuously variable 3-primary color converter.

Throughout the tables, memory addresses and data are expressed in a well known hexadecimal notation.

DESCRIPTION OF THE PREFERRED EMBODIMENTS

Figure 1:
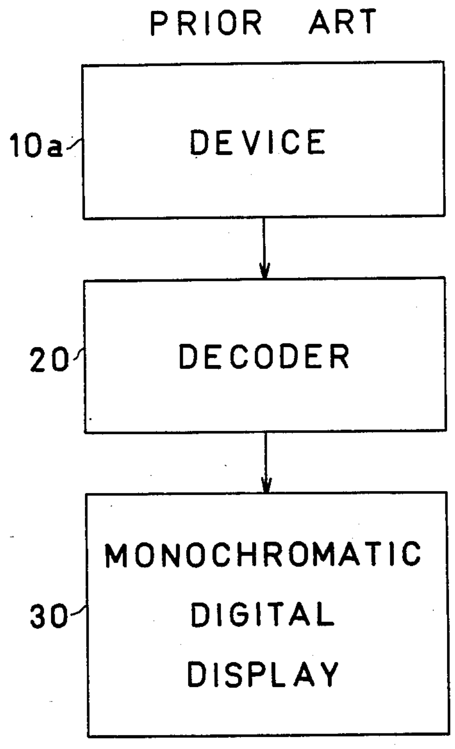
FIG. 1 is a block diagram of a typical prior art monochromatic digital display system.

Referring now, more particularly, to the drawings, in FIG. 1 is shown a block diagram of a typical prior art digital display system which usually includes a device 10a for developing digital data, a suitable decoder 20 for converting the digital data into a displayable code, and a monochromatic digital display 30 for indicating the digital data visually.

Figure 2:
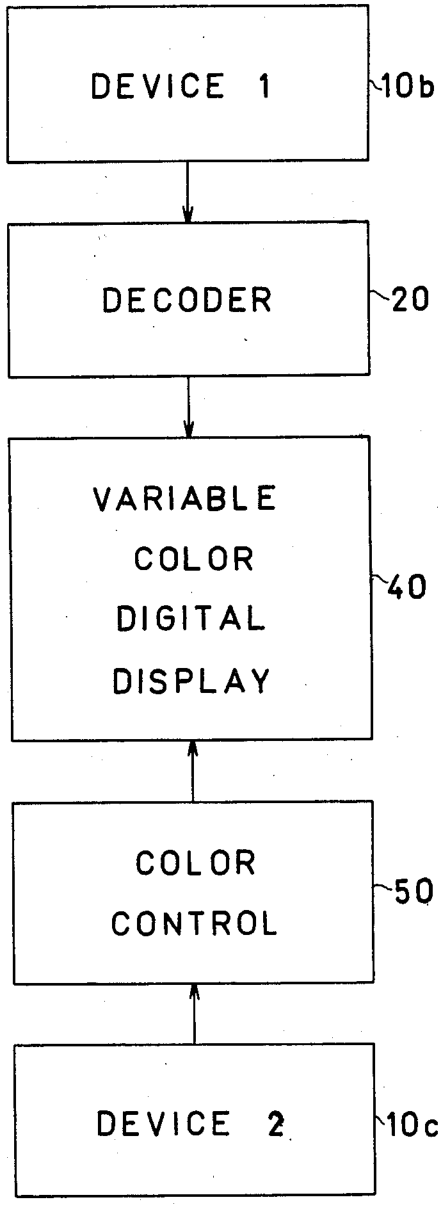
FIG. 2 is a generalized block diagram of variable color digital display system for the practice of the present invention.

As shown in FIG. 2, the present invention resides in the substitution of a commercially well known monochromatic digital display with variable color digital display 40, and in the addition of a color control circuit 50 for controlling the color of the display 40. The variable color digital display system of this invention can simultaneously indicate the values of two different quantities, from the outputs of respective devices 10b, 10c, by causing the value of the first quantity to be indicated in digital format, and by controlling the color of the display in accordance with the value of the second quantity.

Figure 3:
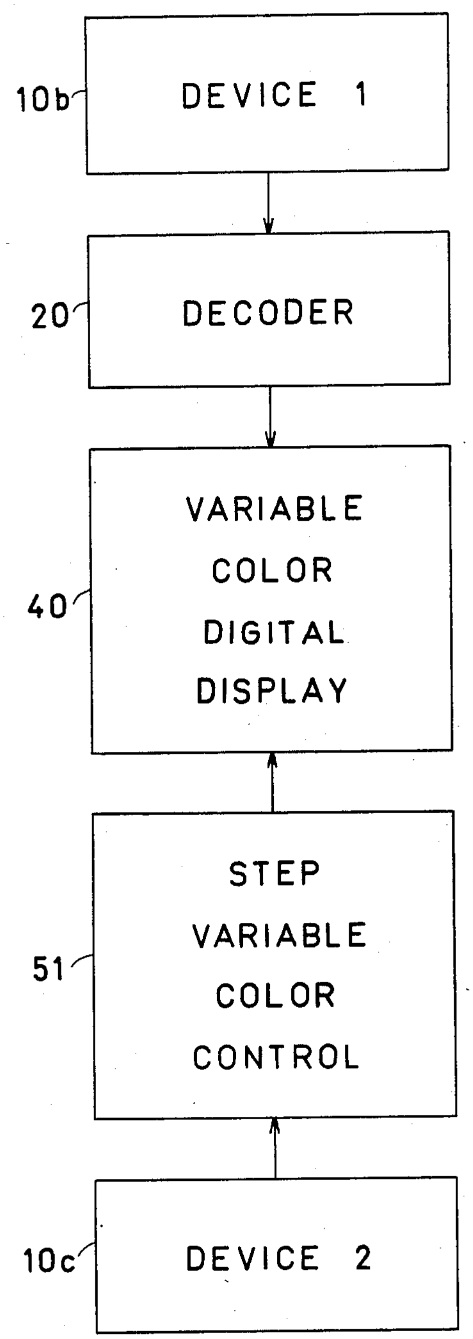
FIG. 3 is a block diagram of a step variable color display system.

In FIG. 3 is shown a block diagram of another embodiment of a variable color digital display system of the present invention, characterized by a step variable color control circuit 51.

Figure 4:
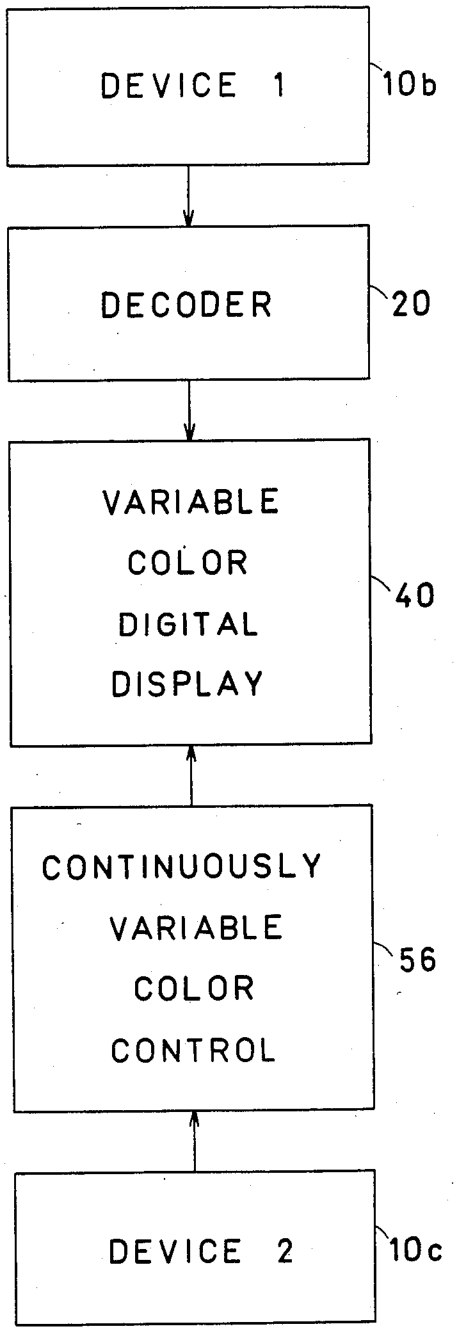
FIG. 4 is a block diagram of a continuously variable color display system.

In FIG. 4 is shown a block diagram of still another embodiment of variable color digital display system, characterized by a continuously variable color control circuit 56.

Figure 5:
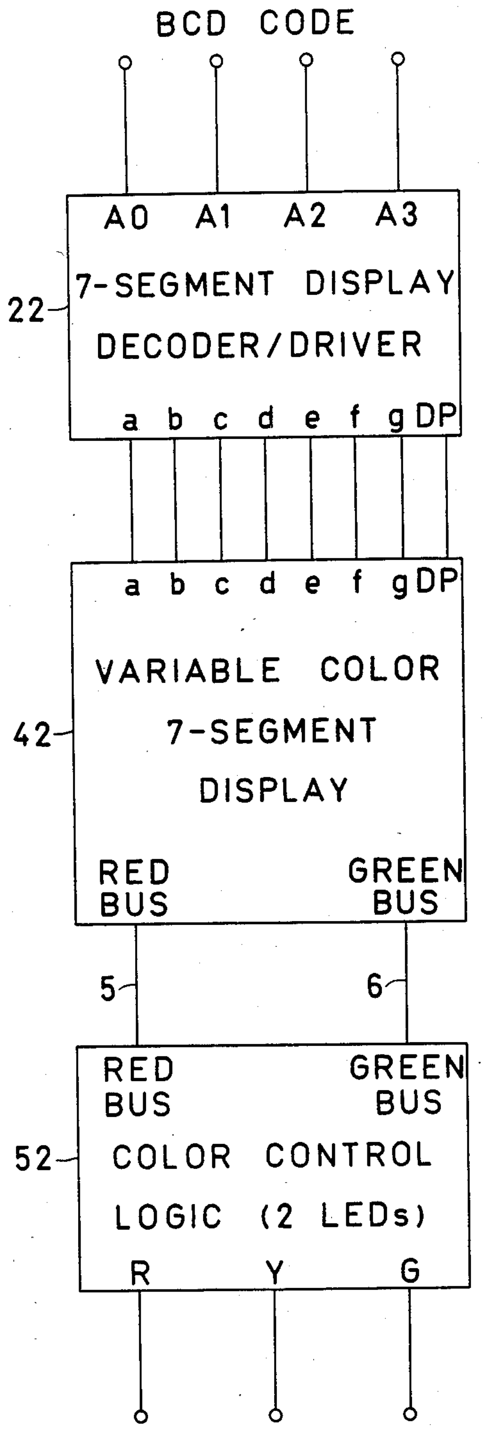
FIG. 5 is a block diagram of 2-primary color digital display.

In FIG. 5 is shown a block diagram of a 2-primary color display system including a commercially well known 7-segment display decoder driver 22, variable color 7-segment display 42, and 2-primary color control logic circuit 52. The decoder 22 accepts at its inputs A0, A1, A2, A3, a 4-bit BCD (binary coded decimal) code and develops output drive signals at its outputs a, b, c, d, e, f, g, and DP (decimal point), to drive respective segments of the 7-segment display 42. The color control circuit 52 accepts at its input R (red), Y (yellow), and G (green), color control logic signals and develops at its outputs drive signals for the red bus 5 and green bus 6, respectively, to illuminate the display 42 in a selected color.

Figure 6:
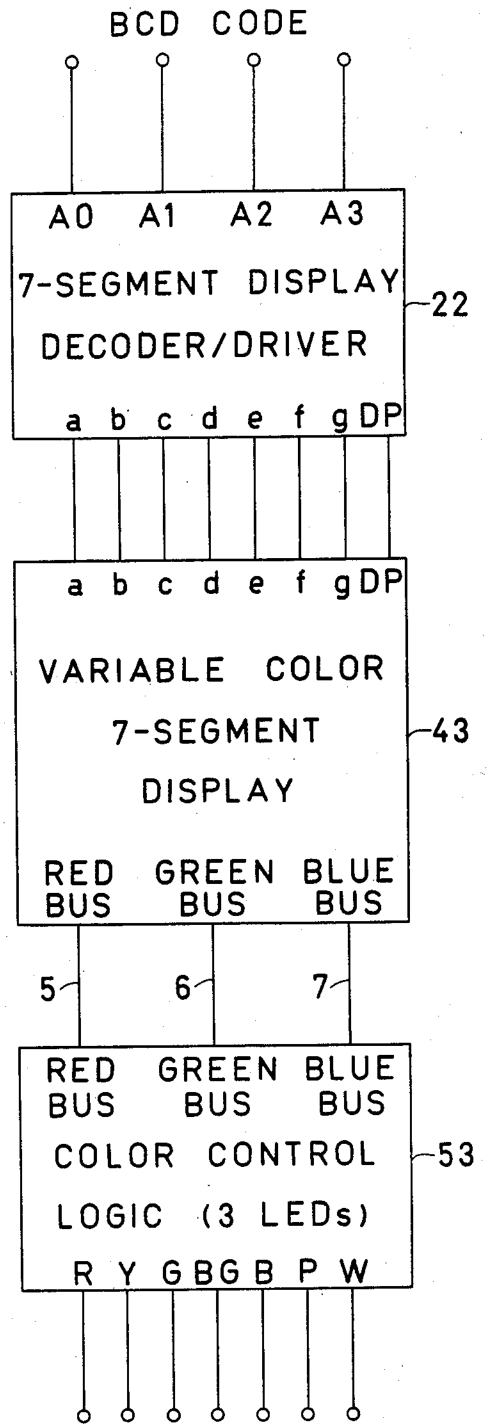
FIG. 6 is a block diagram of 3-primary color digital display.

In FIG. 6 is shown a block diagram of 3-primary color display system including a 7-segment display decoder driver 22, variable color 7-segment display 43, and 3-primary color control logic circuit 53. The color control circuit 53 accepts at its input R (red), Y (yellow), G (green), BG (blue-green), B (blue), P (purple), and W (white), color control logic signals and develops at its outputs drive signals for the red bus 5, green bus 6, and blue bus 7, respectively, to illuminate the display 43 in a selected color.

Figure 7:
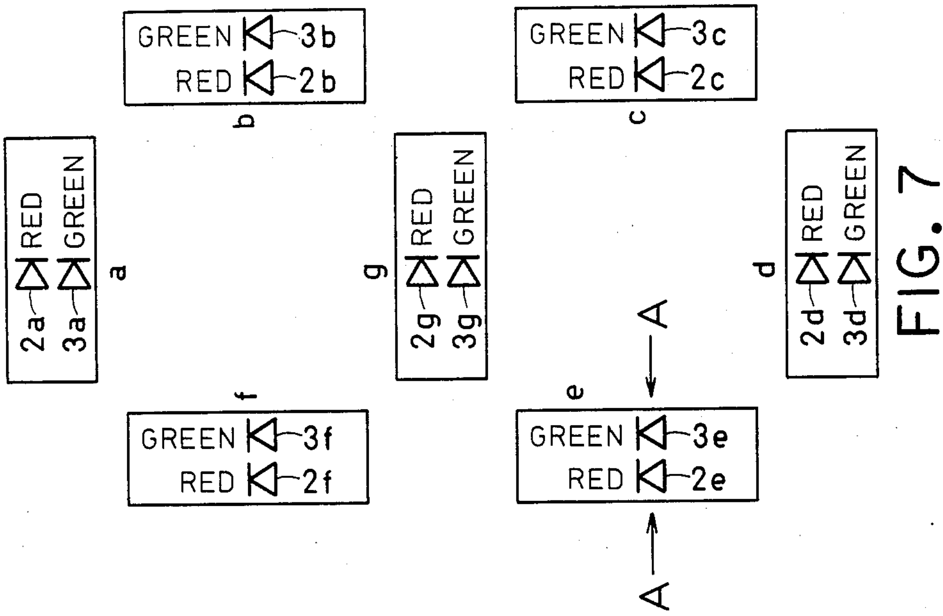
FIG. 7 is an enlarged detail of one digit of 2-primary color digital display.

In FIG. 7, the 2-primary color display element includes seven elongated display segments a, b, c, d, e, f, g, arranged in the conventional pattern, which may be selectively energized in different combinations to display the desired digits. Each display segment includes a pair of LEDs (light emitting diodes): a red LED 2 and green LED 3, which are closely adjacent such that the light signals emitted therefrom are substantially superimposed upon each other to mix the colors. To facilitate the illustration, the LEDs are designed by segment symbols, e.g., the red LED in the segment a is designated as *2a*, etc.

Figure 8:
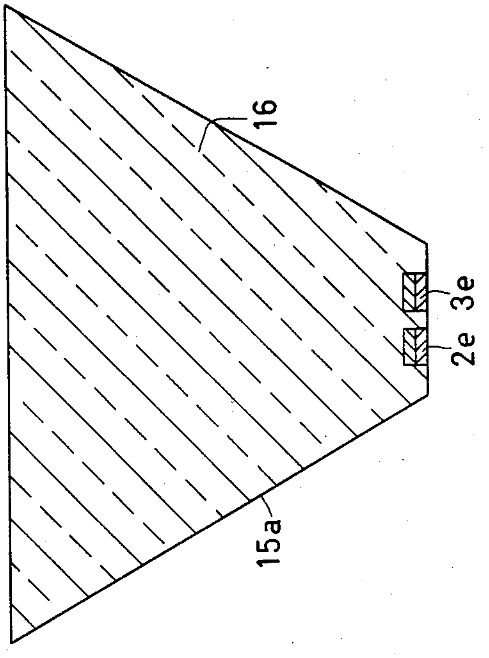
FIG. 8 is an enlarged cross-sectional view of one display segment in FIG. 7, taken along the line A—A.

In FIG. 8 the light emitting diodes *2e* (red) and *3e* (green) are placed on the base of the segment body *15a*, which is filled with transparent light scattering material 16. When forwardly biased, the LEDs *2e* and *3e* emit light signals of red and green colors, respectively, which are scattered within the transparent material 16, thereby blending the red and green light signals into a composite light signal that emerges at the upper surface of the segment body *15a*. The color of the composite light signal may be controlled by varying portions of the red and green light signals.

Figure 9:
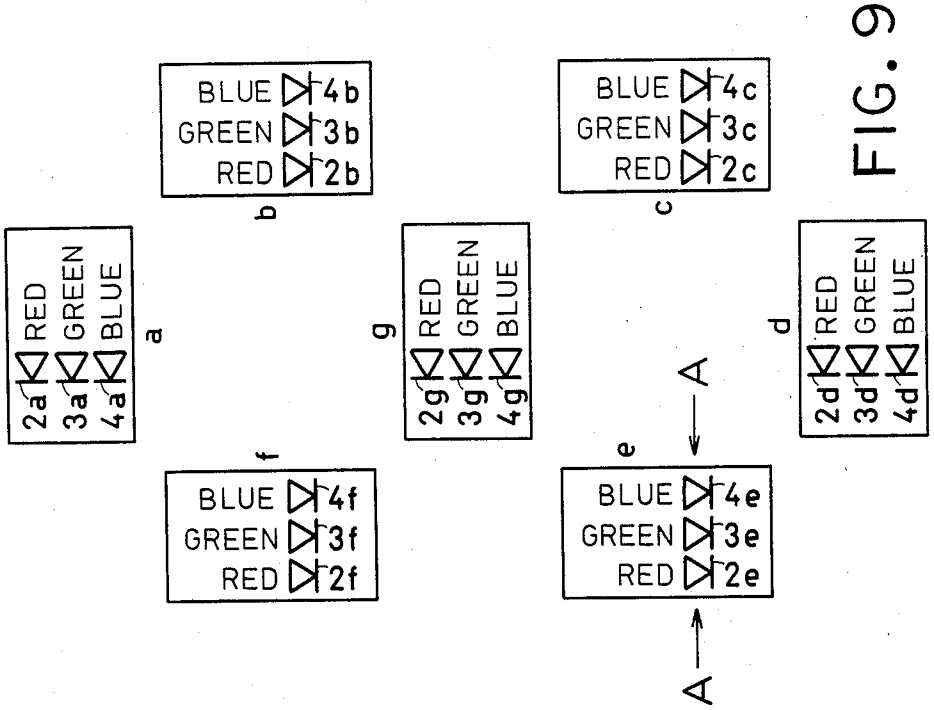
FIG. 9 is an enlarged detail of one digit of 3-primary color digital display.

In FIG. 9, each display segment of the 3-primary color display element includes a triad of LEDs: a red LED 2, green LED 3, and blue LED 4, which are closely adjacent such that the light signals emitted therefrom are substantially superimposed upon one another to mix the colors.

Figure 10:
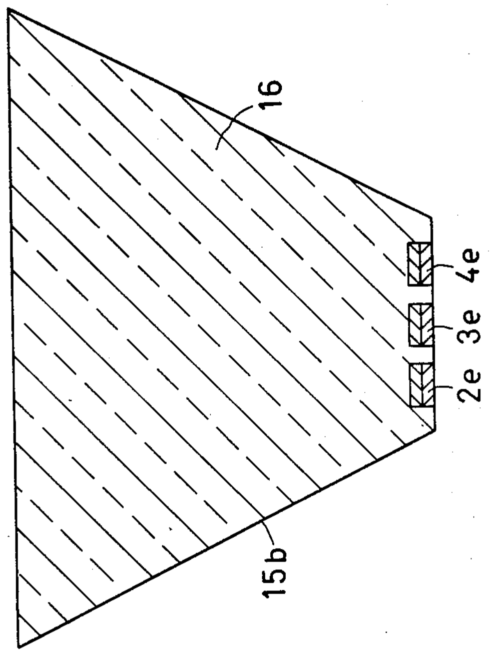
FIG. 10 is an enlarged cross-sectional view of one display segment in FIG. 9, taken along the line A—A.

In FIG. 10 the light emitting diodes *2e* (red), *3e* (green), and *4e* (blue) are placed on the base of the segment body *15b*, which is filled with transparent light scattering material 16. Red LEDs are typically manufactured by diffusing a p-n junction into a GaAsP epitaxial layer on a GaAs substrate; green LEDs typically use a GaP epitaxial layer on a GaP substrate; blue LEDs are typically made from SiC material.

When forwardly biased, the LEDs *2e*, *3e*, and *4e* emit light signals of red, green, and blue colors, respectively, which are scattered within the transparent material 16, thereby blending the red, green, and blue light signals into a composite light signal that emerges at the upper surface of the segment body *15b*. The color of the composite light signal may be controlled by varying the portions of the red, green, and blue light signals.

Figure 11:
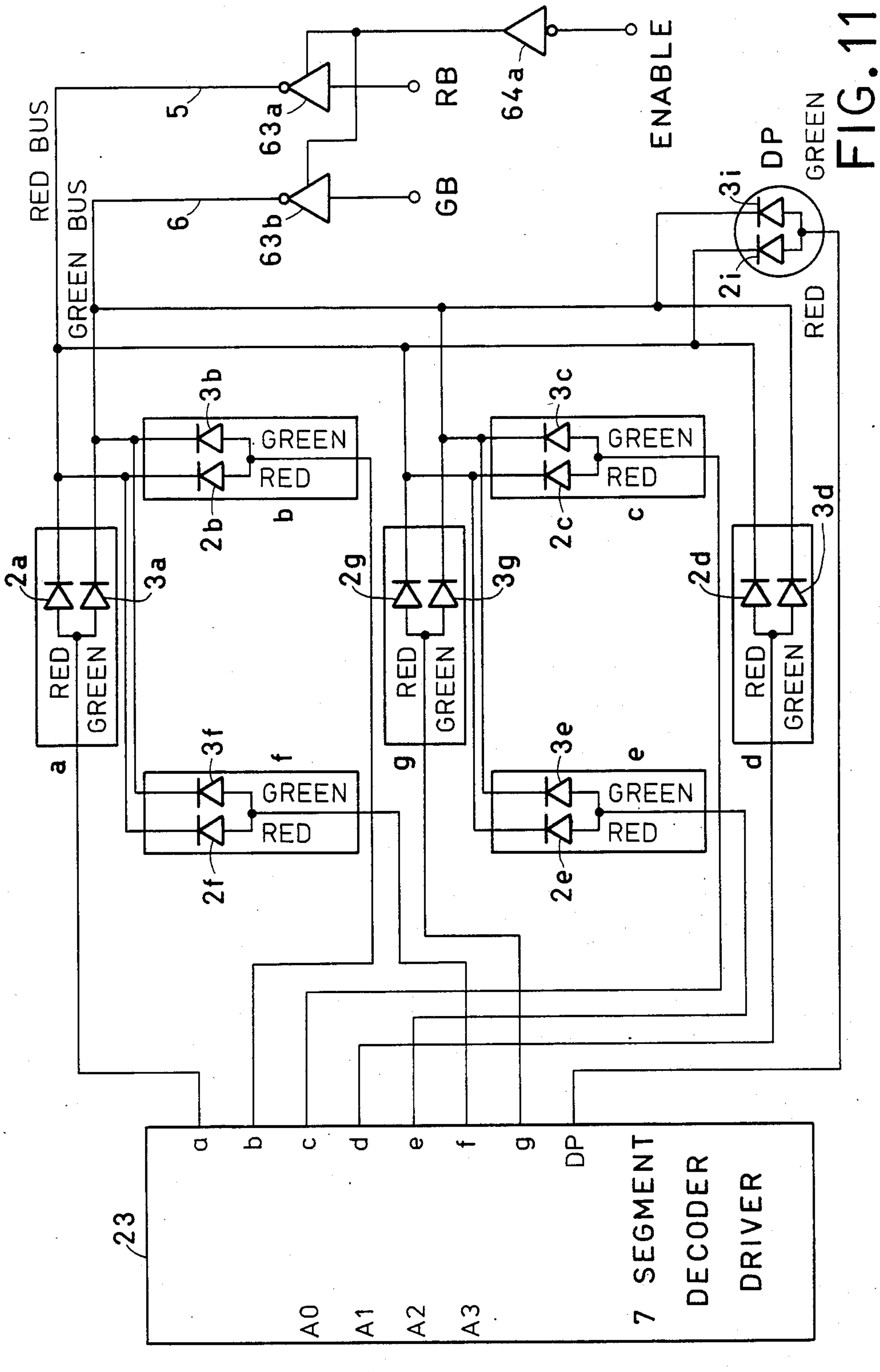
FIG. 11 is a schematic diagram of one digit of 2-primary color control circuit of this invention.

In FIG. 11 is shown a complete schematic diagram of a one-character 2-primary color common cathodes 7-segment display element which can selectively display various digital fonts in different colors. The anodes of all red and green LED pairs are interconnected in each display segment and are electrically connected to respective outputs of a commercially well known common-cathode 7-segment decoder driver 23. The cathodes of all red LEDs *2a*, *2b*, *2c*, *2d*, *2e*, *2f*, *2g*, and *2i* are interconnected to a common electric path referred to as a red bus 5. The cathodes of all green LEDs *3a*, *3b*, *3c*, *3d*, *3e*, *3f*, *3g*, and *3i* are interconnected to a like common electric path referred to as a green bus 6.

The red bus 5 is connected to the output of a tri-state inverting buffer *63a*, capable of sinking sufficient current to forwardly bias all red LEDs in the display. The green bus 6 is connected to the output of a like buffer *63b*. The two buffers *63a*, *63b* can be simultaneously enabled by applying a logic low level signal to the input of the inverter *64a*, and disabled by applying a logic high level signal therein. When the buffers *63a*, *63b* are enabled, the conditions of the red and green buses can be selectively controlled by applying suitable logic control signals to the bus control inputs RB (red bus) and GB (green bus), to illuminate the display in a selected color. When the buffers *63a*, *63b* are disabled, both red and green buses are effectively disconnected and the display is completely extinguished.

Figure 12:
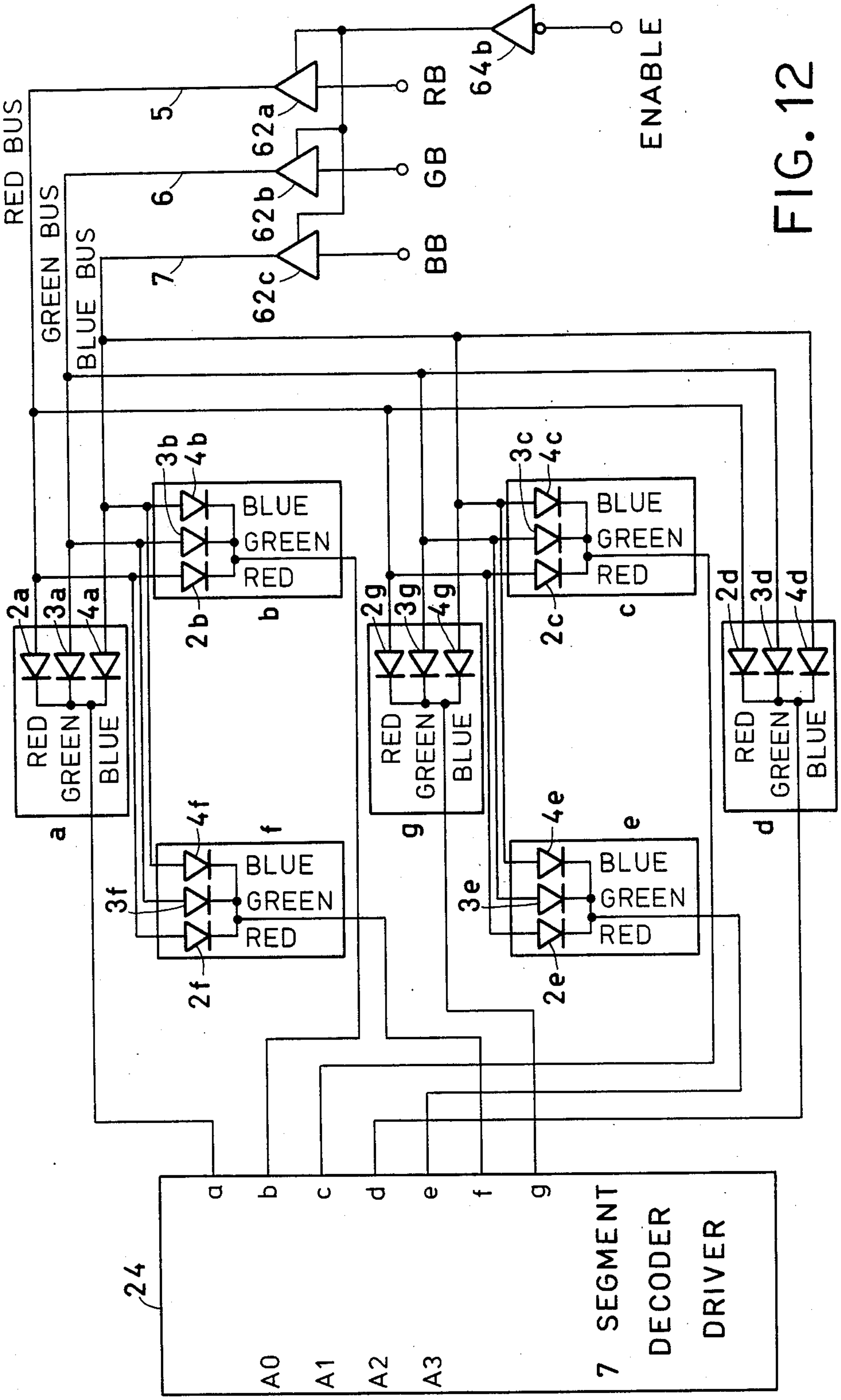
FIG. 12 is a schematic diagram of one digit of 3-primary color control circuit of this invention.

In FIG. 12 is shown a complete schematic diagram of a one-character 3-primary color common anodes 7-segment display element which can selectively display digital fonts in different colors. The cathodes of all red, green, and blue LED triads in each display segment are interconnected and electrically connected to respective outputs of a commercially well known common anode 7-segment decoder driver 24. The anodes of all red LEDs *2a*, *2b*, *2c*, *2d*, *2e*, *2f*, *2g* are interconnected to form a common electric path referred to as a red bus 5. The anodes of all green LEDs *3a*, *3b*, *3c*, *3d*, *3e*, *3f*, *3g* are interconnected to form a like common electric path to as a green bus 6. The anodes of all blue LEDs *4a*, *4b*, *4c*, *4d*, *4e*, *4f*, *4g* are interconnected to form a like common electric path referred to as a blue bus 7.

The red bus 5 is connected to the output of a non-inverting tri-state buffer *62a*, capable of sourcing sufficient current to illuminate all red LEDs in the display. The green bus 6 is connected to the output of a like buffer *62b*. The blue bus 7 is connected to the output of a like buffer *62c*. The three buffers *62a*, *62b*, *62c* can be simultaneously enabled, by applying a logic low level signal to the input of the inverter *64b*, and disabled by applying a logic high level signal therein. When the buffers *62a*, *62b*, *62c* are enabled, the conditions of the red, green, and blue buses can be selectively controlled by applying valid combinations of logic level signals to the bus control inputs RB (red bus), GB (green bus), and BB (blue bus), to illuminate the display in a selected color. When the buffers *62a*, *62b*, *62c* are disabled, all three buses are effectively disconnected and the display is completely extinguished.

STEP VARIABLE COLOR CONTROL

Figure 13:
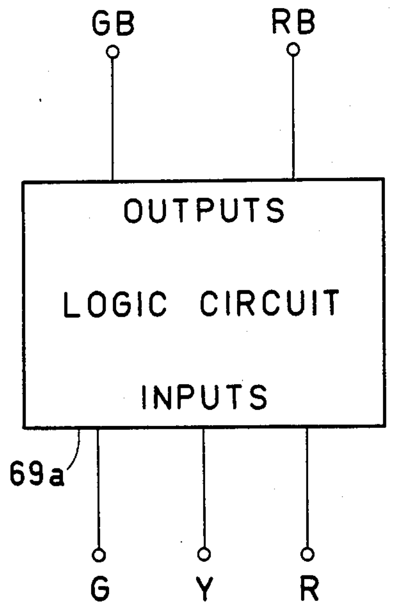
FIG. 13 is a block diagram of a color control logic circuit for controlling 2-primary color display.

In FIG. 13 is shown a logic circuit *69a* for developing drive signals for the red bus 5 and green bus 6, to control the color of the display element 42 shown in FIG.

11. Two voltage levels, referred to as logic high and low, respectively, are used throughout the description of the digital circuits. The color of the display 42 may be controlled by applying valid combinations of logic level signals to its color control inputs R (Red), Y (Yellow), and G (Green). The logic circuit 69*a* combines the input signals in a logic fashion and develops output drive signals RB (Red Bus) and GB (Green Bus), for activating the red bus 5 and green bus 6, respectively, of the display 42.

Figure 14:
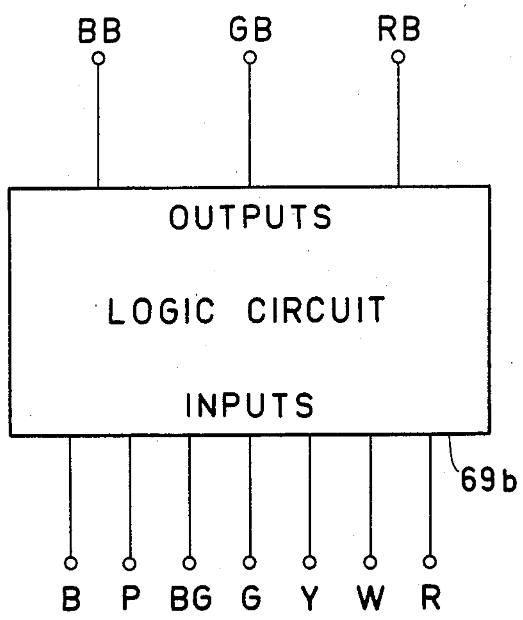
FIG. 14 is a block diagram of a color control logic circuit for controlling 3-primary color display.

In FIG. 14 is shown a like logic circuit 69*b* for developing drive signals for the red bus 5, green bus 6, and blue bus 7, to control the color of the display element 43 shown in FIG. 12. The color of the display 43 may be controlled by applying valid combinations of logic level signals to its color control inputs B (Blue), P (Purple), BG (Blue-Green), G (Green), Y (Yellow), W (White), and R (Red). The logic circuit 69*b* combines the input signals in a logic fashion and develops output drive signals RB (Red Bus), GB (Green Bus), and BB (Blue Bus), for activating the red bus 5, green bus 6, and blue bus 7, respectively, of the display 43.

Figure 15:
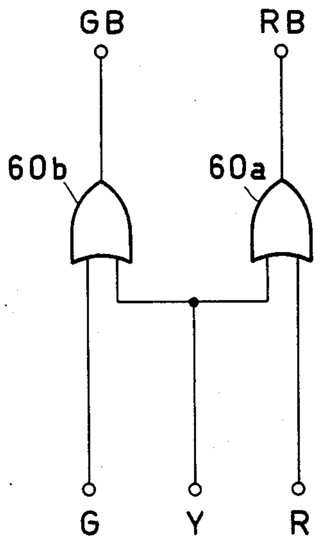
FIG. 15 is a schematic diagram of a color control logic circuit for controlling 2-primary color display.
Figure 16:
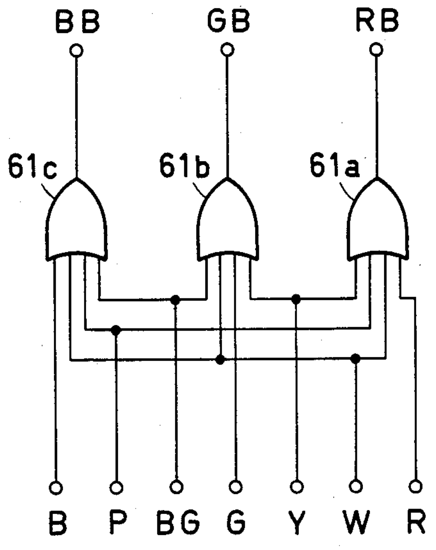
FIG. 16 is a schematic diagram of a color control logic circuit for controlling 3-primary color display.

Exemplary schematic diagrams of the clor control logic circuits shown in FIGS. 15 and 16 consider active high logic levels, which means that only the selected color control input are maintained at a high level, while all remaining color control inputs are maintained at a low logic level. The circuit in FIG. 15 is a detail of the color control logic circuit 69*a* employing 2-input logic OR gates 60*a*, 60*b*, interposed between the color control inputs R, Y, G and bus control outputs RB, GB, in a manner which will become more apparent from the description below. A like circuit in FIG. 16 is a detail of the color control logic circuit 69*b* employing 4-input logic OR gates 61*a*, 61*b*, 61*c* similarly interposed between the color control inputs B, P, BG, G, Y, W, R and bus control outputs RB, GB, BB. It will be obvious to those skilled in the art that other types of logic devices may be effectively used.

Figure 17:
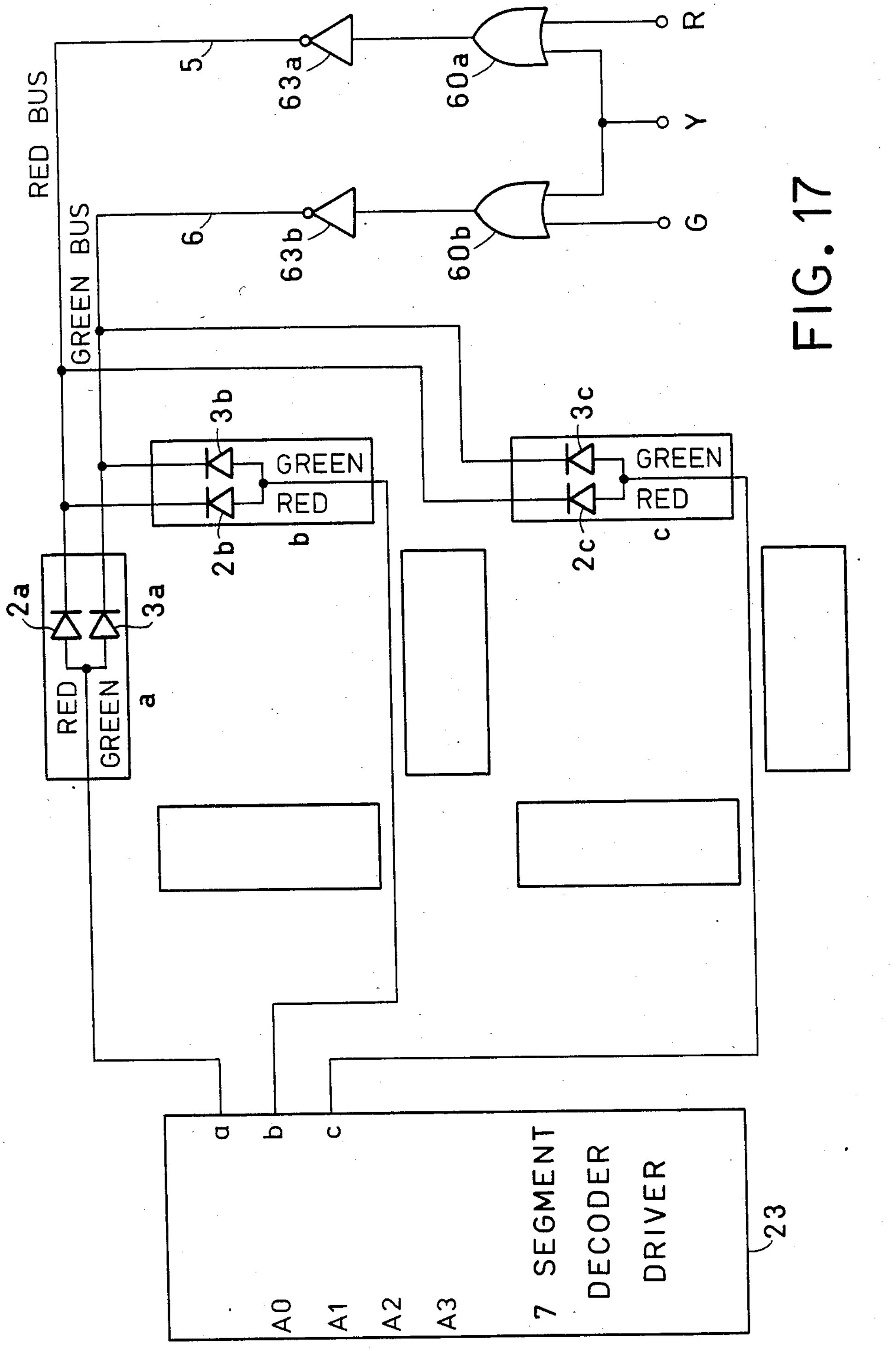
FIG. 17 is a simplified schematic diagram, similar to FIG. 11, showing how the number '7' can be displayed in three different colors.

The operation of the 2-primary color 7-segment display will be now explained in detail on example of illuminating the digit '7' in three different colors. A simplified schematic diagram to facilitate the explanation is shown in FIG. 17. Any digit between 0 and 9 can be selectively displayed by applying the appropriate BCD code to the inputs A0, A1, A2, A3 of the common-cathode 7-segment decoder driver 23. The decoder 23 will develop at its outputs a, b, c, d, e, f, g, and DP, the drive signals for energizing selected groups of the segments to thereby visually display the selected number, in a manner well known to those having ordinary skill in the art. To display decimal number '7', a BCD code 0111 is applied to the inputs A0, A1, A2, A3. The decoder 23 will develop high voltage levels at its outputs a, b, c, to illuminate the respective segments a, b, c, and low voltage levels at all remaining outputs (not shown), to extinguish all remaining segments.

To illuminate the display in red color, the color control input R is raised to a high logic level, and the color control inputs Y and G are maintained at a low logic level. As a result, the output of the OR gate 60*a* will rise to a high logic level, thereby causing the output of the buffer 63*a* to drop to a low logic level. The current will flow from the ouput a of the decoder 23, via red LED 2*a*, red bus 5, to the current sinking output of the buffer 63*a*. Similarly, the current will flow from the output b of the decoder 23, via red LED 2*b*, red bus 5, to the output of the buffer 63*a*. The current from the output c of the decoder 23 will flow via red LED 2*c*, red bus 5, to the output of the buffer 63*a*. As a result, the segments a, b, c will illuminate in red color, thereby causing a visual impression of a character '7'. The green LEDs 3*a*, 3*b*, 3*c* will remain extinguished because the output of the buffer 63*b* is at a high logic level, thereby disabling the green bus 6.

To illuminate the display in green color, the color control input G is raised to a high logic level, while the color control inputs R and Y are maintained at a low logic level. As a result, the output of the OR gate 60*b* will rise to a high logic level, thereby causing the output of the buffer 63*b* to drop to a low logic level. The current will flow from the output a of the decoder 23, via green LED 3*a*, green bus 6, to the current sinking output of the buffer 63*b*. Similarly, the current will flow from the output b of the decoder 23, via green LED 3*b*, green bus 6, to the output of the buffer 63*b*. The current from the output c of the decoder 23 will flow, via green LED 3*c*, green bus 6, to the output of the buffer 63*b*. As a result, the segments a, b, c will illuminate in green color. The red LEDs 2*a*, 2*b*, 2*c* will remain extinguished because the output of the buffer 63*a* is at a high logic level, thereby disabling the red bus 5.

To illuminate the display in yellow color, the color control input Y is raised to a high logic level, while the color inputs R and G are maintained at a low logic level. As a result, the outputs of both OR gates 61*a*, 61*b* will rise to a high logic level, thereby causing the outputs of both buffers 63*a*, 63*b* to drop to a low logic level. The current will flow from the output a of the decoder 23, via red LED 2*a*, red bus 5, to the current sinking output of the buffer 63*a*, and, via green LED 3*a*, green bus 6, to the current sinking output of the buffer 63*b*. Similarly, the current from the output b of the decoder 23 will flow, via red LED 2*b*, red bus 5, to the output of the buffer 63*a*, and, via green LED 3*b*, green bus 6, to the output of the buffer 63*b*. The current from the output c of the decoder 23 will flow, via red LED 2*c*, red bus 5, to the output of the buffer 63*a*, and, via green LED 3*c*, green bus 6, to the output of the buffer 63*b*. As a result of blending light of red and green color in each segment, the segments a, b, c will illuminate in substantially yellow color.

Figure 18:
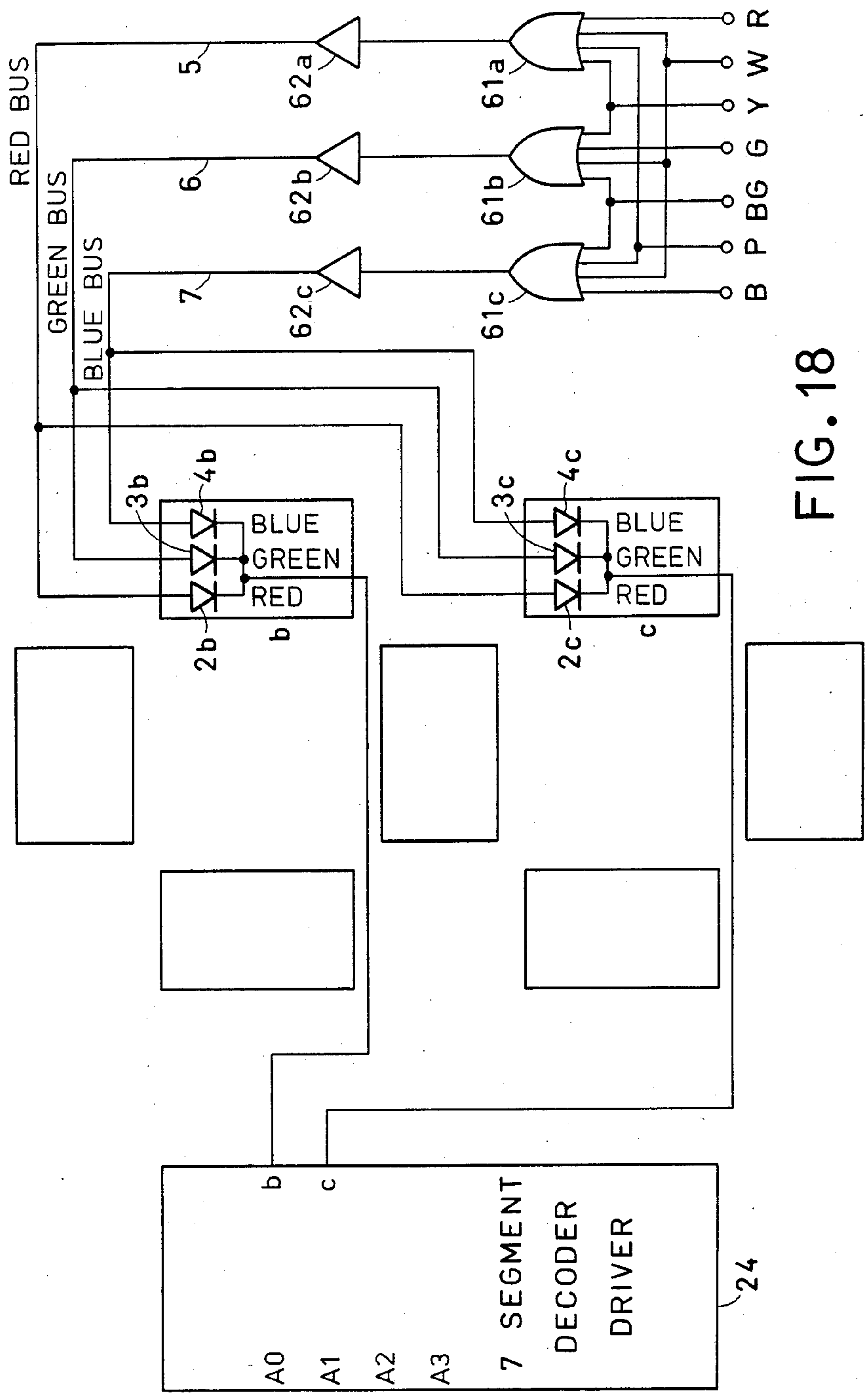
FIG. 18 is a simplified schematic diagram, similar to FIG. 12, showing how the number '1' can be displayed in seven different colors.

The operation of the 3-primary color 7-segment display shown in FIG. 12 will be now explained in detail on example of illuminating the digit '1' in seven different colors. A simplified schematic diagram to facilitate the explanation is shown in FIG. 18. To display decimal number '1', a BCD code 0001 is applied to the inputs A0, A1, A2, A3 of the common anode 7-segment decoder driver 24. The decoder 24 will develop low voltage levels at its outputs b, c to illuminate the segments b, c, and high voltage levels at all remaining outputs (not shown), to extinguish all remaining segments.

To illuminate the display in red color, the color control input R is raised to a high logic level, while all remaining color control inputs are maintained at a low logic level. As a result, the output of the OR gate 61*a* will rise to a high logic level, thereby causing the output of the buffer 62*a* to rise to a high logic level. The current will flow from the output of the buffer 62*a*, via red bus 5, red LED 2*b*, to the output b of the decoder 24, and, via red LED 2*c*, to the output c of the decoder 24. As a result, the segments b, c will illuminate in red color, thereby causing a visual impression of a character '1'. The green LEDs 3*b*, 3*c* and blue LEDs 4*b*, 4*c* will remain extinguished because the green bus 6 and blue bus 7 are disabled.

To illuminate the display in green color, the color control input G is raised to a high logic level, while all remaining color control inputs are maintained at a low logic level. As a result, the output of the OR gate 61*b* will rise to a high logic level, thereby causing the output of the buffer 62*b* to rise to a high logic level. The current will flow from the output of the buffer 62*b*, via green bus 6, green LED 3*b*, to the output b of the decoder 24, and, via green LED 3*c*, to the output c of the decoder 24. As a result, the segments b, c will illuminate in green color.

To illuminate the display in blue color, the color control input B is raised to a high logic level, while all remaining color control inputs are maintained at a low logic level. As a result, the output of the OR gate 61*c* will rise to a high logic level, thereby causing the output of the buffer 62*c* to rise to a high logic level. The current will flow from the output of the buffer 62*c*, via blue bus 7, blue LED 4*b*, to the output b of the decoder 24, and, via blue LED 4*c*, to the output c of the decoder 24. As a result, the segments b, c will illuminate in blue color.

To illuminate the display in yellow color, the color control input Y is raised to a high logic level, while all remaining color control inputs are maintained at a low logic level. As a result, the outputs of the OR gates 61*a*, 61*b* will rise to a high logic level, thereby causing the outputs of the buffers 62*a*, 62*b* to rise to a high logic level. The current will flow from the output of the buffer 62*a*, via red bus 5, red LED 2*b*, to the output b of the decoder 24, and, via red LED 2*c*, to the output c of the decoder 24. The current will also flow from the output of the buffer 62*b*, via green bus 6, green LED 3*b*, to the output b of the decoder 24, and, via green LED 3*c*, to the output c of the decoder 24. As a result of blending light of red and green colors in each segment, the segments b, c will illuminate in substantially yellow color.

To illuminate the display in purple color, the color control input P is raised to a high logic level, while all remaining color control inputs are maintained at a low logic level. As a result, the outputs of the OR gates 61*a*, 61*c* will rise to a high logic level, thereby causing the outputs of the buffers 62*a*, 62*c* to rise to a high logic level. The current will flow from the output of the buffer 62*a*, via red bus 5, red LED 2*b*, to the output b of the decoder 24, and, via red LEd 2*c*, to the output c of the decoder 24. The current will also flow from the output of the buffer 62*c*, via blue bus 7, blue LED 4*b*, to the output b of the decoder 24, and, via blue LED 4*c*, to the output c of the decoder 24. As a result of blending light of red and blue color in each segment, the segments b, c will illuminate in substantially purple color.

To illuminate the display in blue-green color, the color control input BG is raised to a high logic level, while all remaining color control inputs are maintained at a low logic level. As a result, the outputs of the OR gates 61*b*, 61*c* will rise to a high logic level, thereby causing the outputs of the buffers 62*b*, 62*c* to rise to a high logic level. The current will flow from the output of the buffer 61*b*, via green bus 6, green LED 3*b*, to the output b of the decoder 24, and, via green LED 3*c*, to the output c of the decoder 24. The current will also flow from the output of the decoder 62*c*, via blue bus 7, blue LED 4*b*, to the output b of the decoder 24, and, via blue LED 4*c*, to the output c of the decoder 24. As a result of blending light of green and blue colors in each segment, the segments b, c will illuminate in substantially blue-green color.

To illuminate the display in white color, the color control input W is raised to a high logic level, while all remaining color control inputs are maintained at a low logic level. As a result, the outputs of the OR gates 61*a*, 61*b*, 61*c* will rise to a high logic level, theeby causing the outputs of the respective buffers to rise to a high logic level. The current will flow from the output of the buffer 62*a*, via red bus 5, red LED 2*b*, to the output b of the decoder 24, and, via red LED 2*c*, to the output c of the decoder 24. The current will also flow from the output of the buffer 62*b*, via green bus 6, green LED 3*b*, to the output b of the decoder 24, and, via green LED 3*c*, to the output c of the decoder 24. The current will also flow from the output of the buffer 62*c*, via blue bus 7, blue LED 4*b*, to the output b of the decoder 24, and, via blue LED 4*c*, to the output c of the decoder 24. As a result of blending light of red, green, and blue colors in each segment, the segments b, c will illuminate in substantially white color.

Since the outputs of the 7-segment decoder 24 may be overloaded by driving a triad of LEDs in parallel in the display 43, rather than a single LED in a monochromatic display, it would be obvious to employ suitable buffers to drive respective color display segments (not shown).

Figure 19:
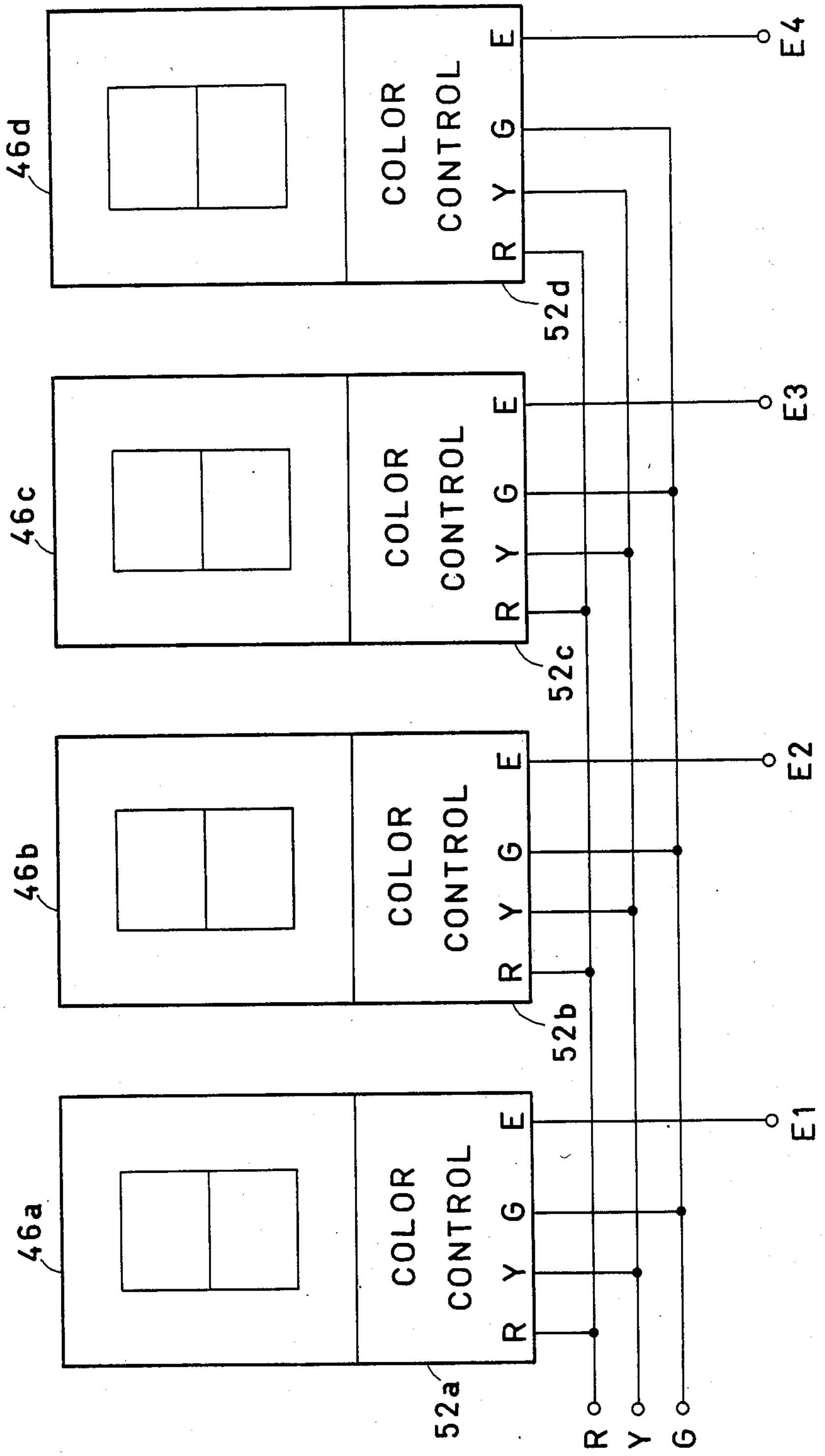
FIG. 19 is a block diagram of a multi-element 2-primary color 4-digit display.

To illustrate how the present invention can be utilized in a multi-element variable color display configuration, in FIG. 19 is shown a detail of the interconnection in a 2-primary color 4-digit display. The color control inputs R, Y, G of all display elements 46*a*, 46*b*, 46*d* are interconnected, respectively, and the enable inputs E1, E2, E3, E4 are used to control the conditions of respective display elements. A high logic level at the enable input E will extinguish the particular display element; a low logic level therein will illuminate the element in a color determined by the instant conditions of the color control logic inputs R, Y, G.

Figure 20:
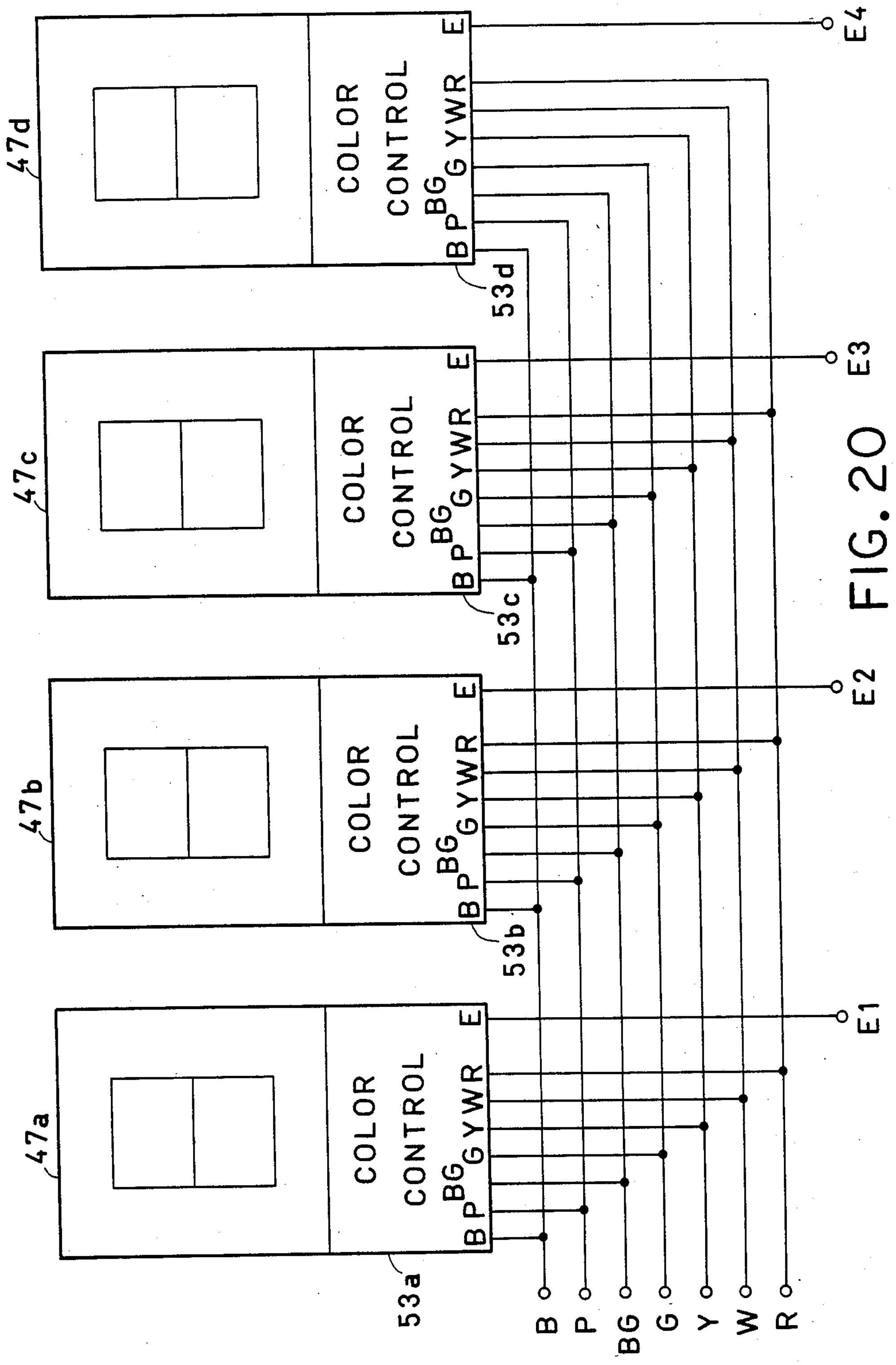
FIG. 20 is a block diagram of a multi-element 3-primary color 4-digit display.

In FIG. 20 is shown a like detail of the interconnection in a 3-primary color 4-digit display. Similarly, the color control inputs B, P, BG, G, Y, W, R of all display elements 47*a*, 47*b*, 47*c*, 47*d* are interconnected and the conditions of respective display elements are controlled by the enable inputs E1, E2, E3, E4. A high logic level at the enable input E will extinguish the particular display element; a low logic level therein will illuminate the element in a color determined by the instant conditions of the color control logic inputs B, P, BG, G, Y, W, R.

It is readily apparent that a multi-element variable color digital display may be constructed, in accordance with the principles of the invention, either in a common cathodes or in a common anodes configuration. The exemplary color control circuits described herein will cooperate equally well with both such configurations.

The enable inputs E1, E2, E3, E4 may be utilized to control the variable color multi-digit display in a multiplexed configuration, wherein the color codes for the display digits are presented in a sequence, one at a time, at a relatively fast rate, while the particular display digit is enabled.

Figure 21:
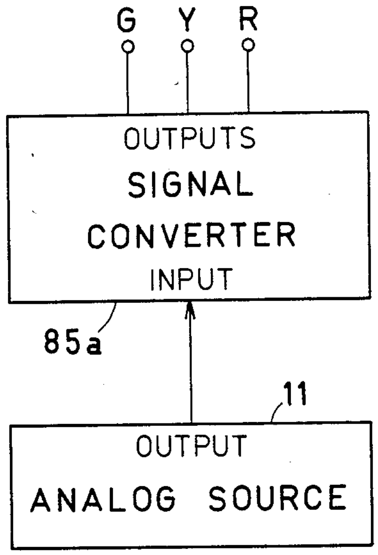
FIG. 21 is a block diagram of a signal converter for 2-primary color display.

In FIG. 21 is shown a block diagram of a signal converter for developing color control logic signals for 2-primary color display. The signal converter 85*a* accepts at its input voltage from a variable analog voltage source 11 and develops at its outputs color control logic signals R, Y, G, having relation to the magnitude of instant input analog voltage, for controlling the color of the variable color display 42, shown in FIGS. 11 and 15, in accordance with the magnitude of input voltage.

Figure 22:
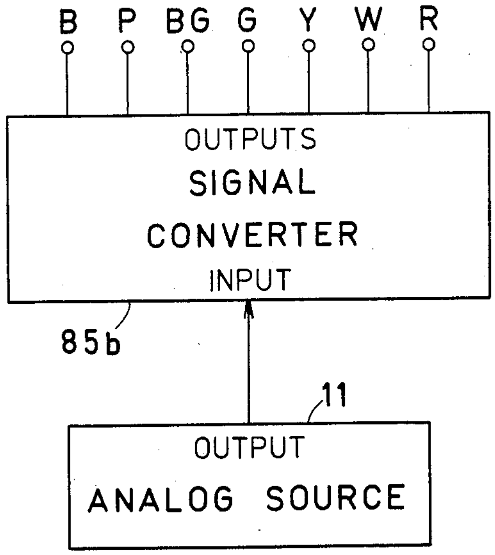
FIG. 22 is a block diagram of a signal converter for 3-primary color display.

In FIG. 22 is shown a block diagram of a like signal converter for developing color control logic signals for 3-primary color display. The signal converter 85*b* accepts at its inputs voltage from a source 11 and develops output color control logic signals B, P, BG, G, Y, W, R, related to the magnitude of instant input analog voltage, for controlling the color of the variable color display 43, shown in FIGS. 12 and 16, in accordance with the magnitude of input voltage.

Figure 23:
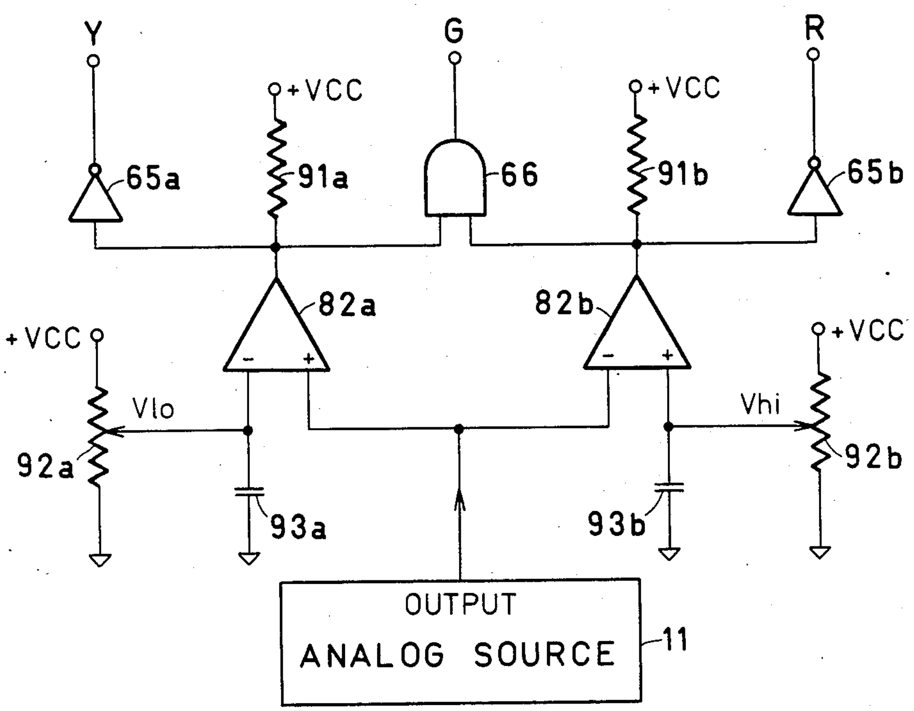
FIG. 23 is a schematic diagram of a comparator circuit for 2-primary color display.

In FIG. 23, the output voltage of a variable analog voltage source 11 is applied to the interconnected inputs of two analog comparators 82*a*, 82*b*, in a classic 'window' comparator configuration. When the voltage developed by the source 11 is lower than the low voltage limit Vlo, set by a potentiometer 92*a*, the output of the comparator 82*a* will drop to a low logic level, thereby forcing the output of the inverter 65*a* to rise to a high logic level, to activate the color control logic input Y of the display element 42, shown in FIGS. 11 and 15, to thereby illuminate the display in yellow color.

When the voltage developed by the source 11 is higher than the high voltage limit Vhi, set by a potentiometer 92*b*, the output of the comparator 82*b* will drop to a low logic level, thereby forcing the output of the inverter 65*b* to rise to a high logic level, to activate the color control logic input R, to thereby illuminate the display 42 in red color.

When the voltage developed by the source 11 is between the low voltage limit Vlo and high voltage limit Vhi, the outputs of the comparators 82*a*, 82*b* will rise to a high logic level, thereby causing the output of the AND gate 66 to rise to a high logic level, to activate the color control logic input G, to thereby illuminate the display 42 in green color.

Figure 24:
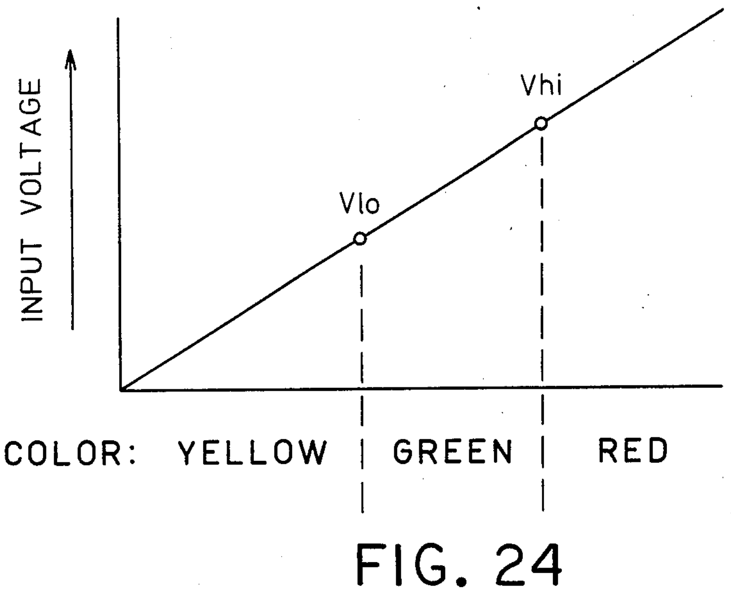
FIG. 24 is a graph showing the relationship between the inputs and outputs of the comparator circuit in FIG. 23.

FIG. 24 is a graph depicting the relationship between the input voltage of the comparator circuit shown in FIG. 23 and the color of the display element shown in FIG. 11. The display element will illuminate in yellow color for the input voltage lower than the limit Vlo, in green color for the input voltage between the limits Vlo and Vhi, and in red color for the input voltage higher than the limit Vhi.

Figure 25:
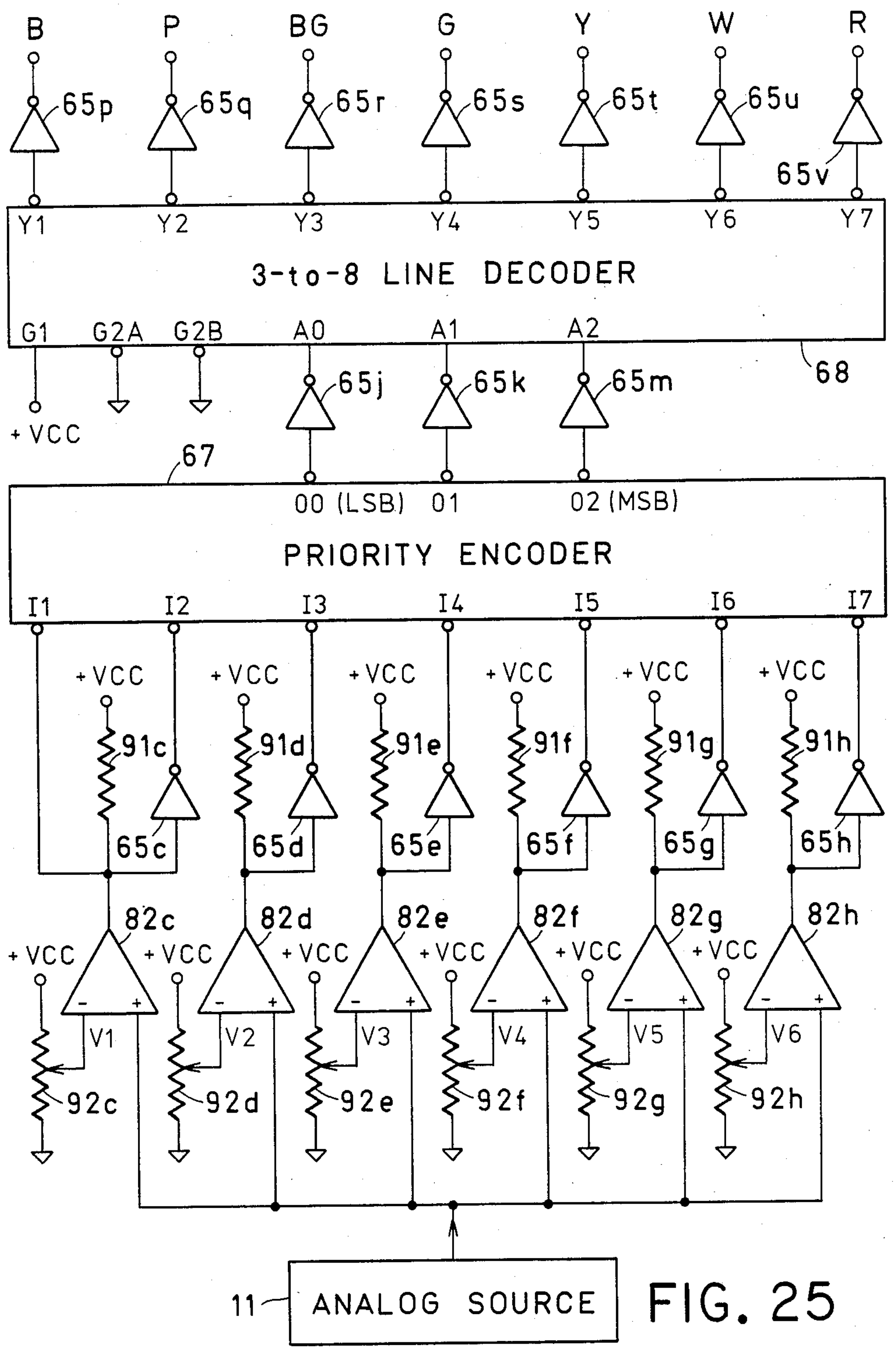
FIG. 25 is a schematic diagram of a comparator circuit for 3-primary color display.

In FIG. 25, the output voltage of a variable analog voltage source 11 is applied to the interconnected '+' inputs of six analog comparators 82*c*, 82*d*, 82*e*, 82*f*, 82*g*, 82*h*, connected in a well known 'multiple aperture window' configuration. There are six progressively increasing voltage limits V1 to V6, set by respective potentiometers 92*c* to 92*h*. The outputs of the comparators 82*c* to 82*h* are respectively connected, via inverters 65*c* to 65*h*, to the inputs I1 to I7 of a priority encoder 67. Each of the inputs I1 to I7 has assigned a certain priority (from I1 being the lowest priority progressively to I7 being the highest one). The priority encoder 67 will develop at its outputs 00, 01, 02 a code identifying the highest priority input activated. The outputs of the encoder 67 are respectively connected, via inverters 65*j* to 65*m*, to the inputs A0, A1, A2 of a 3-to-8 line decoder 68, to decode the outputs of the encoder 67 into seven mutually exclusive active logic low outputs Y1 to Y7. The outputs Y1 to Y7 are respectively connected, via inverters 65*p* to 65*v*, to the color control logic inputs B, P, BG, G, Y, W, R of the display element 43 shown in the FIGS. 12 and 16.

When the output voltage of the source 11 is lower than the lowest voltage limit V1, the output of the comparator 82*c* will drop to a low logic level, thereby activating the input I1 of the priority encoder 67. The code 110 developed at the outputs 00, 01, 02 will be inverted by the inverters 65*j* to 65*m* to yield the code 001 which will produce a low logic level at the output Y1, to force, via the inverter 65*p*, the color control logic input B to a high logic level. The display 43 will illuminate in blue color.

When the output voltage of the source 11 is between the adjacent voltage limits, e.g., V4 and V5, the output of the comparator 82*f* will rise to a high logic level, thereby activating the input I5 of the priority encoder 67. The code 100 developed at the inputs of the decoder 68 will produce a high logic level at the color control logic input Y and the display 43 will illuminate in yellow color.

Figure 26:
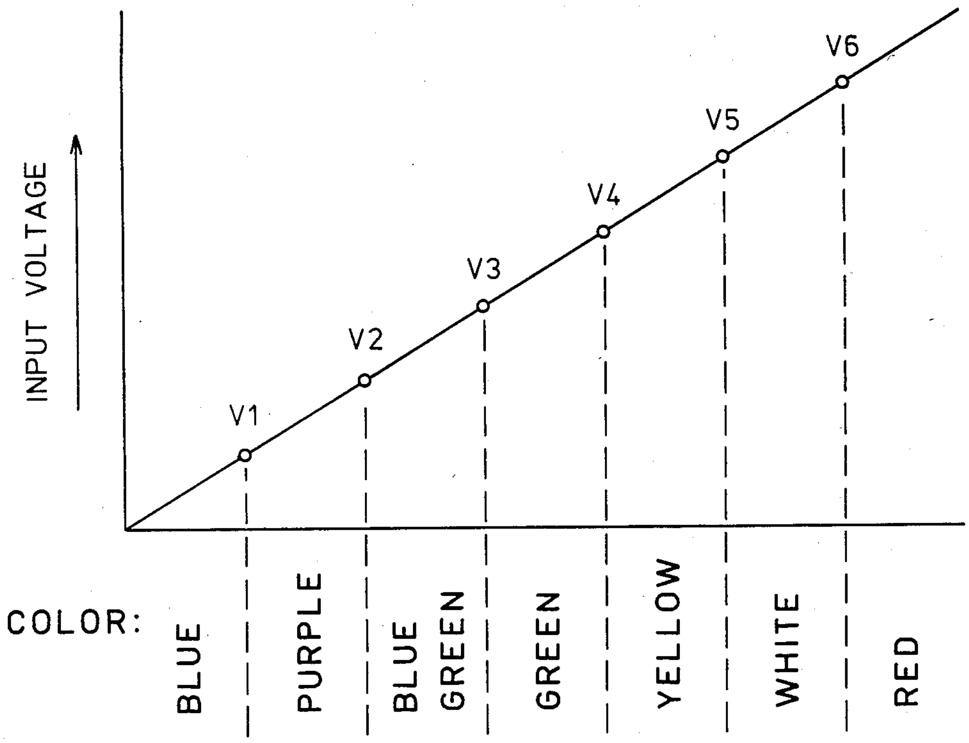
FIG. 26 is a graph showing the relationship between the inputs and outputs of the comparator circuit in FIG. 25.

FIG. 26 is a graph depicting the relationship between the input voltage of the comparator circuit shown in FIG. 25 and the color of the display element shown in FIG. 12. The display element will illuminate in blue color for the input voltage lower than the limit V1, in purple color for the input voltage between the limits V1 and V2, in blue-green color for the input voltage between the limits V2 and V3, in green color for the input voltage between the limits V3 and V4, in yellow color for the input voltage between the limits V4 and V5, in white color for the input voltage between the limits V5 and V6, and in red color for the input voltage higher than the limit V6.

It would be obvious to those having ordinary skill in the art, in the view of this disclosure, that the color sequences could be readily changed by differently interconnecting the outputs of the comparator circuit with the color control logic inputs of the display element.

CONTINUOUSLY VARIABLE COLOR CONVERTER

Figure 27:
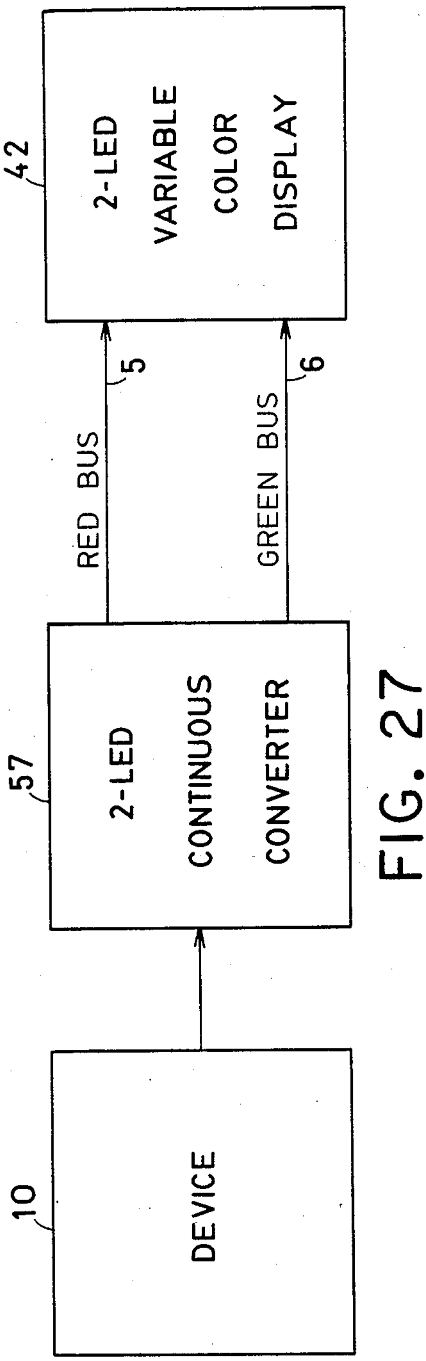
FIG. 27 is a block diagram of a continuously variable color display system utilizing two primary colors.

FIG. 27 is a block diagram of a 2-LED continuously variable color display system, which includes a device 10 for developing electric signals and 2-LED color converter circuit 57 for controlling the red bus 5 and green bus 6, respectively, of the 2-LED variable color display 42 in accordance with the electric signals.

Figure 28:
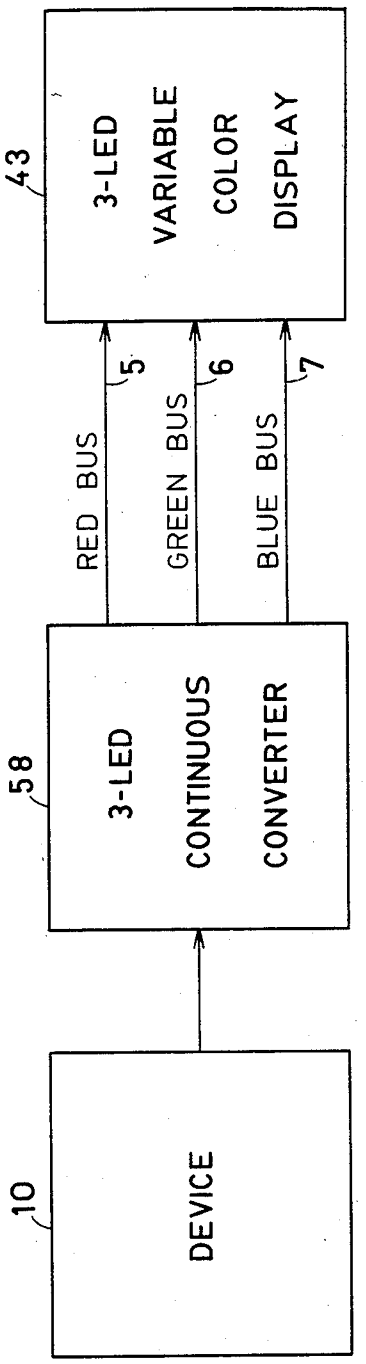
FIG. 28 is a block diagram of a continuously variable color display system utilizing three primary colors.

FIG. 28 is a block diagram of 3-LED continuously variable color display system which differs from the like system shown in FIG. 27 in that a 3-LED color converter circuit 58 is utilized to control the red bus 5, green bus 6, and blue bus 7, respectively, of the 3-LED variable color display 43, in accordance with the electric signals developed by the device 10.

Figure 29:
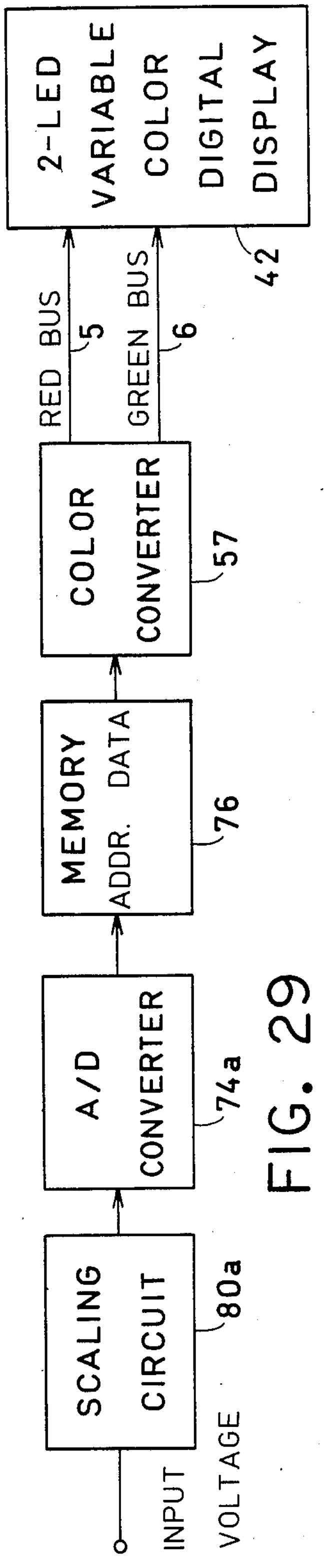
FIG. 29 is an expanded block diagram of FIG. 27.

The display system shown in FIG. 29 utilizes a scaling circuit 80*a* which scales input analog voltage levels to a voltage range suitable for an A/D converter 74*a*, which in turn develops at its outputs digital code having relation to the value of the input analog voltage. The output lines of the A/D converter 74*a* are connected to the address inputs of a memory 76 having a plurality of addressable locations which contain data indicating the portions of red color for several different values of the input analog voltage. The output data of the memory 76 are applied to the inputs of a color converter 57 which will develop control signals for the red bus 5 and green bus 6, respectively, of the variable color display 42.

Figure 30:
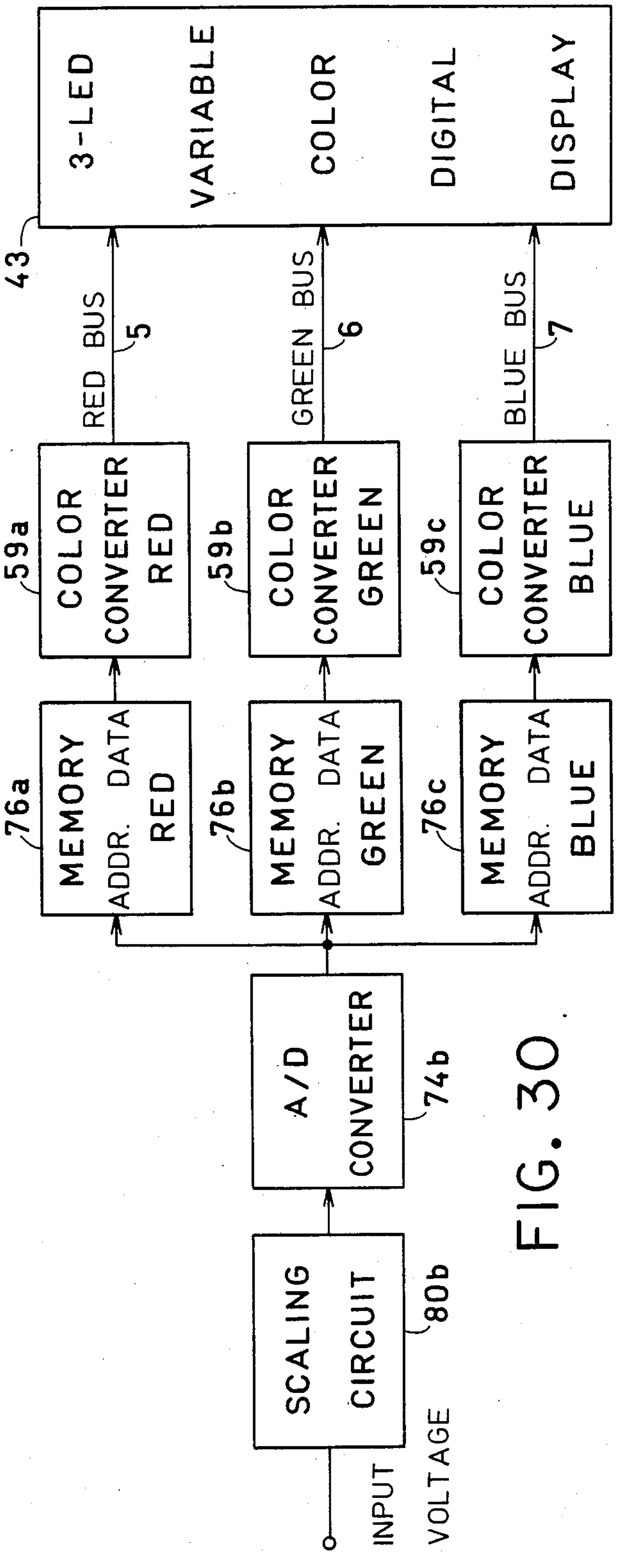
FIG. 30 is an expanded block diagram of FIG. 28.

The display system shown in FIG. 30 utilizes a scaling circuit 80*b* and an A/D converter 74*b* for converting the instant value of input analog voltage to a digital code. The outputs of the A/D converter **74*b* are connected, in parallel, to the address inputs of a memory 76*a*, which contains data indicating the portions of red color, to the address inputs of a memory 76*b*, which contains data indicating the portions of green color, and to the address inputs of a memory 76*c*, which contains data indicating the portions of blue color. The output data of the memory 76*a* are applied to the red color converter 59*a* which will develop control signals for the red bus 5 of the variable color display 43. The output data of the memory 76*b* are applied to the green color converter 59*b* which will develop control signals for the green bus 6 of the display 43. The output data of the memory 76*c* are applied to the blue color converter 59*c* which will develop control signals for the blue bus 7 of the display 43**.

Figure 31:
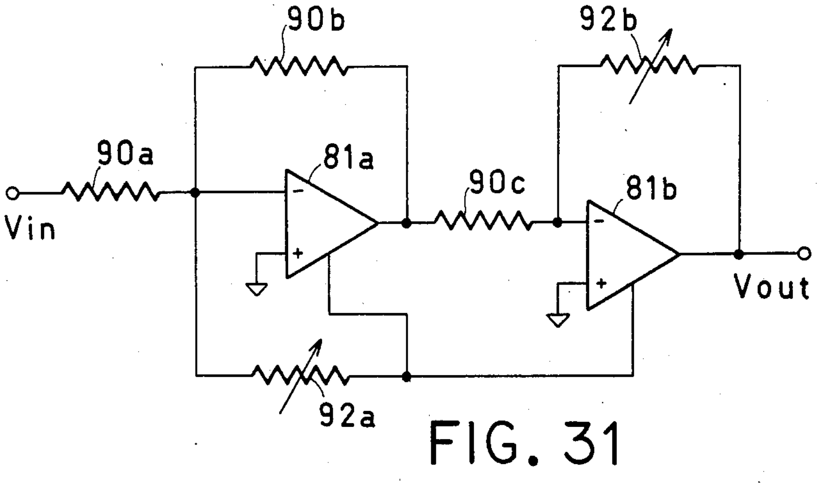
FIG. 31 is a schematic diagram of a scaling circuit.

FIG. 31 is a schematic diagram of a scaling circuit capable of shifting and amplifying the input voltage levels. The circuit utilizes two operational amplifiers **81*a*, 81*b* in a standard inverting configuration. The amplifier 81*a* is set for a unity gain, by using resistors 90*a*, 90*b* of equal values; the potentiometer 92*a* is adjusted to set a desired offset voltage. The amplifier 81*b* will set the gain, by adjusting the potentiometer 92*b***, to a desired value. As a result, the input voltage, which may vary between arbitrary limits Vlow and Vhigh, may be scaled and shifted to the range between 0 Volts and 9.961 Volts, to facilitate the use of a commercially available A/D converter.

Figure 32:
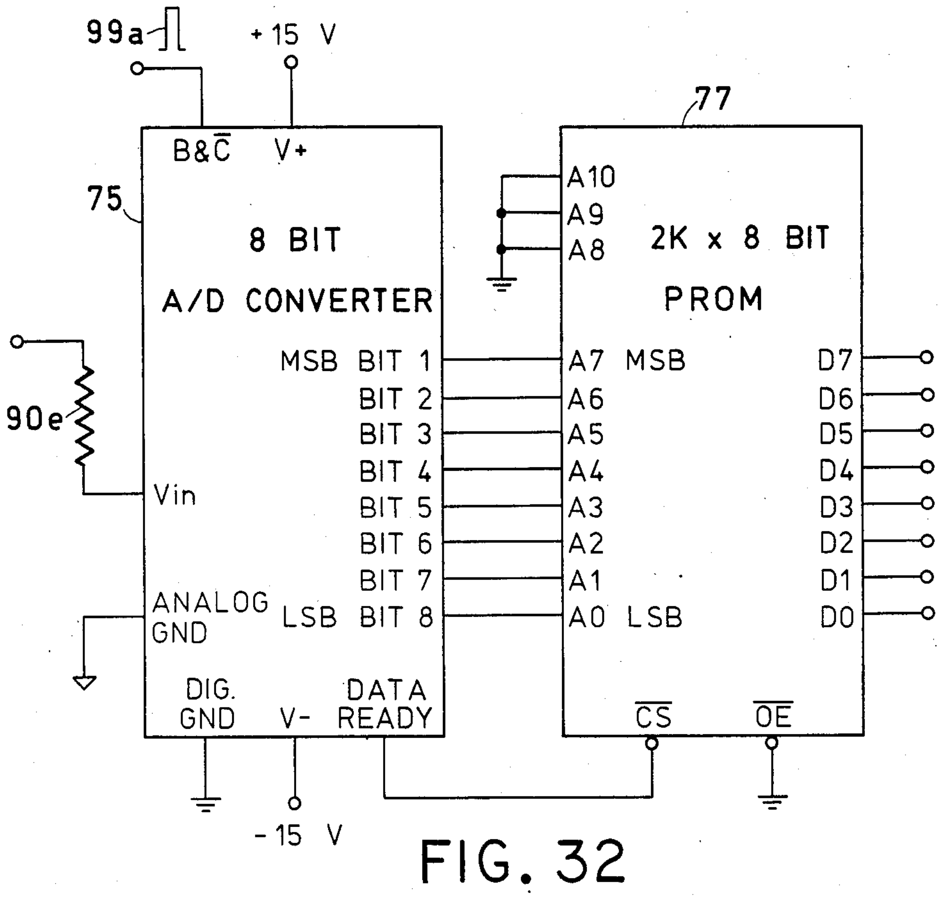
FIG. 32 is a schematic diagram of an A/D converter and memory combination of FIGS. 29 and 30.

FIG. 32 is a schematic diagram of an A/D (analog-to-digital) converter 75 which is capable of converting input analog voltage to 8-bit digital data for addressing a memory 77. The conversion may be initiated from time to time by applying a short positive pulse **99*a* to the Blank and Convert input B&C. The converter 75 will thereafter perform a conversion of the instant input voltage to 8-bit data indicative of its value. When the conversion is completed, the Data Ready output DR drops to a low logic level, thereby indicating that the data are available at the outputs Bit 1 to Bit 8, which are directly connected to respective address inputs A0 to A7 of the memory 77. When the DR output drops to a low logic level, the Chip Select input CS of the memory 77 is activated, the memory 77 is enabled, and the data, residing at the address selected by the instant output of the converter 75**, will appear at its data outputs D0 to D7.

Figure 33:
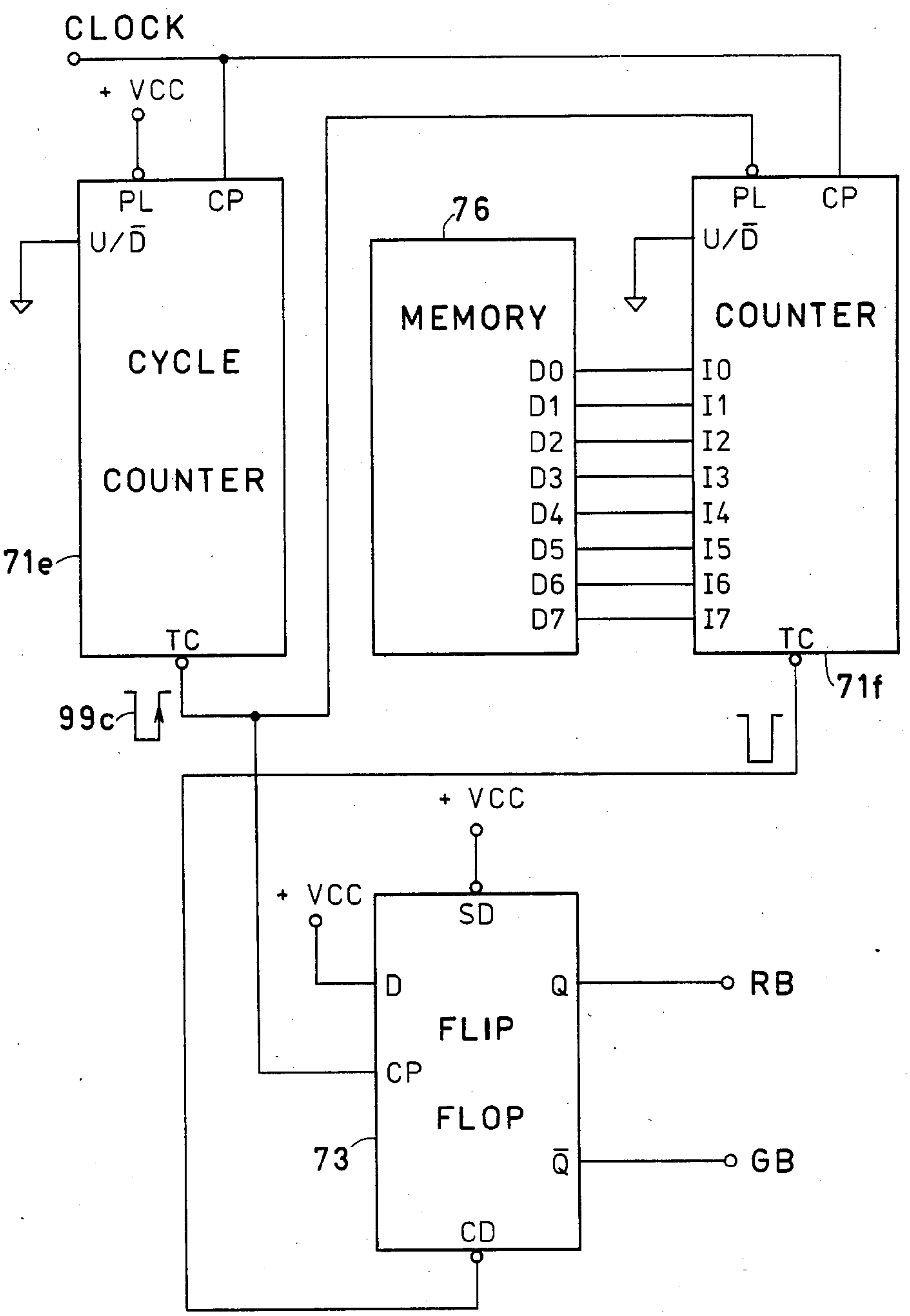
FIG. 33 is a schematic diagram of a memory and color converter combination of FIG. 29.
Figure 34:
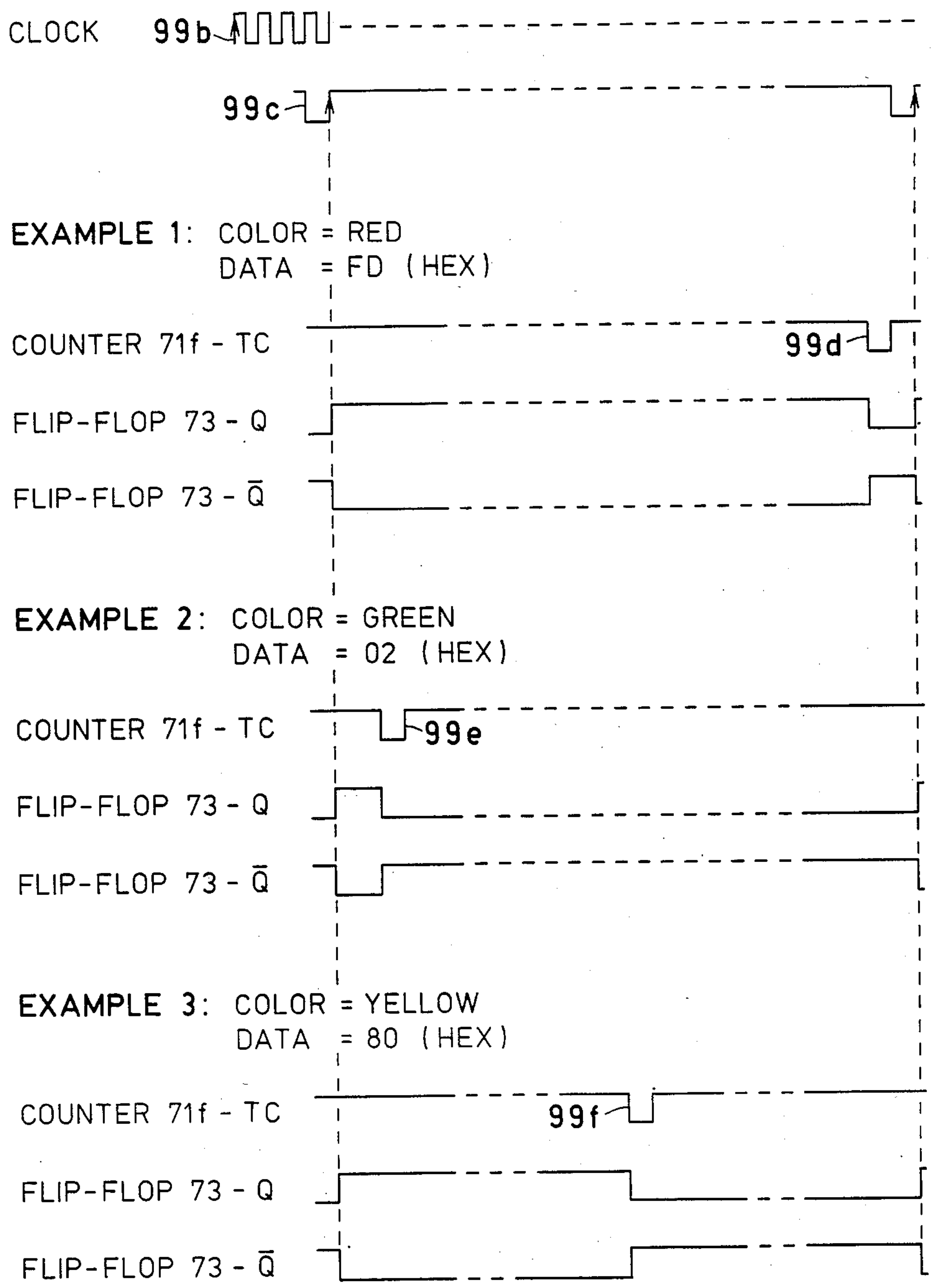
FIG. 34 is a timing diagram of the circuit shown in FIG. 33.

The description of the schematic diagram in FIG. 33 should be considered together with its accompanying timing diagram shown in FIG. 34. A clock signal **99*b* of a suitable frequency (e.g., 10 kHz), to provide a flicker-free display, is applied to the Clock Pulse inputs CP of the 8-bit binary counters 71*e*, 71*f* to step same down. At the end of each counter cycle, which takes 256 clock cycles to complete, the Terminal Count output TC of the counter 71*e* will drop to a low logic level for one clock cycle, to thereby indicate that the lowest count was reached. The negative pulse 99*c* at the TC output of the counter 71*e*, which is connected to the Parallel Load input PL of the counter 71*f*, will cause the instant data at the outputs of the memory 76 to be loaded into the counter 71*f*. The data at the memory represent the portion of the red color; the portion of the green color is complementary. The rising edge of the TC pulse 99*c* will trigger the flip-flop 73** into its set condition wherein its output Q rises to a high logic level.

The counter **71*f* will count down, from the loaded value, until it reaches zero count, at which moment its TC output will drop to a low logic level. The negative pulse at the TC output of the counter 71*f*, which is connected to the Clear Direct input CD of the flip-flop 73, will cause the latter to be reset and to remain in its reset condition until it is set again at the beginning of the next 256-count cycle. It is thus obvious that the Q output of the flip-flop 73 will be at a high logic level for a period of time proportional to the data initially loaded into the counter 71*f***. The complementary output $\overline{Q}$ will be at a high logic level for a complementary period of time.

The Q and $\overline{Q}$ outputs of the flip-flop 73 are connected to the red bus 5 and green bus 6, respectively, via suitable buffers **63*a*, 63*b*, shown in detail in FIG. 11, to energize the respective buses for variable time periods, depending on the data stored in the memory 76**.

By referring now, more particularly, to the timing diagram shown in FIG. 34, in which the waveforms are compressed to facilitate the illustration, the EXAMPLE 1 considers the memory data 'FD', in a standard hexadecimal notation, to generate light of substantially red color. At the beginning of the counter cycle, the pulse **99*c* loads the data 'FD' into the counter 71*f*. Simultaneously, the flip-flop 73 is set by the rising edge of the pulse 99*c*. The counter 71*f* will be thereafter stepped down, by clock pulses 99*b*, until it reaches zero count, 2 clock cycles before the end of the counter cycle. At that instant a short negative pulse 99*d* will be produced at its output TC to reset the flip-flop 73, which will remain reset for 2 clock cycles and will be set again by the pulse 99*c* at the beginning of the next counter cycle, which will repeat the process. It is readily apparent that the flip-flop 73 was set for 254 clock cycles, or about 99% of the time, and reset for 2 clock cycles, or about 1% of the time. Accordingly, the red bus 5 of the display 42 will be energized for about 99% of the time, and the green bus 6 will be energized for the remaining about 1% of the time. As a result, the display 42** will illuminate in substantially red color.

The EXAMPLE 2 considers the memory data '02' (HEX) to generate light of substantially green color. At the beginning of the counter cycle, the data '02' is loaded into the counter **71*f*, and, simultaneously, the flip-flop 73 will be set. The counter 71*f* will count down and will reach zero count after 2 clock cycles. At that instant it will produce at its output TC a negative pulse 99*e* to reset the flip-flop 73. It is readily apparent that the flip-flop 73 was set for 2 clock cycles, or about 1% of the time, and reset for 254 clock cycles, or about 99% of the time. Accordingly, the red bus 5 of the display 42 will be energized for about 1% of the time, and the green bus 6 will be energized for the remaining about 99% of the time. As a result, the display 42** will illuminate in substantially green color.

The EXAMPLE 3 considers the memory data '80' (HEX) to generate light of substantially yellow color. At the beginning of the counter cycle, the data '80' are loaded into the counter **71*f*, and, simultaneously, the flip-flop 73 is set. The counter 71*f* will count down, and will reach zero count after 128 clock cycles. At that instant it will produce at its output TC a negative pulse 99*f* to reset the flip-flop 73. It is readily apparent that the flip-flop 73 was set for 128 clock cycles, or about 50% of the time, and reset for 128 clock cycles, or about 50% of the time. Accordingly, the red bus 5 of the display 42 will be energized for about 50% of the time, and the green bus 6** will be energized for the remaining about 50% of the time. As a result of blending substantially equal portions of red and green colors, the display 42 will illuminate in substantially yellow color.

Figure 35:
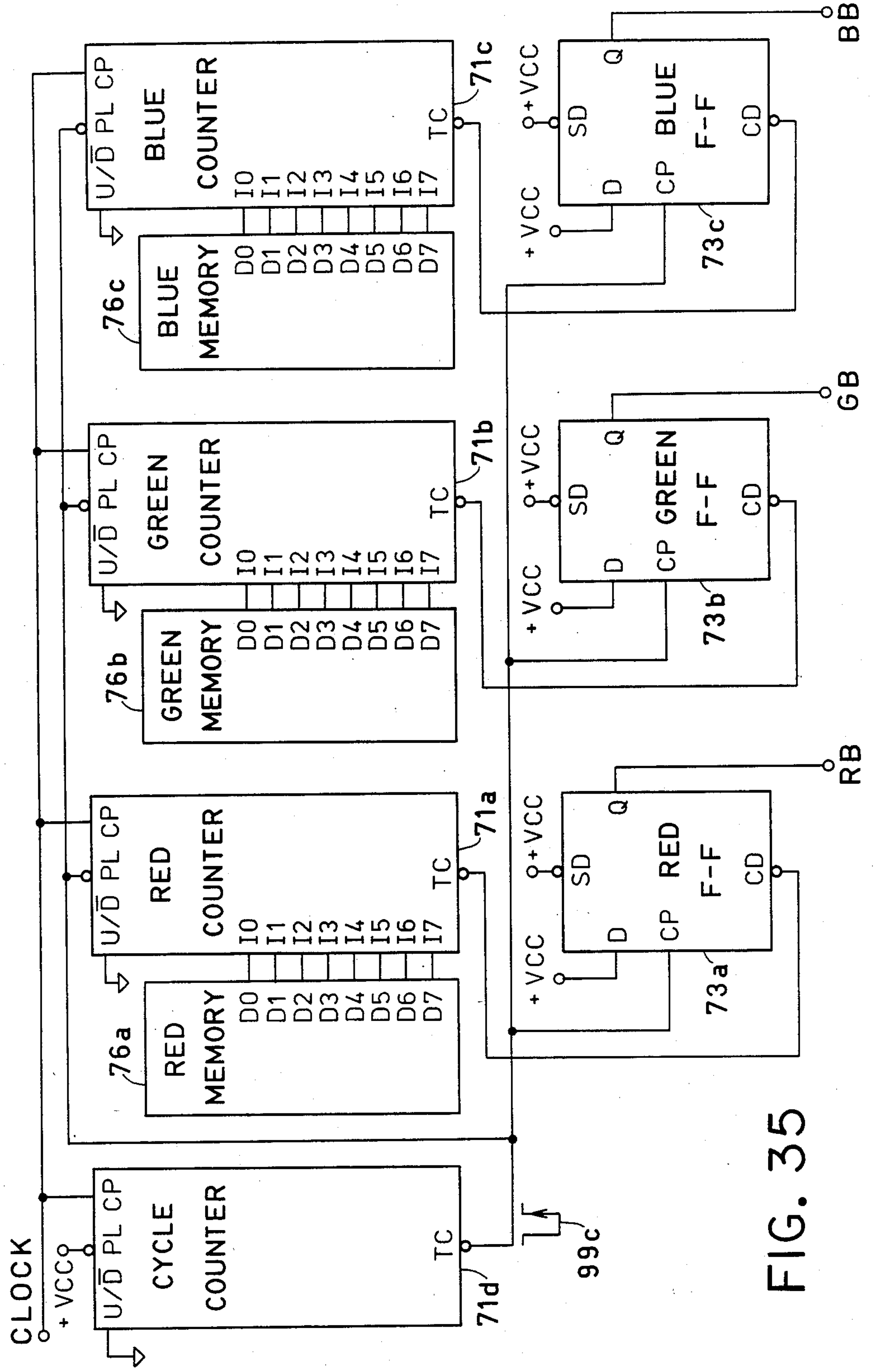
FIG. 35 is a schematic diagram of a memory and color converter combination of FIG. 30.
Figure 36:
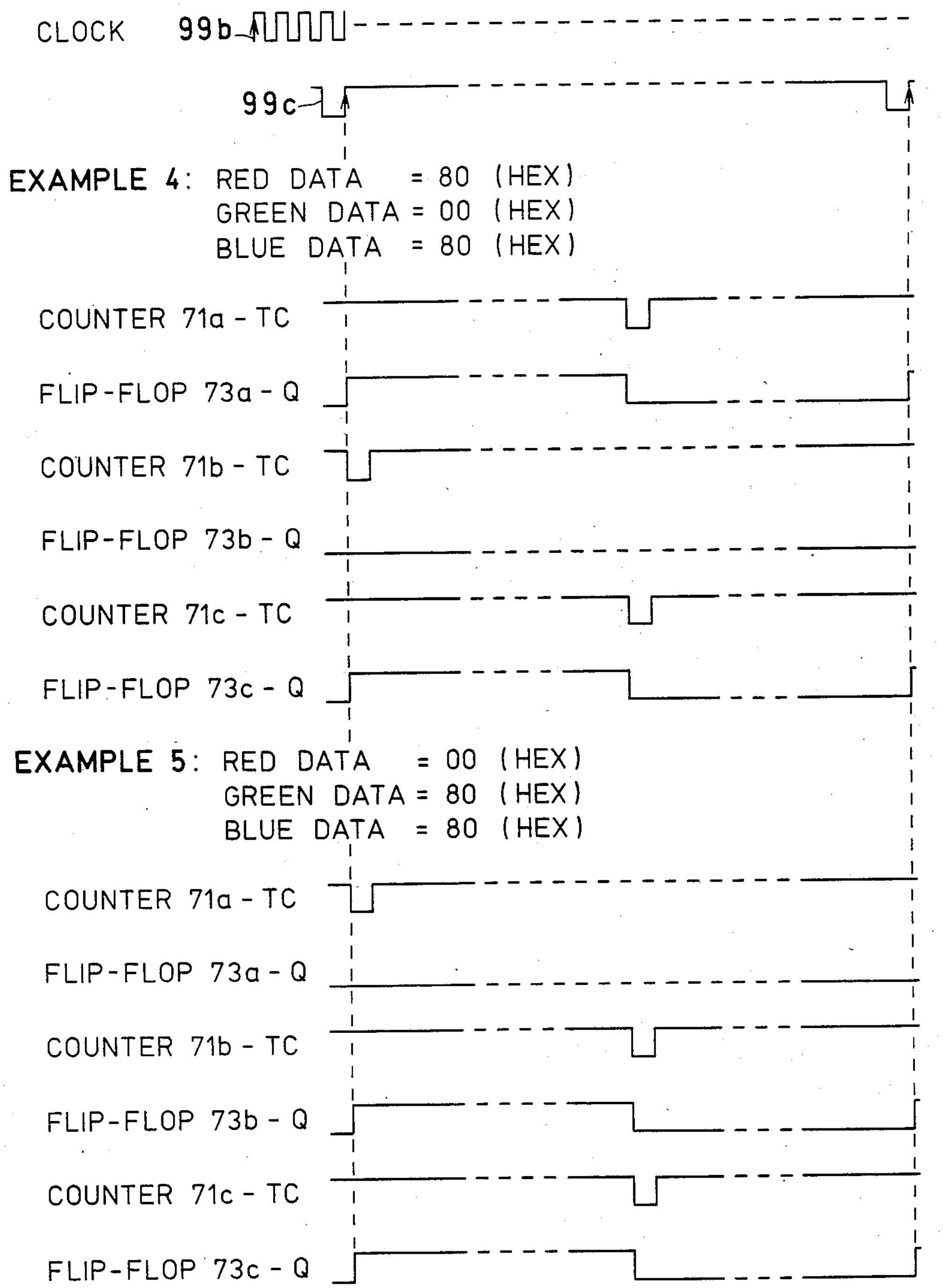
FIG. 36 is a timing diagram of the circuit shown in FIG. 35.
Figure 37:
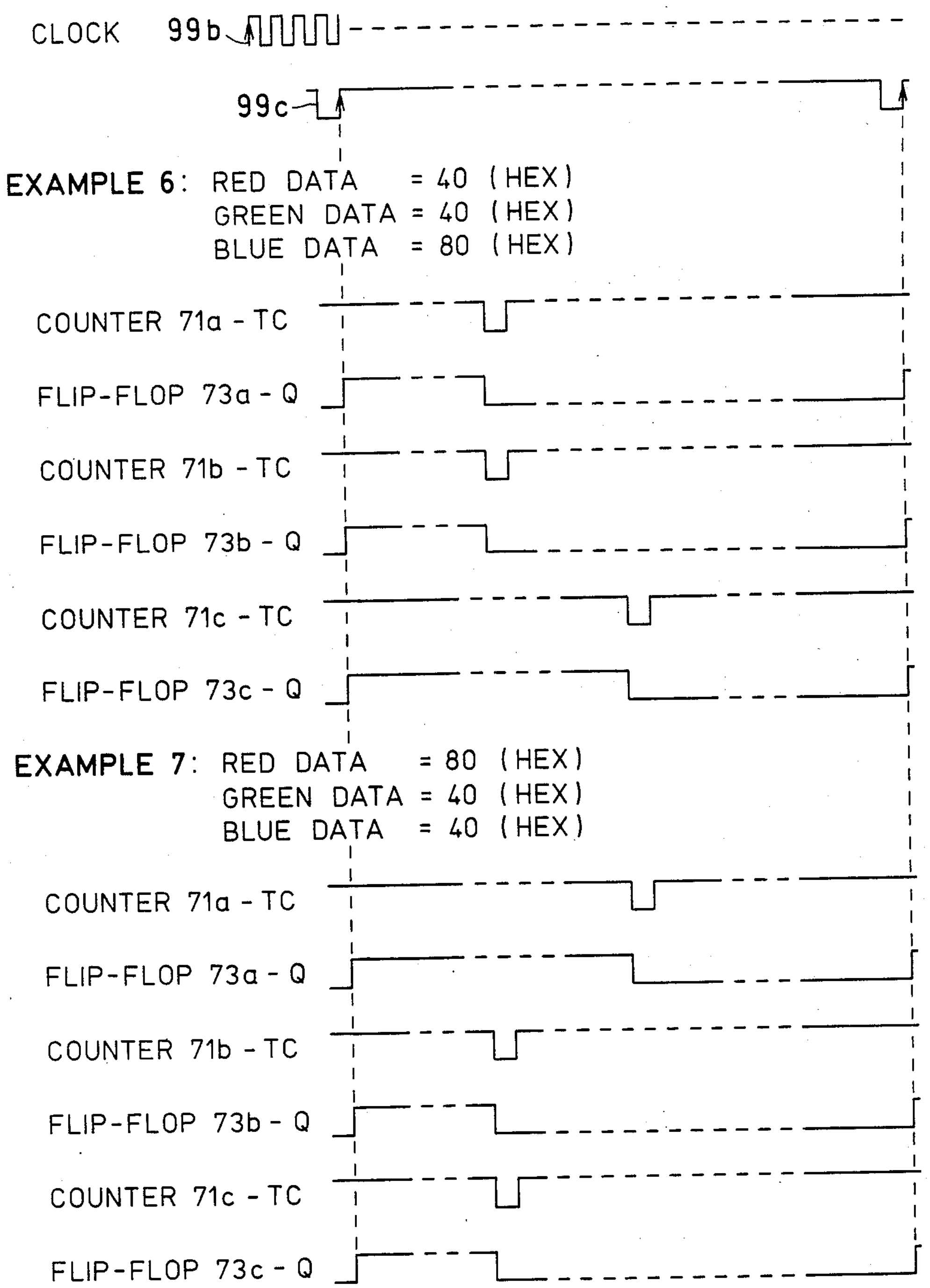
FIG. 37 is a continuation of the timing diagram of FIG. 36.

The description of the schematic diagram of a 3-LED color converter in FIG. 35 should be taken together with its accompanying timing diagrams shown in FIGS. 36 and 37. A clock signal 99*b* is applied to the CP inputs of the counters 71*d*, 71*a*, 71*b*, 71*c*, to step same down. Every 256 counts a negative pulse 99*c* is generated at the TC output of the counter 71*d*, to load data into the counters 71*a*, 71*b*, 71*c* from respective memories 76*a*, 76*b*, 76*c*, and to set the flip-flops 73*a*, 73*b*, 73*c*. The data in the RED memory 76*a* represent the portions of the red color, the data in the GREEN memory 76*b* represent the portions of the green color, and the data in the BLUE memory 76*c* represent the portions of the blue color to be blended together.

The counters 71*a*, 71*b*, 71*c* will count down, from the respective loaded values, until zero counts are reached. When the respective values of the loaded data are different, the length of time of the count-down will be different for each counter. When a particular counter reaches zero count, its TC output will momentarily drop to a low logic level, to reset its associated flip-flop (the RED counter 71*a* resets its RED flip-flop 73*a*, etc.). Eventually, all three flip-flops 73*a*, 73*b*, 73*c* will be reset. The Q outputs of the flip-flops 73*a*, 73*b*, 73*c* are connected to the red bus 5, green bus 6, and blue bus 7, respectively, via suitable buffers 62*a*, 62*b*, 62*c*, as shown in FIG. 12, to energize the respective buses for variable periods of time.

By referring now more particularly to the timing diagram shown in FIGS. 36 and 37, the EXAMPLE 4 considers the red memory data '80', green memory data '00', and blue memory data '80', all in hexadecimal notation, to generate light of substantially purple color. At the beginning of the counter cycle, the pulse 99*c* will simultaneously load the data '80' from the red memory 76*a* into the red counter 71*a*, data '00' from the green memory 76*b* into the green counter 71*b*, and data '80' from the blue memory 76*c* into the blue counter 71*c*. The counters 71*a*, 71*b*, 71*c* will be thereafter stepped down. The red counter 71*a* will reach its zero count after 128 clock cycles; the green counter 71*b* will reach its zero count immediately; the blue counter 71*c* will reach its zero count after 128 clock cycles.

It is readily apparent that the red flip-flop 73*a* was set for 128 clock cycles, or about 50% of the time, the green flip-flop 73*b* was never set, and the blue flip-flop 73*c* was set for 128 clock cycles, or about 50% of the time. Accordingly, the red bus 5 of the display 43 will be energized for about 50% of the time, green bus 6 will never be energized, and blue bus 7 will be energized for about 50% of the time. As a result of blending together substantially equal portions of red and blue colors, the display 43 will illuminate in substantially purple color.

The EXAMPLE 5 considers the red memory data '00', green memory data '00', and blue memory data '80', to generate light of substantially blue-green color. At the beginning of the counter cycle, the data '00' are loaded into the red counter 71*a*, data '80' are loaded into the green counter 71*b*, and data '80' are loaded into the blue counter 71*c*. The red counter 71*a* will reach its zero count immediately, the green counter 71*b* will reach its zero count after 128 clock periods, and so will the blue counter 71*c*.

The red flip-flop 73*a* was never set, the green flip-flop 73*b* was set for 128 clock pulses, or about 50% of the time, and so was the blue flip-flop 73*c*. Accordingly, the green bus 5 of the display 43 will be energized for about 50% of the time, and so will be the blue bus. As a result, the display 43 will illuminate in substantially blue-green color.

The EXAMPLE 6 considers the red memory data '40', green memory data '40', and blue memory data '80', to generate light of substantially cyan color. At the beginning of the counter cycle, the data '40' are loaded into the red counter 71*a*, data '40' are loaded into the green counter 71*b*, and data '80' are loaded into the blue counter 71*c*. The red counter 71*a* will reach its zero count after 64 clock cycles, and so will the green counter 71*b*. The blue counter 71*c* will reach its zero count after 128 clock cycles.

The red flip-flop 73*a* was set for 64 clock cycles, or about 25% of the time, and so was the green flip-flop 73*b*. The blue flip-flop 73*c* was set for 128 clock periods, or about 50% of the time. Accordingly, the red bus 5 and green bus 6 of the display 43 will be energized for about 25% of the time, and the blue bus 7 will be energized for about 50% of the time. As a result of blending about 50% of blue color, 25% of red color, and 25% of green color, the display 43 will illuminate in substantially cyan color.

The EXAMPLE 7 considers the red memory data '80', green memory data '40', and blue memory data '40', to generate light of substantially magenta color. At the beginning of the counter cycle, the data '80' are loaded into the red counter 71*a*, data '40' are loaded into the green counter 71*b*, and data '40' are loaded into the blue counter 71*c*. The red counter 71*a* will reach its zero count after 128 clock cycles, the green counter 71*b* will reach its zero count after 64 clock cycles, and so will the blue counter 71*c*.

The red flip-flop 73*a* was set for 120 clock cycles, or about 50% of the time, the green flip-flop 73*b* and blue flip-flop 73*c* were set for 64 clock cycles, or about 25% of the time. Accordingly, the red bus 5 of the display 43 will be energized for about 50% of the time, green bus 6 and blue bus 7 will be energized for about 25% of the time. As a result, the display 43 will illuminate in substantially magenta color.

Figure 38:
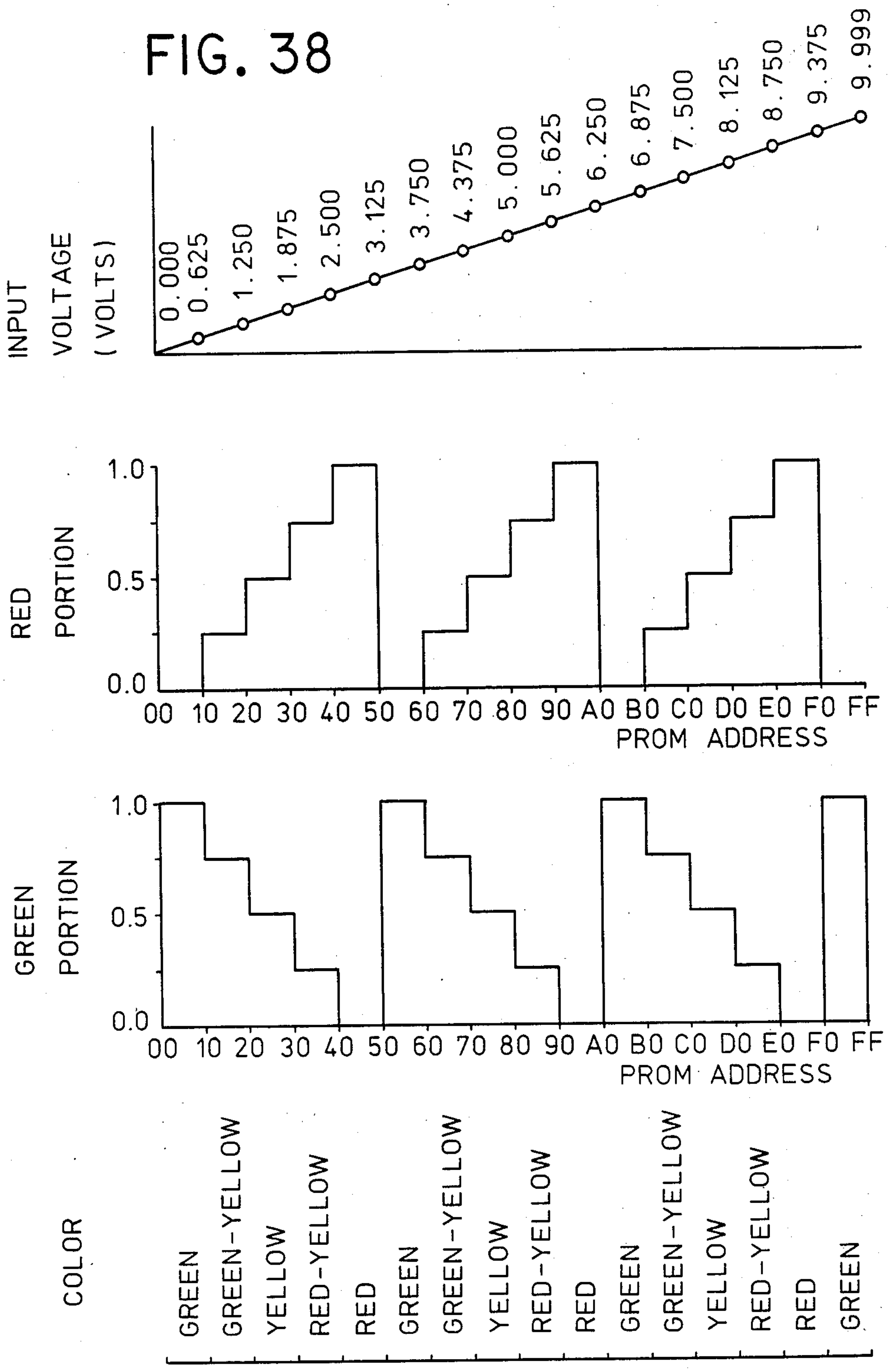
FIG. 38 is a graphic representation of the TABLE 1.
Figure 39:
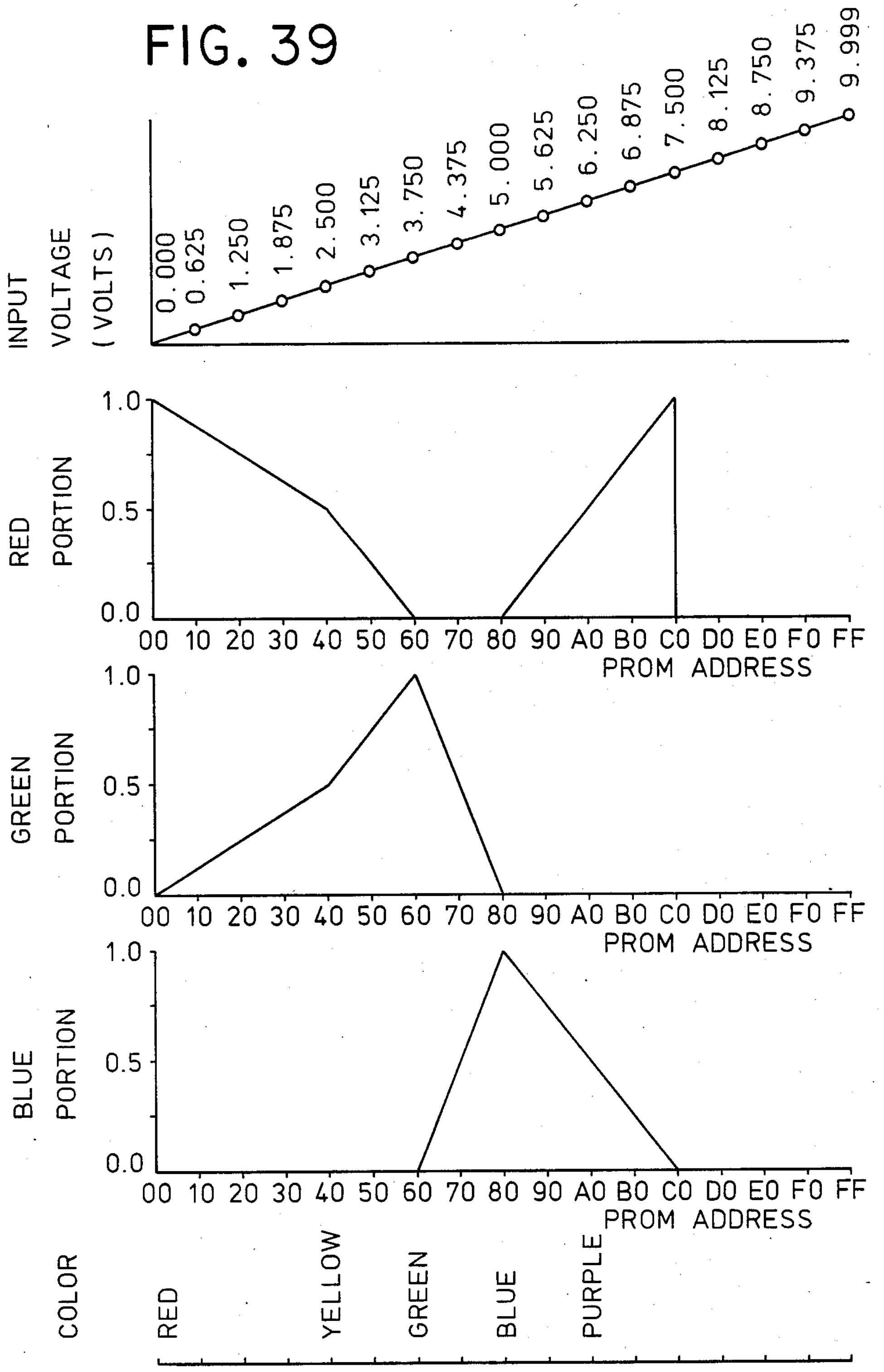
FIG. 39 is a graphic representation of the TABLE 2.

By referring now more particularly to FIGS. 38 and 39, which are graphic representations of the TABLES 1 and 2, respectively, the data at each memory address are digital representation of the portion of the particular primary color. All examples consider an 8-bit wide PROM (Programmable Read Only Memory). However, the principles of the invention could be applied to other types of memories.

In FIG. 38 the RED PORTION indicates the portion of red primary color; the GREEN PORTION indicates the portion of green primary color. The RED PORTION for a particular memory address was calculated by dividing the actual value of data residing at that address by the maximum possible data 'FF' (HEX). The GREEN PORTION for the same memory address is complementary; it was obtained by subtracting the calculated value of the RED PORTION from number 1.0.

In FIG. 38 is shown the characteristic of 2-primary color converter, defined in the TABLE 1, for developing color variable in steps: pure green for input voltages less than 0.625 V, substantially yellow for voltages between 1.25 V and 1.875 V, pure red for voltages between 2.5 V and 3.125 V, and of intermediate colors therebetween, this sequence being repeated three times over the voltage range.

In FIG. 39 the RED PORTION indicates the portion of red primary color; the GREEN PORTION indicates the portion of green primary color; the BLUE PORTION indicates the portion of blue primary color. The RED PORTION for a particular memory address was calculated by dividing the value of RED data residing at such address by the maximum possible data 'FF' (HEX). Similarly, the GREEN PORTION for that memory address was obtained by dividing the value of GREEN data by 'FF' (HEX). The BLUE PORTION was obtained by dividing the value of BLUE data by 'FF' (HEX).

In FIG. 39 is shown the characteristic of 3-primary color converter, defined in the TABLE 2, for developing color continuously variable from pure red, through substantially orange and yellow, pure green, pure blue, to substantially purple, in a rainbow-like fashion.

In the examples of the characteristics of color converters, shown in the TABLE 1 to TABLE 2, the data values stored in the red, green, and blue memories are so designed that the sums of the red data, green data, and blue data are constant for all memory addresses, to provide uniform light intensities for all colors. It is further contemplated that data stored in the red, green, and blue memories may be modified in order to compensate for different efficiencies of red, green, and blue LEDs. By way of an example, data values for a low efficiency LED may be proportionally incremented such that time of energization is proportionally increased, to effectively provide equal luminances for LEDs of unequal efficiencies.

Figure 40:
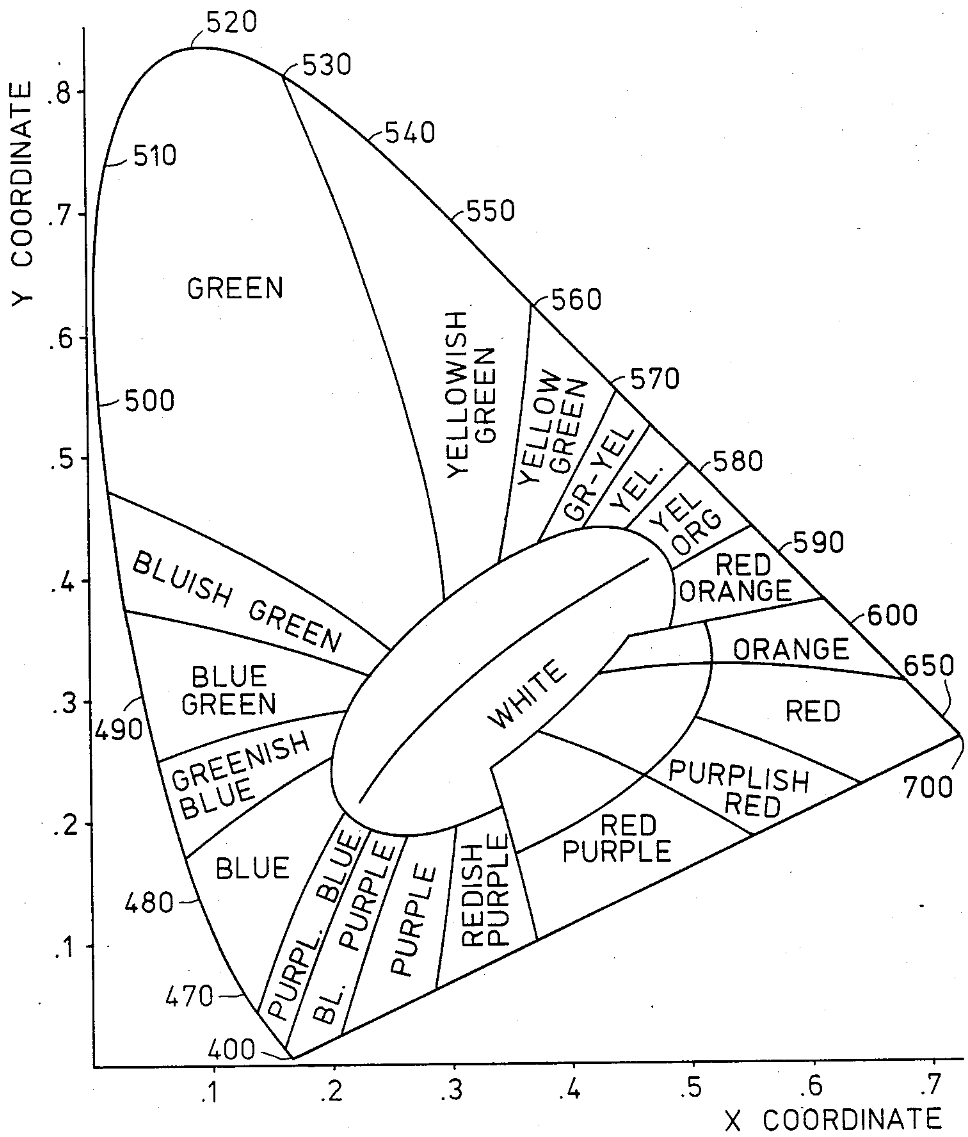
FIG. 40 is a graph of the ICI chromaticity diagram.

With reference to FIG. 40 there is shown the ICI (International Committee on Illumination) chromaticity diagram designed to specify a particular color in terms of x and y coordinates. Pure colors are located along the horseshoe-like periphery. Reference numbers along the periphery indicate wavelength in nanometers. When relative portions of three primary colors are known, the color of light produced by blending their emissions can be determined by examining the x and y values of ICI coordinates.

TIMEPIECE

Figure 41:
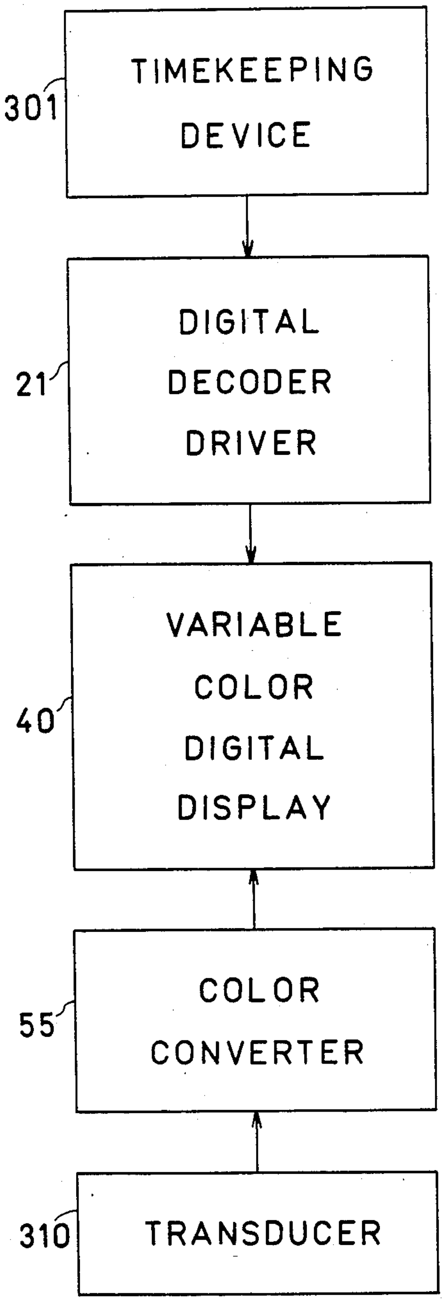
FIG. 41 is a block diagram of a timepiece with variable color digital display and a transducer.
Figure 42:
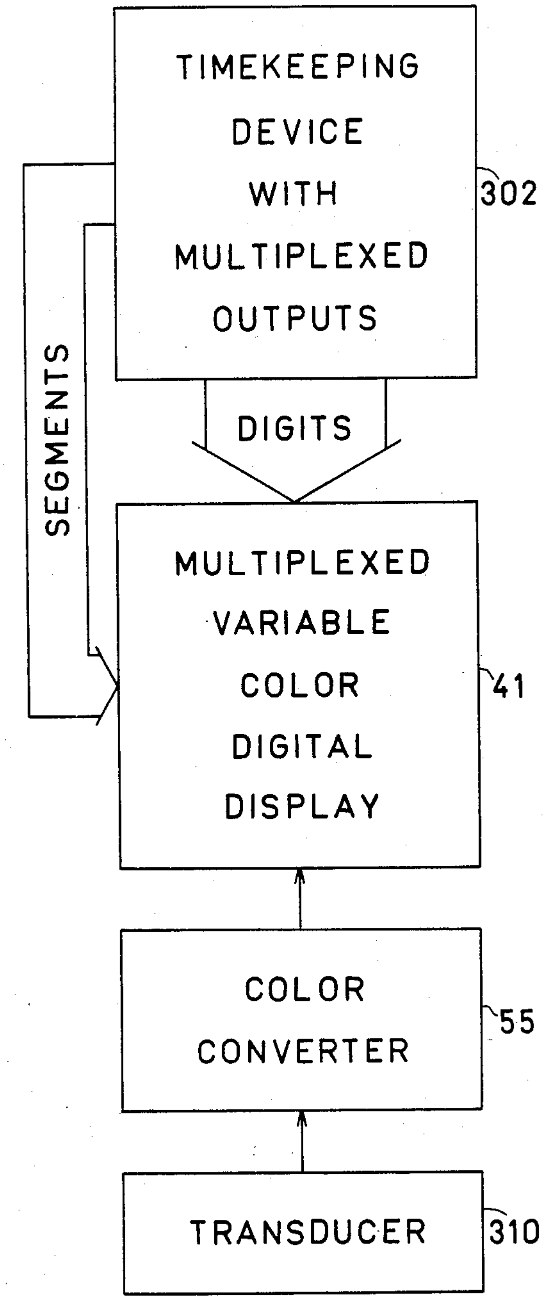
FIG. 42 is a block diagram of a like timepiece characterized by multiplexed outputs.

FIG. 41 is a generalized block diagram of a timepiece with transducer of this invention which includes a timekeeping device 301 for keeping time and for developing output electrical signals indicative of time, a digital decoder driver 21 for converting the timekeeping device's output electrical signals into a displayable code, and variable color digital display 40 for indicating time in digital format. The invention resides in the addition of a transducer 310 for measuring a physical quantity and for developing output electrical signals related to values of such physical quantity, and of a color converter circuit 55 for converting output electrical signals of the transducer 310 to color control signals for controlling the color of the display 40. The display 40 will thus simultaneously indicate time, in digital format, and values of the measured physical quantity, in variable color.

The timekeeping device 301 typically contains a high frequency accurate time standard signal generator and a chain of frequency dividers for providing highly stable clock signal of 1 Hz frequency which drives the seconds, minutes, and hours counters (not shown). The digital decoder driver 21 continuously converts output signals of such counters to suitable codes for driving multidigit display 40, in a manner well understood by those skilled in the art.

The term transducer, as used throughout the description of the invention, is used in its widest sense so as to include every type of a device for performing a conversion of one type of energy to another. The principles of the invention may be applied to various displacement, motion, force, pressure, sound, flow, temperature, humidity, weight, magnetic, and physiological transducers and the like.

A physiological transducer is defined for the purpose of this invention as means for producing electrical signals which represent physiological conditions or events in a human body or other living matter.

Figure 43:
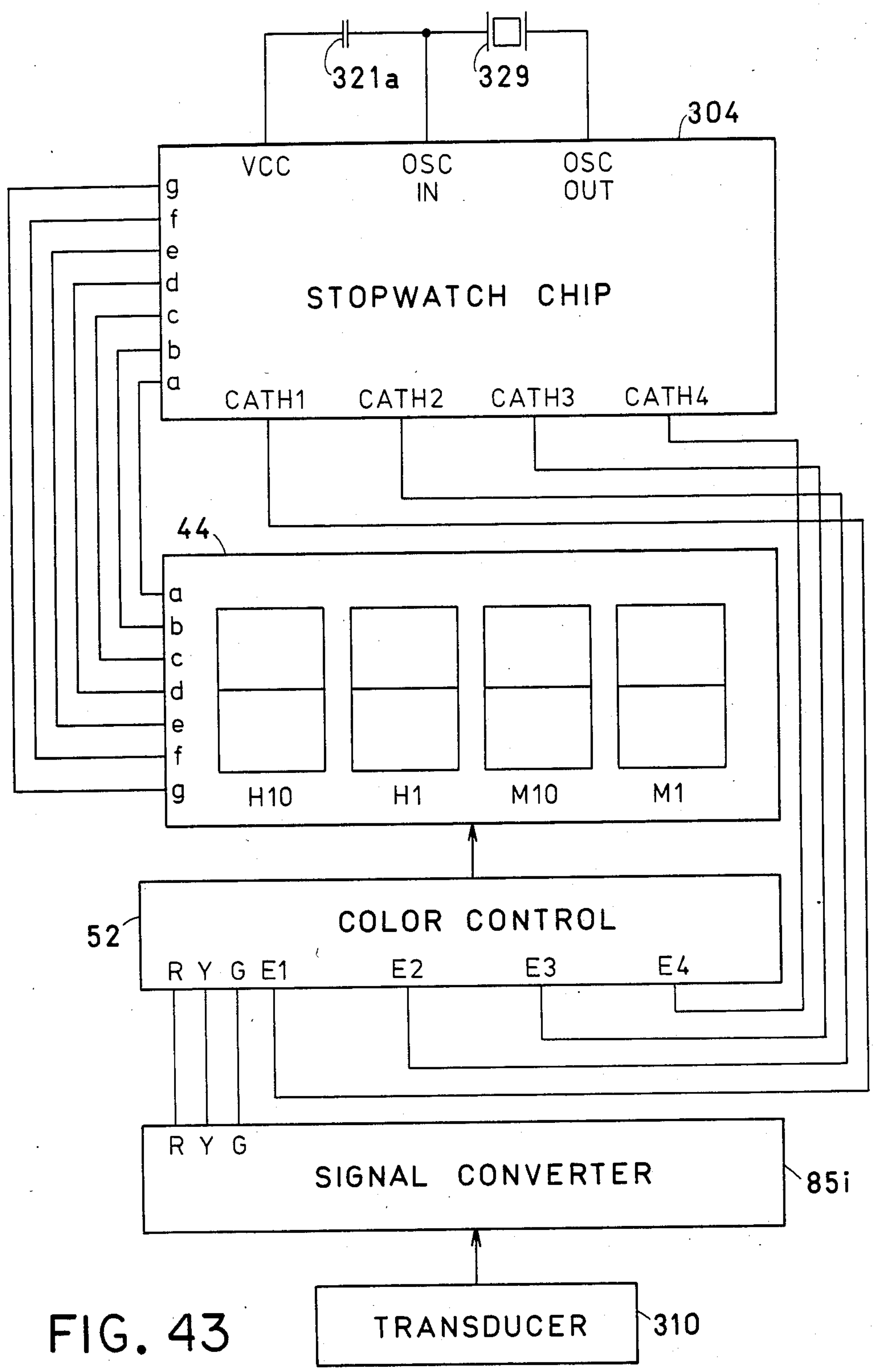
FIG. 43 is an expanded block diagram of a timepiece with variable color digital display and 3-step color control for all display digits.

A timepiece shown in a schematic diagram in FIG. 43 includes a stopwatch chip 304 for developing multiplexed segment drive signals a, b, c, d, e, f, and g to directly drive a 4-digit 2-LED variable color digital display 44, which will indicate time in hours (on digits H10 and H1) and minutes (on digits M10 and M1), in a manner well understood by those skilled in the art. The multiplexing enable signals Cath1, Cath2, Cath3, and Cath4 are utilized to sequentially enable respective digits of the display 44, as shown in the detail in FIG. 19, at a relatively fast rate, to thereby provide a flicker-free display in a color determined by the instant conditions of the color control inputs R, Y, and G.

The invention resides in the addition of a transducer 310 for developing electrical signals related to values of the measured physical quantity, and a signal converter **85*i*, for converting the transducer's output electrical signals to color control signals R, Y, and G, as shown in the detail in FIGS. 21 and 23, to thereby control the color of the display 44** in three steps in accordance with the values of the measured physical quantity.

Figure 44:
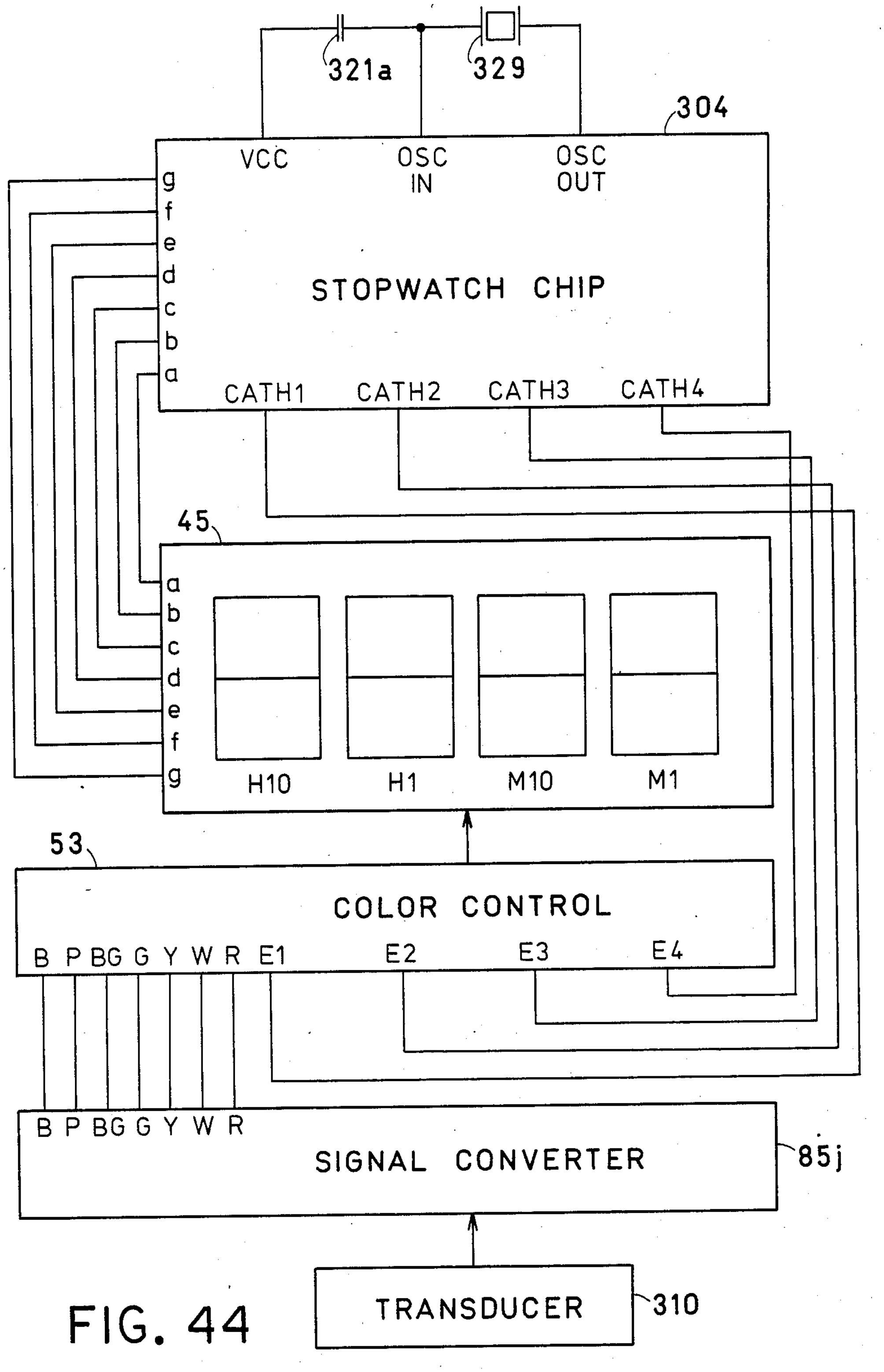
FIG. 44 is an expanded block diagram of a like timepiece with 7-step color control for all display digits.

In FIG. 44 is shown a like schematic diagram of a timepiece, which differs from the one shown in FIG. 43 in that a 4-digit 3-LED variable color digital display 45 and a signal converter **85*j* are utilized for converting the transducer's output electrical signals to color control signals B, P, BG, G, Y, W, and R, as shown in the detail in FIGS. 22 and 25, to control the color of the display 45 in seven steps in accordance with the values of the measured physical quantity. The detail of the interconnection of the four display digits is shown in FIG. 20**.

Figure 45:
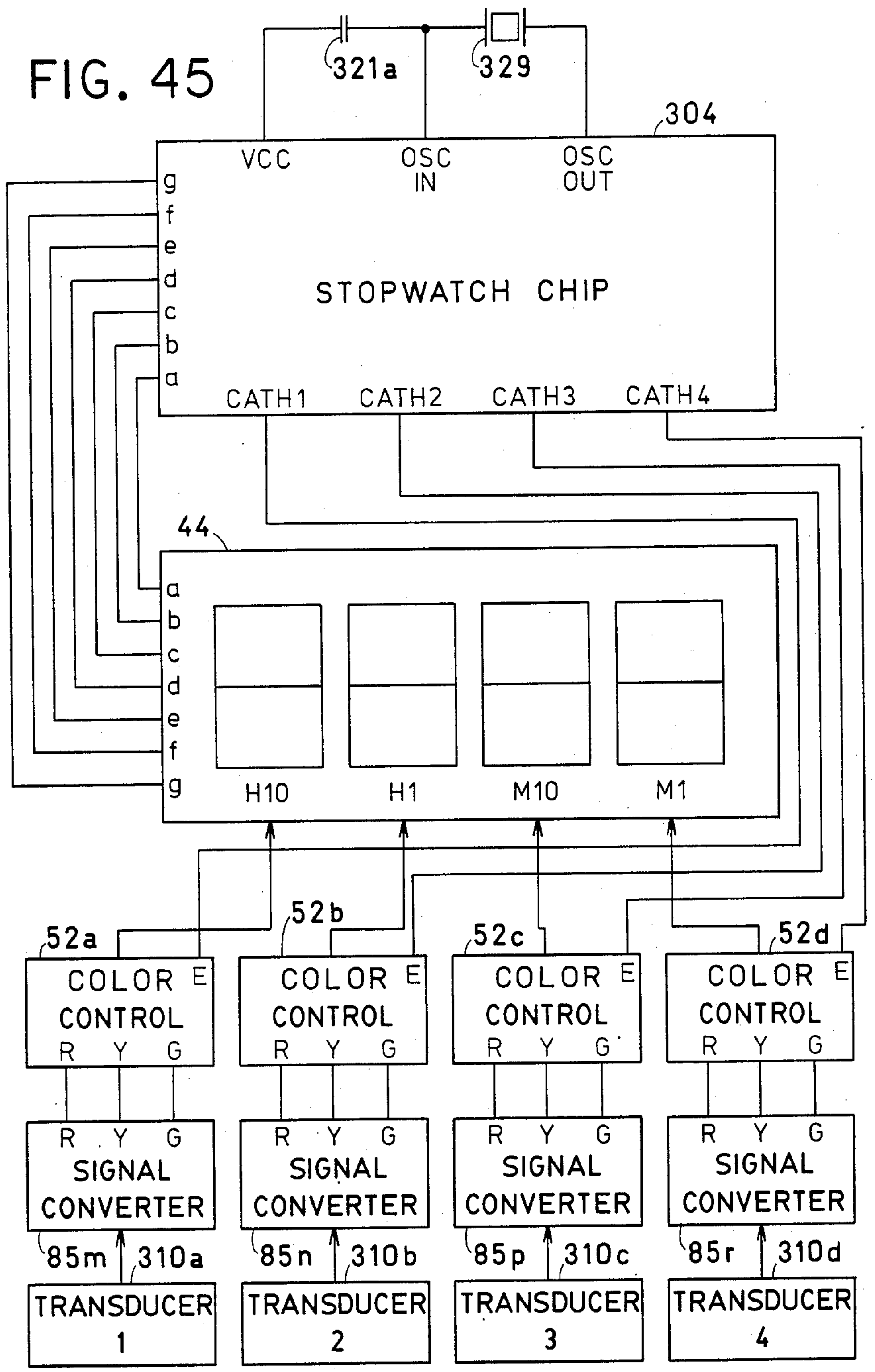
FIG. 45 is an expanded block diagrams of a timepiece with variable color digital display and 3-step color controls for individual display digits.

In FIG. 45 is shown a schematic diagram of a timepiece which differs from a like diagram shown in FIG. 43 in that four transducers **310*a*, 310*b*, 310*c*, and 310*d* with associated signal converters 85*m*, 85*n*, 85*p*, 85*r* and color control circuits 52*a*, 52*b*, 52*c*, 52*d* are used to independently control the color of respective display digits in three steps. The display 44** will indicate time in digital format and each display digit will illuminate in a color in accordance with the value of a physical quantity measured by the associated transducer.

Figure 46:
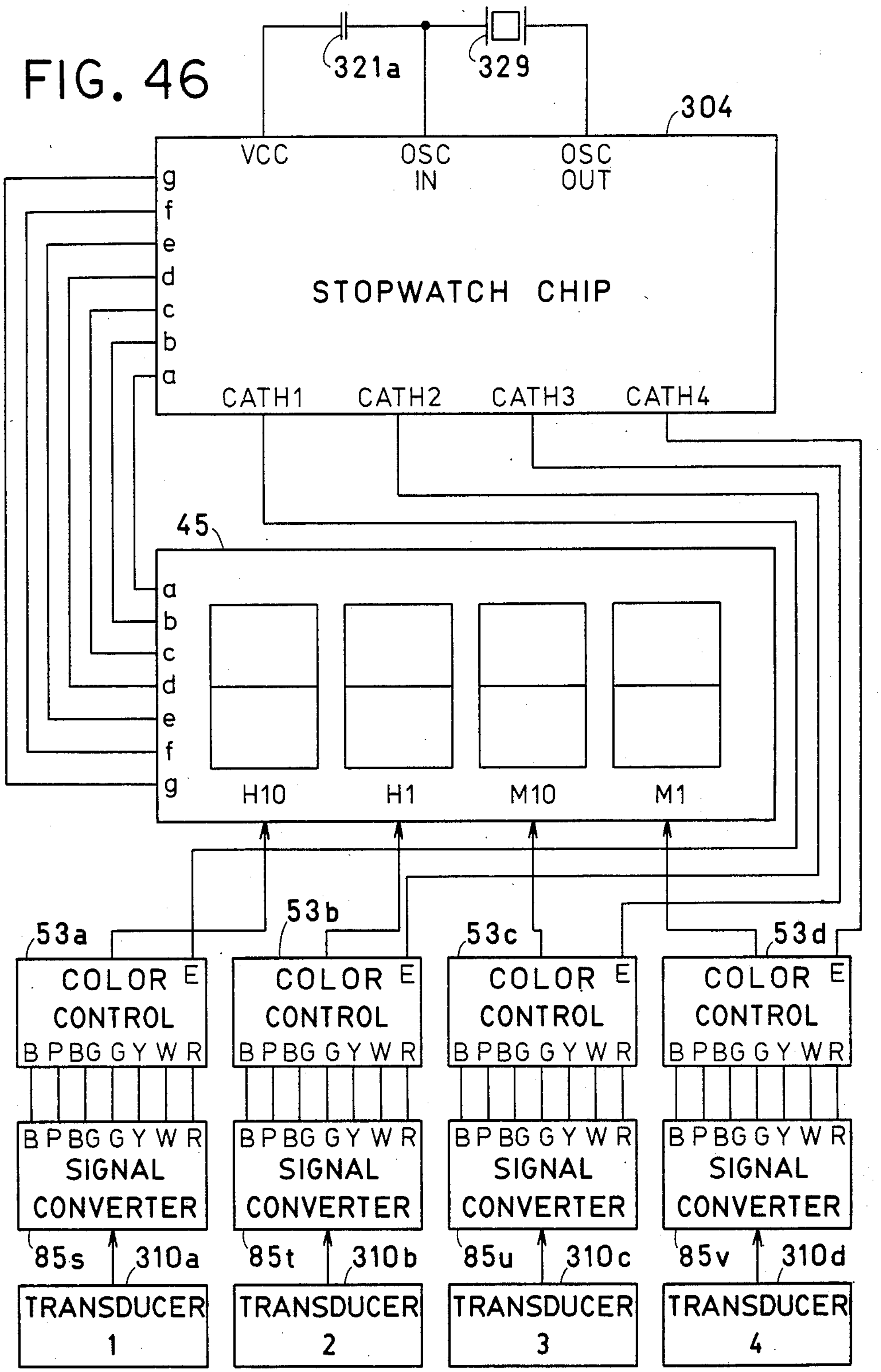
FIG. 46 is an expanded block diagram of a like timepiece with 7-step color control for individual display digits.

In FIG. 46 is shown a schematic diagram of a timepiece utilizing four transducers **310*a*, 310*b*, 310*c*, and 310*d* with associated signal converters 85*s*, 85*t*, 85*u*, 85*v* and color control circuits 53*a*, 53*b*, 53*c*, 53*d* to independently control the color of respective display digits of the display 45** in seven steps in accordance with four different physical quantities measured by respective transducers.

Figure 47:
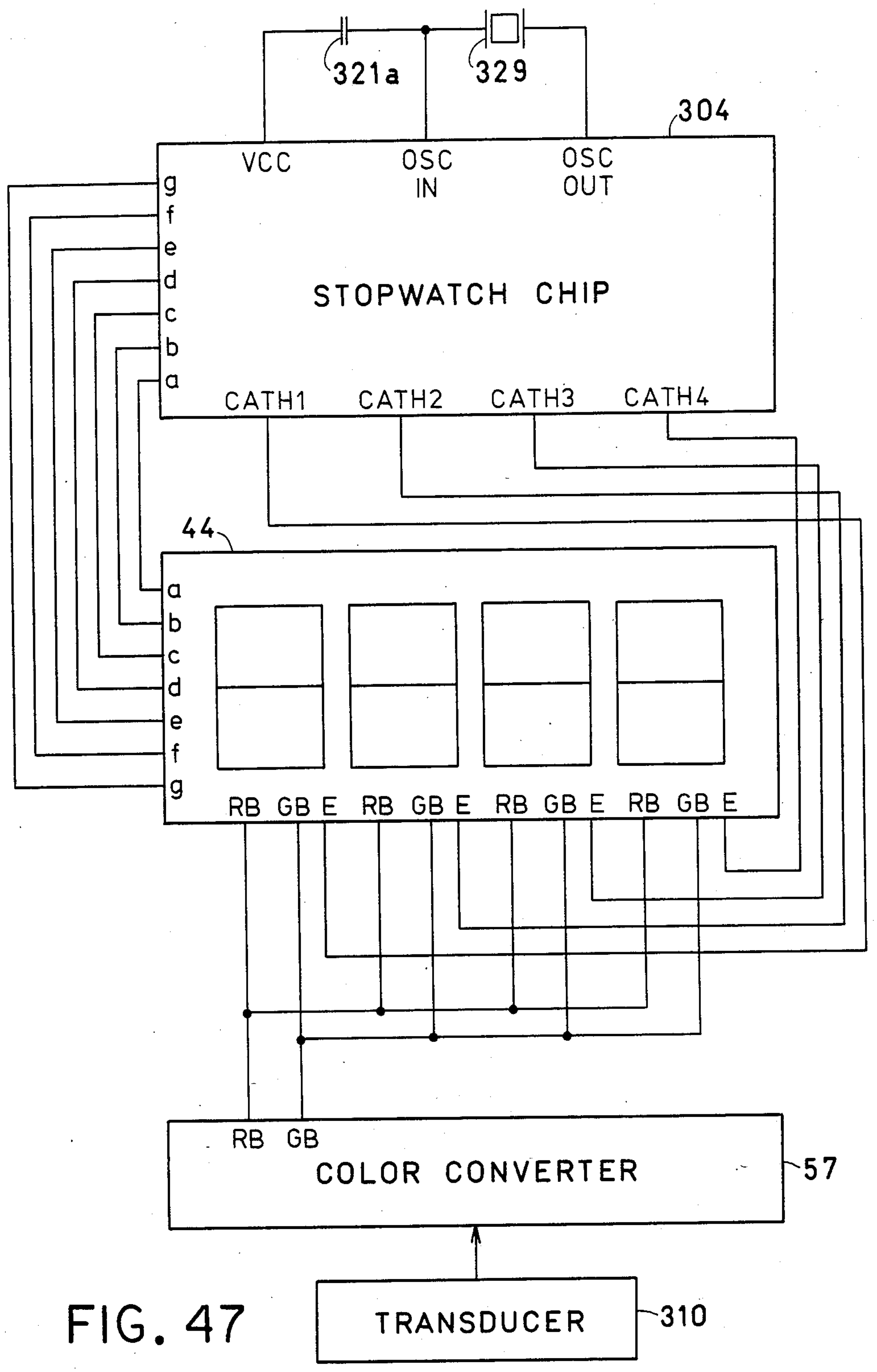
FIG. 47 is an expanded block diagram of a timepiece with 2-LED continuously variable color digital display and color control for all display digits.

In FIG. 47 is shown a schematic diagram of a timepiece characterized by a 2-primary color converter 57 for converting output electrical signals of the transducer 310 to drive signals RB (for the red bus) and GB (for the green bus), as shown in the detail in FIGS. 29 to 34, to control the color of the 4-digit 2-LED variable color digital display substantially continuously in accordance with the values of the physical quantity measured by the transducer such that the color changes of the display are proportional to changes in the values of the physical quantity.

Figure 48:
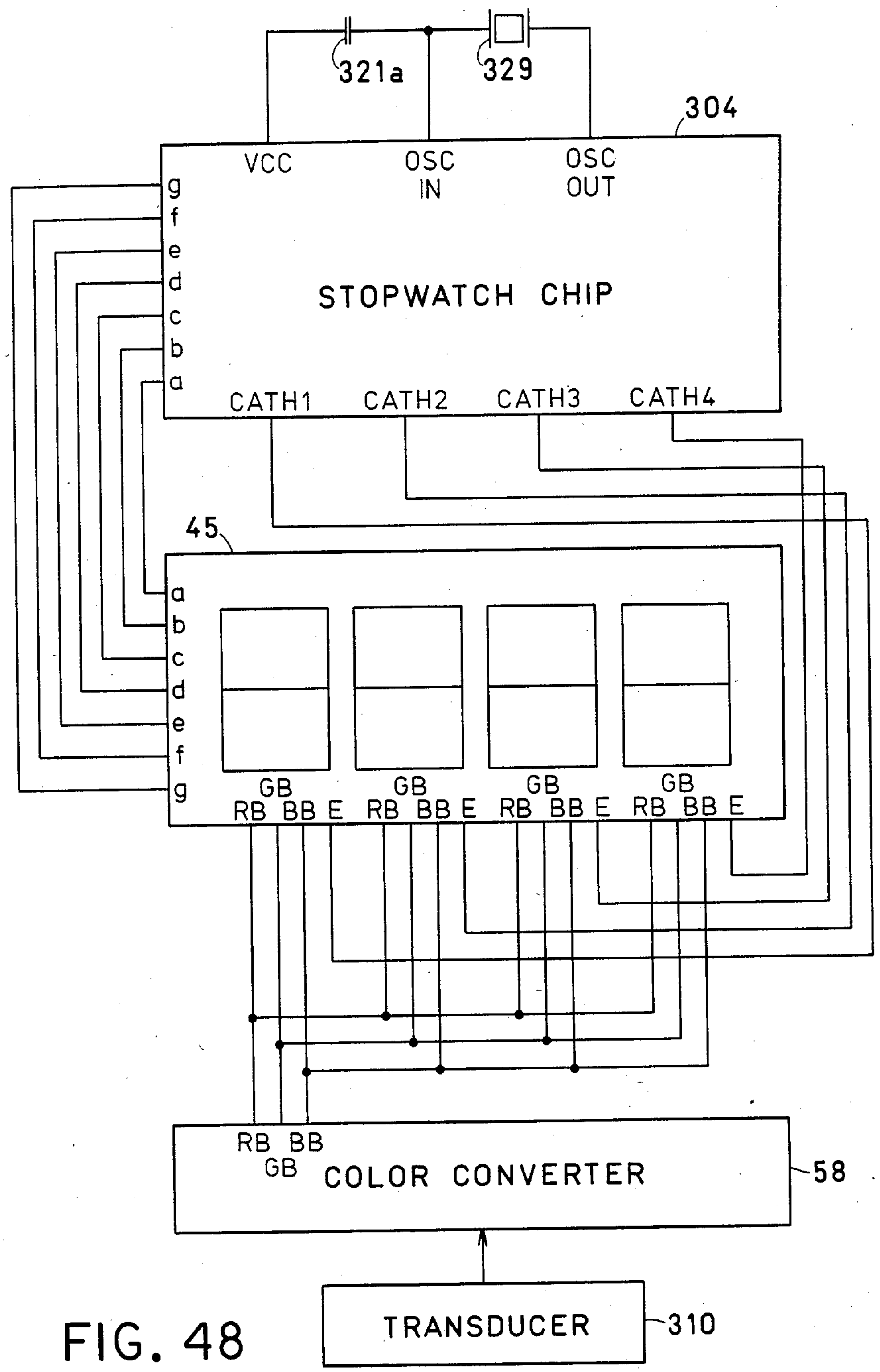
FIG. 48 is an expanded block diagram of a like timepiece characterized by 3-LED continuously variable color digital display.

Similar schematic diagram of a timepiece shown in FIG. 48 differs from the one shown in FIG. 47 in that a 3-primary color converter 58 is utilized for converting output electrical signals of the transducer 310 to drive signals RB, GB and BB (for the blue bus), as shown in the detail in FIGS. 30, 35 to 37, to control the color of 4-digit 3-LED variable color digital display substantially continuously in accordance with the values of the physical quantity measured by the transducer such that the color changes of the display are proportional to changes in the values of the physical quantity.

Figure 49:
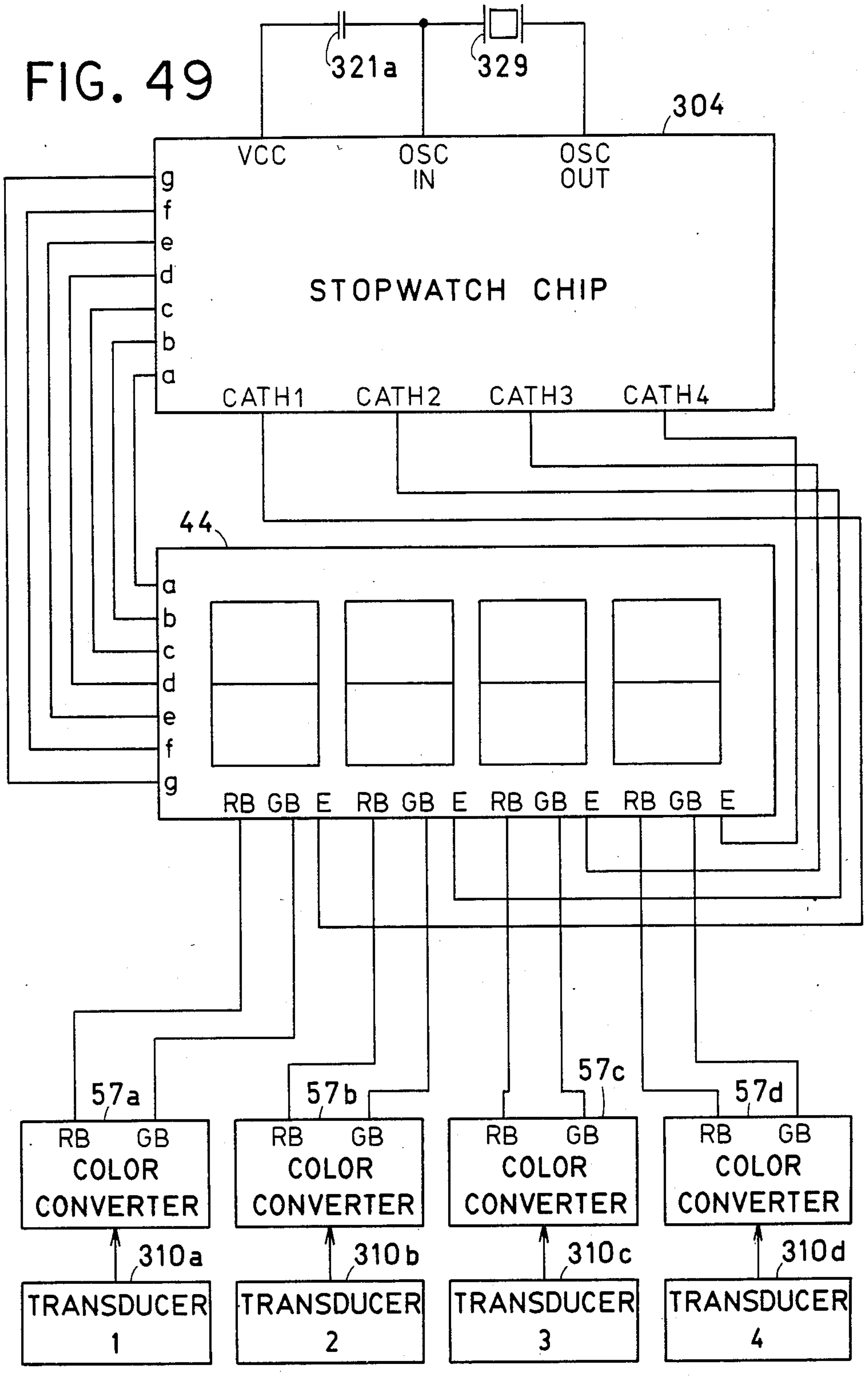
FIG. 49 is an expanded block diagram of a timepiece with 2-LED continuously variable color digital display and color converters for individual display digits.

In FIG. 49 is shown a schematic diagram of a timepiece which differs from a like diagram shown in FIG. 47 in that four transducers 310*a*, 310*b*, 310*c*, and 310*d* with associated 2-primary color converters 57*a*, 57*b*, 57*c*, and 57*d* are used to independently control the color of respective display digits of the 4-digit 2-LED display 44 substantially continuously in accordance with four different physical quantities measured by respective transducers.

Figure 50:
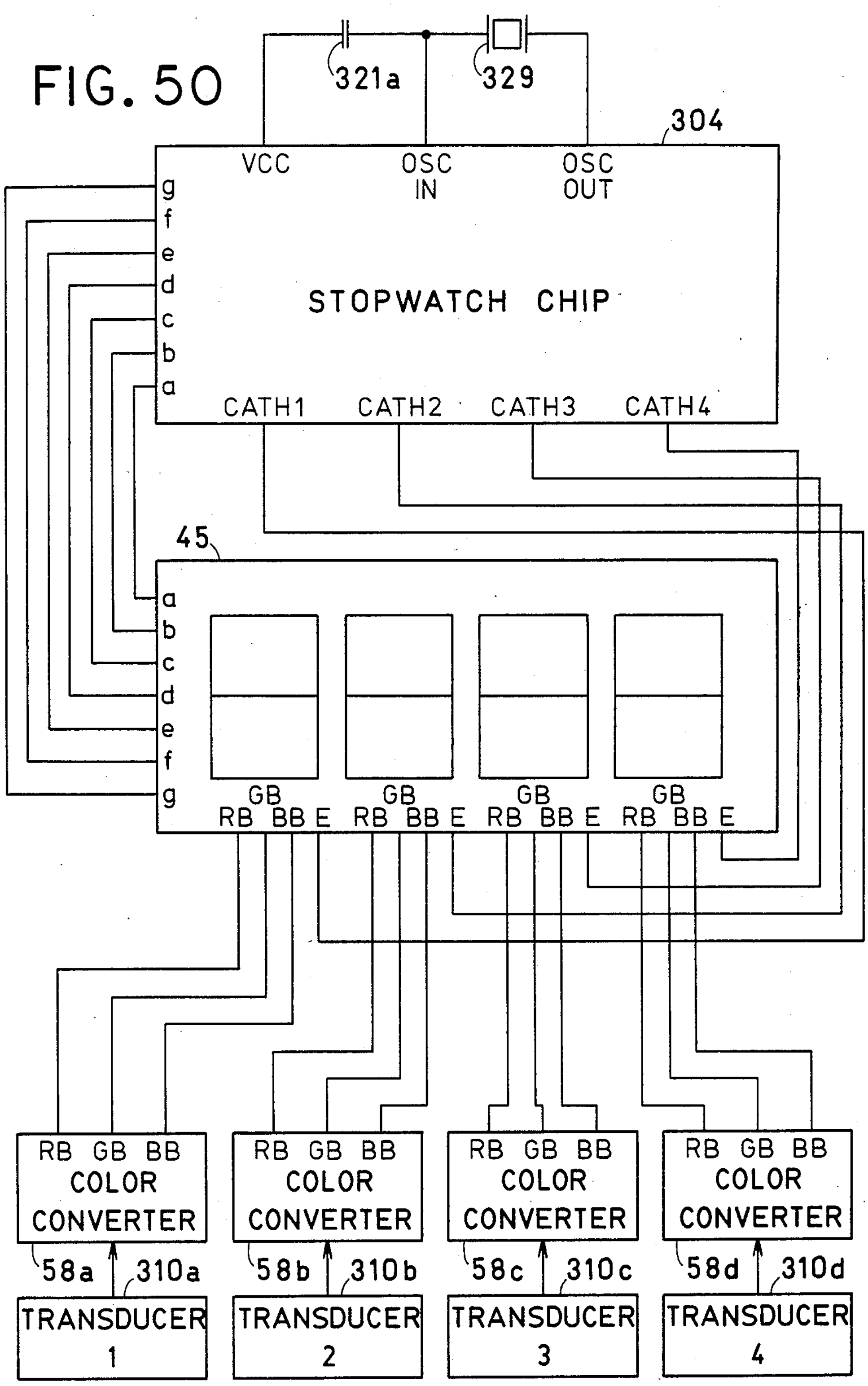
FIG. 50 is an expanded block diagram of a like timepiece characterized by 3-LED continuously variable color digital display.

In FIG. 50 is shown a schematic diagram of a timepiece utilizing four transducers 310*a*, 310*b*, 310*c*, and 310*d* with associated 3-primary color converters 58*a*, 58*b*, 58*c*, and 58*d* to independently control the color of respective display digits of the 4-digit 3-LED display 45 substantially continuously in accordance with four different physical quantities measured by respective transducers.

Figure 51:
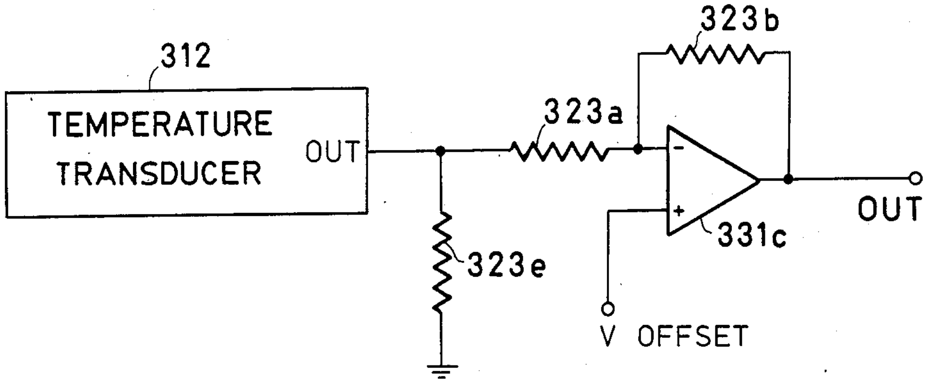
FIG. 51 is a schematic diagram of a temperature transducer with interface circuit.

In a schematic diagram shown in FIG. 51, temperature transducer 312 measures ambient temperature and develops at its output a current which is linearly proportional to measured temperature in degrees Kelvin. The current flows through a resistor 323*e* of suitable value (e.g., 1 k Ohm), to develop voltage proportional to the measured temperature, which is applied to the input of an op amp 331*c*. To read at the op amp's output OUT voltage that directly corresponds to temperature in degrees Celsius, the other input of the op amp is offset by 273.2 mV. The invention resides in utilizing the output voltage at the terminal OUT to develop color control signals for causing the display to illuminate in a color related to the measured ambient temperature. To achieve this, the terminal OUT may be connected as shown in the detail either in FIG. 23, to control the color of the display in three steps, or in FIG. 25, to control the color of the display in seven steps, or in FIGS. 29 and 30, to control the color of the display continuously.

Figure 52:
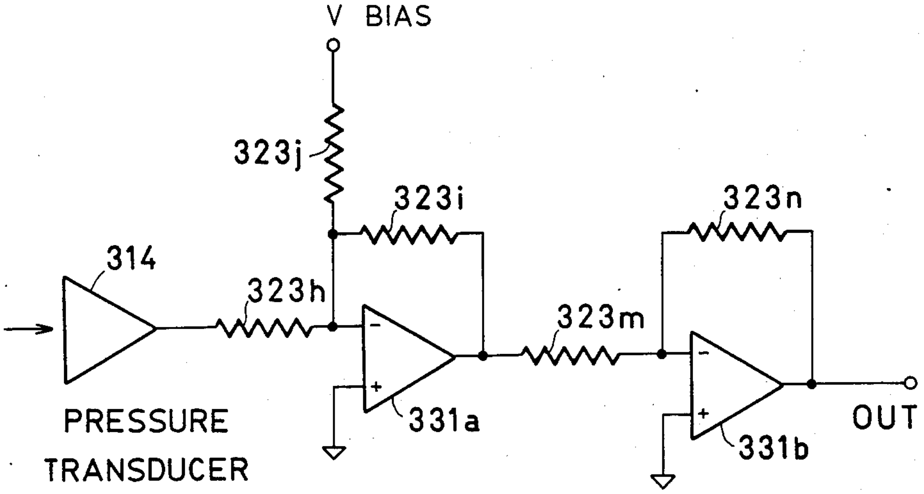
FIG. 52 is a schematic diagram of an atmospheric pressure transducer with interface circuit.

In a schematic diagram shown in FIG. 52, the pressure transducer 314 measures atmospheric pressure and develops at its output a voltage which is linearly proportional to the measured atmospheric pressure. The scaling circuit consisting of two op amps 331*a* and 331*b* with associated resistors 323*h* to 323*n* scales the transducer's output voltage, in a manner well understood by those skilled in the art, such that the resulting voltage at the terminal OUT directly corresponds to the measured atmospheric pressure, either in milibars or in mm Hg, depending on the selection of certain resistors. The invention resides in utilizing the output voltage at the terminal OUT for causing the display to illuminate in a color related to the measured atmospheric pressure. The terminal OUT may be connected as shown in FIGS. 23, 25, 29, and 30.

Figure 53:
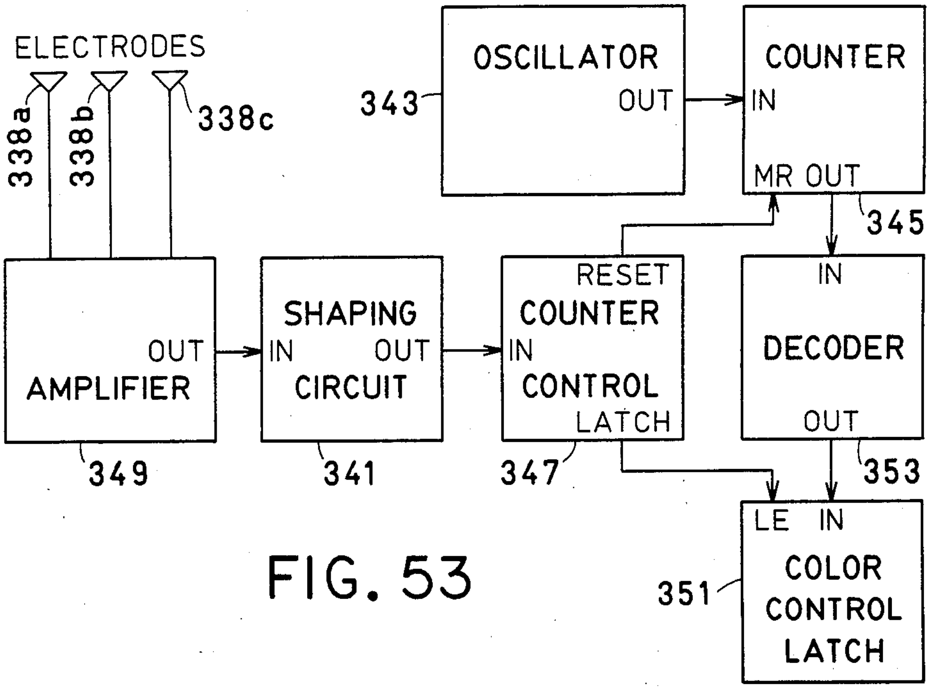
FIG. 53 is a block diagram of a heart rate transducer circuit for controlling the color of the display in steps.

In FIG. 53 is shown a block diagram of a circuit for measuring cardiac activity of the user which includes three electrodes 338*a*, 338*b*, and 338*c* adapted to be positioned on the body of the user, amplifier 349 adapted to amplify the output of the electrodes which indicates the functioning of a heart beating within the user's body, shaping circuit 341 for converting output signals of the amplifier to square wave pulses, oscillator 343 for providing a periodic sequence of clock pulses of a predetermined rate, counter 345 for counting the pulses, counter control 347, responsive to output signals of the shaping circuit, for starting and stopping the counter such that its final count is proportional to the heart rate of the user, as will be more fully explained later, decoder 353 for converting the output count of the counter to color control signals, and color control latch 351 for intermediately storing the color control signals.

Figure 54:
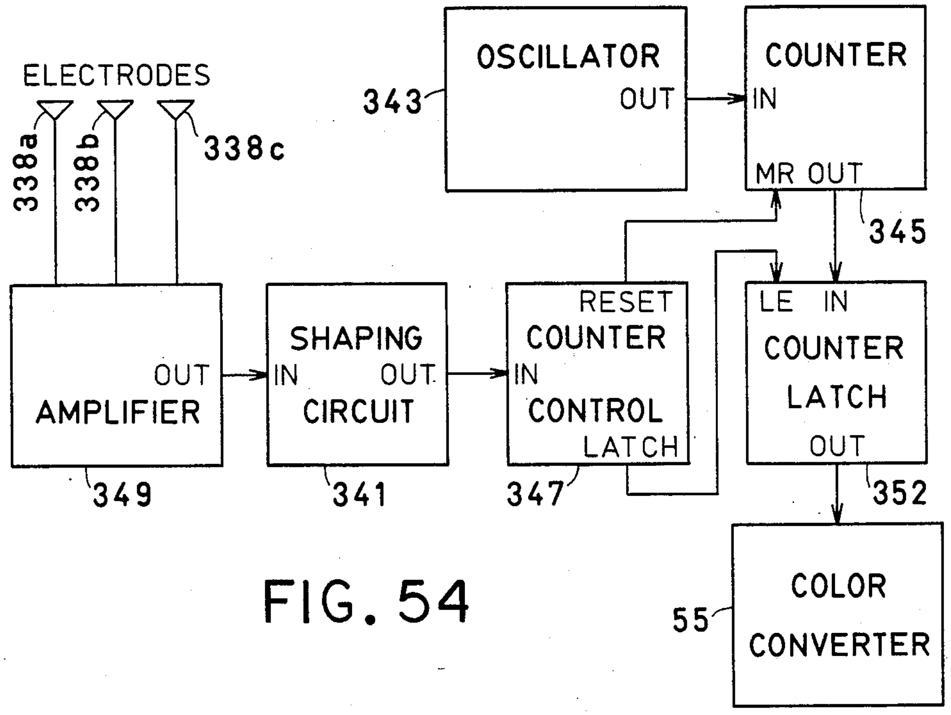
FIG. 54 is a block diagram of a heart rate transducer circuit for controlling the color of the display continuously.

In FIG. 54 is shown a block diagram of a like circuit which differs from the one shown in FIG. 53 in that a color converter 55 and counter latch 352 are used in lieu of the decoder and color control latch. When the counter completes its counting cycle, its output data will be intermediately stored in the counter latch 352 and thus applied to the input of the color converter 55.

Regular throbbing in the arteries caused by contractions of the heart can be monitored on the wrist or on many other suitable locations on the body where major arteries approach the skin. The rate and strength of the blood pulse depend on the age, sex, physiological condition, and a number of other factors. In adult person, the heart rate may range from 50 to 80 beats per minute.

Systematic monitoring of the heart rate by the device of the present invention allows to detect changes in physiological patterns in the body of the user. It also allows to explore possibilities of influencing abnormal physiological patterns by a technique of feedback.

Figure 55:
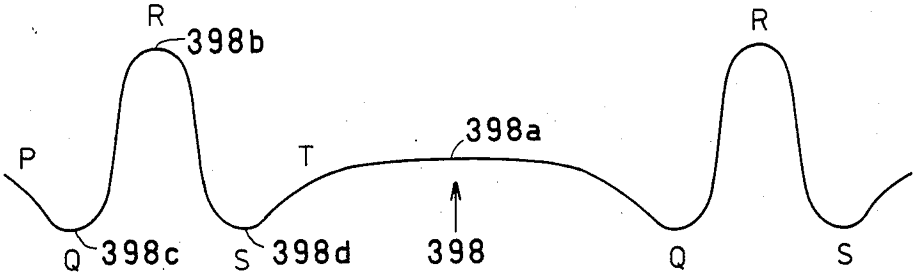
FIG. 55 is a graph showing typical electrocardiogram waves.

FIG. 55 shows well known electrocardiogram wave with its salient points indicated. The R wave 398*b* is the most distinct signal and, therefore, well known technique of counting the number of stable clock pulses between the adjacent R waves was employed to measure the heart rate.

Figure 56:
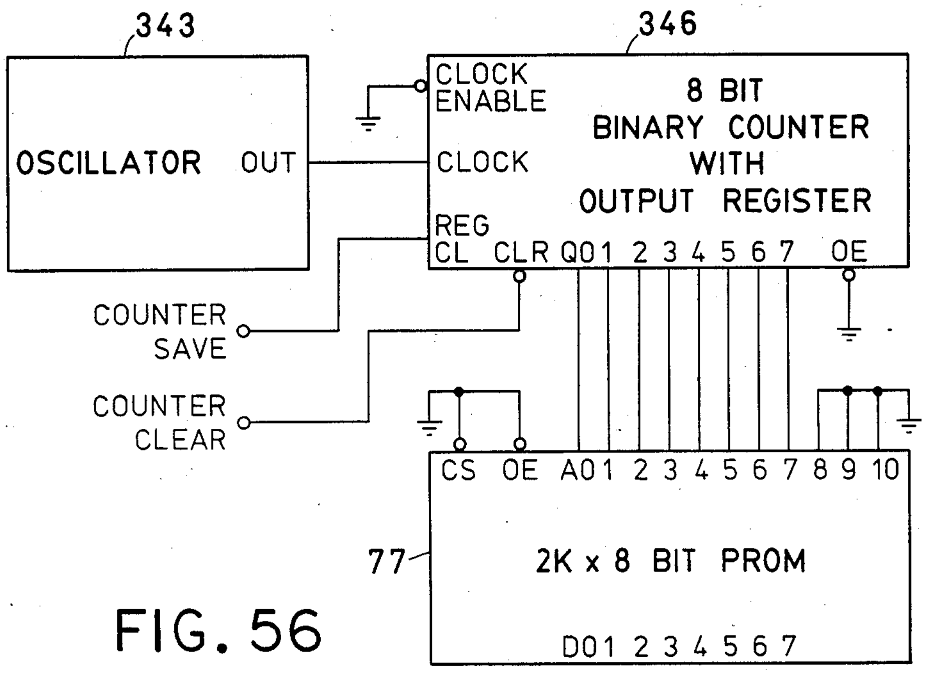
FIG. 56 is a detail of the combination of the counter shown generally in FIG. 54 with a memory for 2-primary color converter.

FIG. 56 is a detail of the counter and 2-primary color converter combination shown generally in FIG. 54. An 8-bit binary counter 346 may be from time to time reset to its zero count by applying a short negative COUNTER CLEAR pulse to its Clear input CLR. When not in its reset condition, the counter is incremented by clock pulses of suitable frequency provided by the oscillator 343. When a positive going edge COUNTER SAVE is applied to the counter's Register Clock input REG CL, the instant count data are transferred to the internal register and appear at the outputs Q0 to Q7, which are directly connected to respective address inputs A0 to A7 of the memory 77 which contains data symbolizing the portions of red color for all possible counter output data. The memory data residing at the address selected by the instant counter's output data will appear at the memory outputs D0 to D7, which may be connected as shown in the detail in FIG. 33, to cause the display to illuminate in a specific color.

Figure 57:
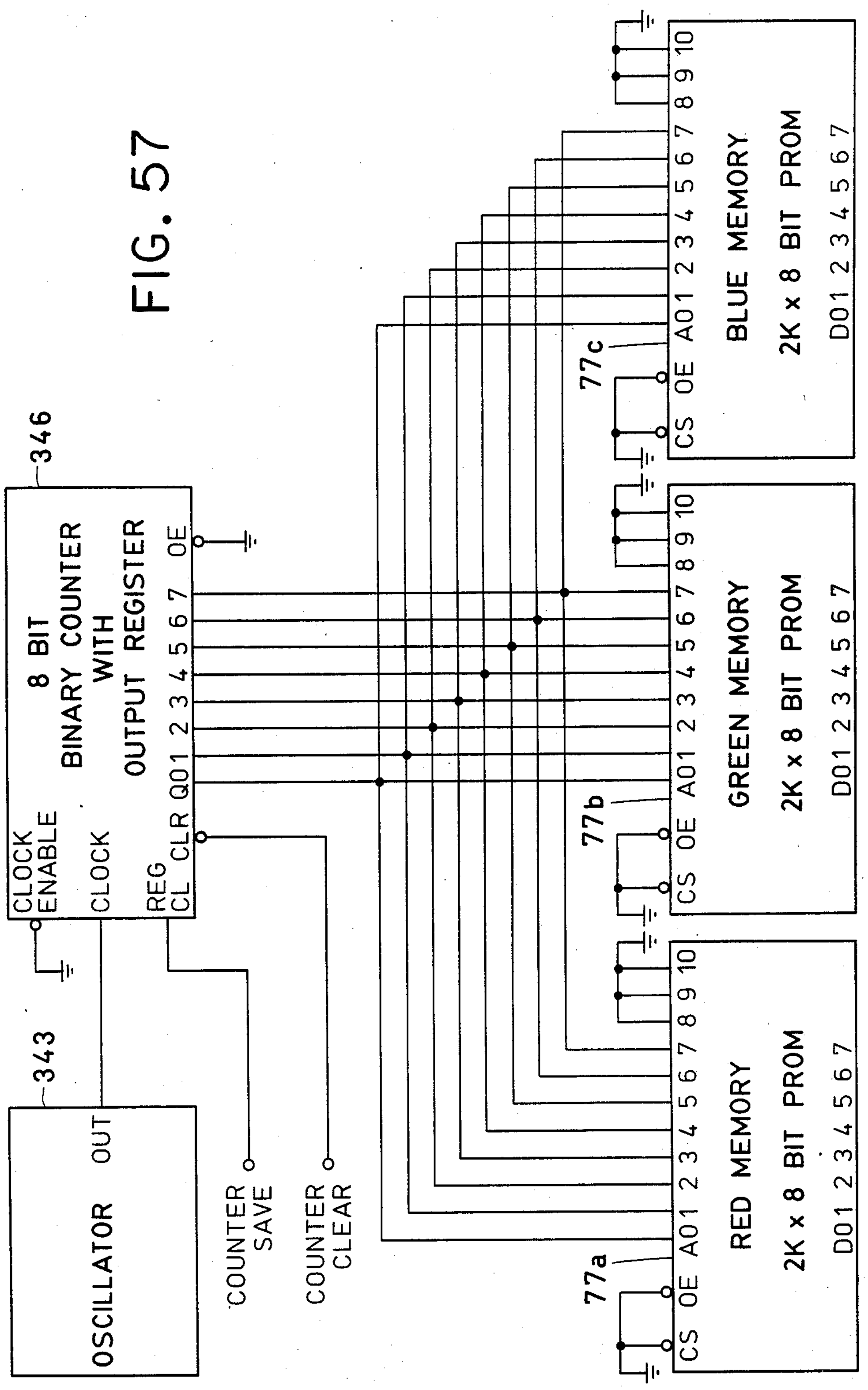
FIG. 57 is a detail of the combination of the counter shown generally in FIG. 54 with a memory for 3-primary color converter.

In FIG. 57 is shown a similar schematic diagram of the counter and 3-primary color converter combination. The outputs Q0 to Q7 of the counter 346 are respectively connected to the interconnected address inputs A0 to A7 of the RED MEMORY 77*a*, GREEN MEMORY 77*b*, and BLUE MEMORY 77*c*. When the instant output data of the counter are applied to the address inputs of the memories, the memory data residing at such address in the memory 77*a*, symbolizing the portion of red primary color, will appear at its memory outputs D0 to D7, memory datal residing at the same address in the memory 77*b*, symbolizing the portion of green primary color, will appear at its memory outputs D0 to D7, and memory data residing at the same address in the memory 77*c*, symbolizing the portion of blue primary color, will appear at its memory outputs D0 to D7. The memory outputs of the three memories may be connected as shown in the detail in FIG. 35, to cause the display to illuminate in a specific color.

Figure 58:
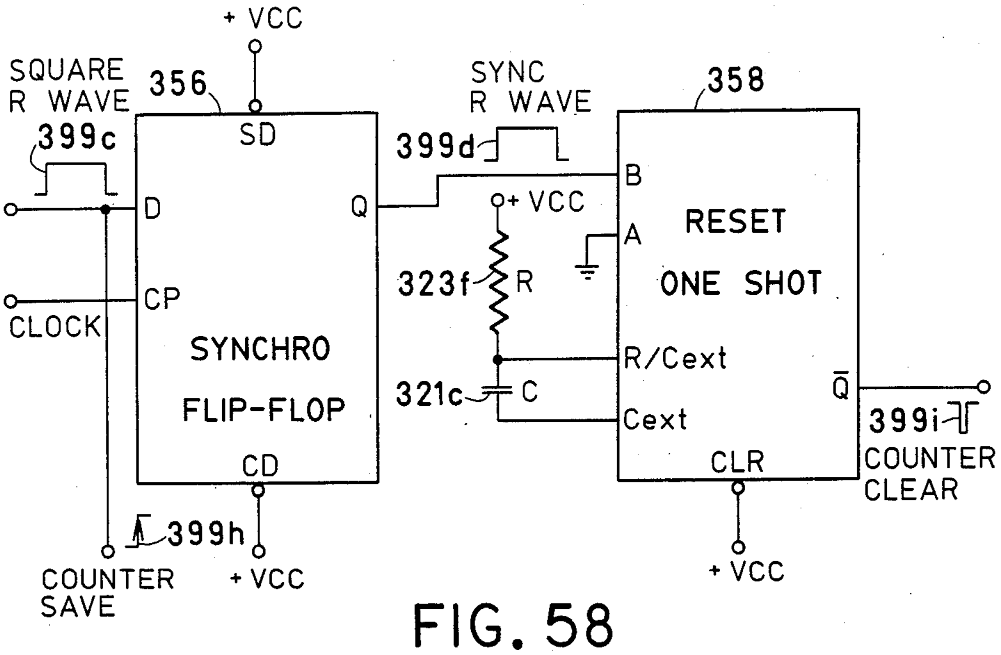
FIG. 58 is a detail of the counter control shown generally in FIGS. 53 and 54.

FIG. 58 is a detail of the counter control circuit, shown generally in FIGS. 53 and 54, for controlling the counter 345. The description of the circuit should be considered together with its associated timing diagram shown in FIG. 60. The R wave 398*b*, measured by the electrodes, is amplified by the amplifier 349 and converted to square R wave by the shaping circuit 341. The leading positive going edge of the SQUARE R WAVE 399*c* is used as COUNTER SAVE pulse 399*h*, to transfer the instant data in the counter 345, which represent the heart rate for previous R-R interval, to its internal register for storing it until new data are available. The SQUARE R WAVE 399*c* is applied to the D input of SYNCHRO flip-flop 356, to be synchronized with clock pulses 399*a*, and appears at its Q output as SYNC R WAVE 399*d*, to trigger, by its leading edge, RESET one shot multivibrator 358, which will produce at its output $\overline{Q}$ a negative going COUNTER CLEAR pulse 399*i* of short duration, determined by the values of resistor 323*a* and capacitor 321*c*, for resetting the counter 345 immediately after its contents were stored in its internal register.

Figure 59:
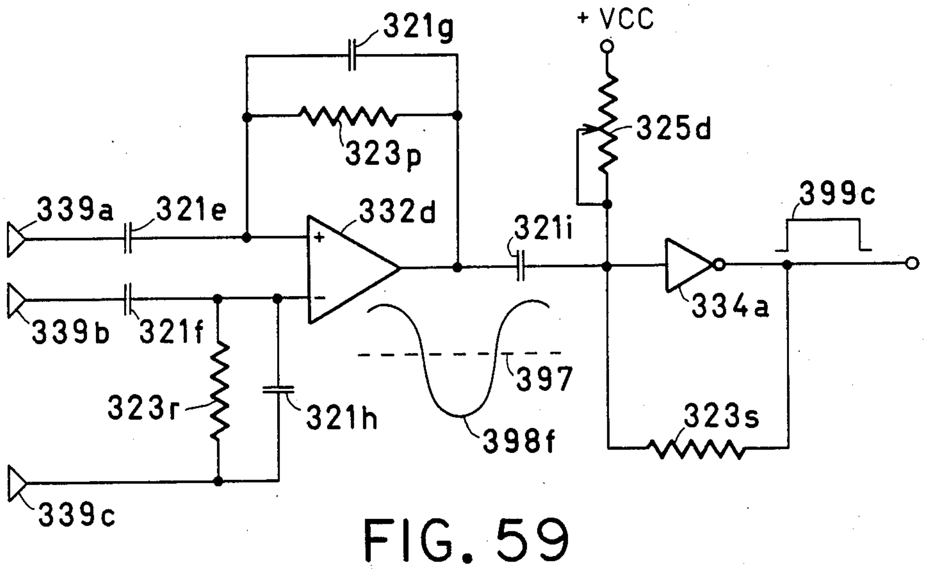
FIG. 59 is a schematic diagram of an amplifier and shaping circuit combination in the heart rate transducer circuit shown generally in FIGS. 53 and 54.

FIG. 59 is a detail of the amplifier and shaping circuit combination shown generally in FIGS. 53 and 54. Measuring electrodes 339*a*, 339*b*, and 339*c* are adapted to be attached to specific points of the body of the timepiece user for measuring electrical signals generated by functioning of a heart within the user's body. The electrode 339*c* is provided for suppression of common mode noise that may appear at the differential inputs from external electromagnetic fields. An amplifier 332*d* amplifies the measured signals from the range of milivolts to the range of volts, and provides at its output inverted R wave 398*f*, which is applied, via capacitor 321*i*, to the input of an inverter 334*a*. A potentiometer 325*d* provides adjustable bias voltage with respect to the ground potential, to allow a treshold 397 to be adjusted such that the inverted R wave 398*f* is converted into a square R wave 399*c* at the inverter's output.

Figure 60:
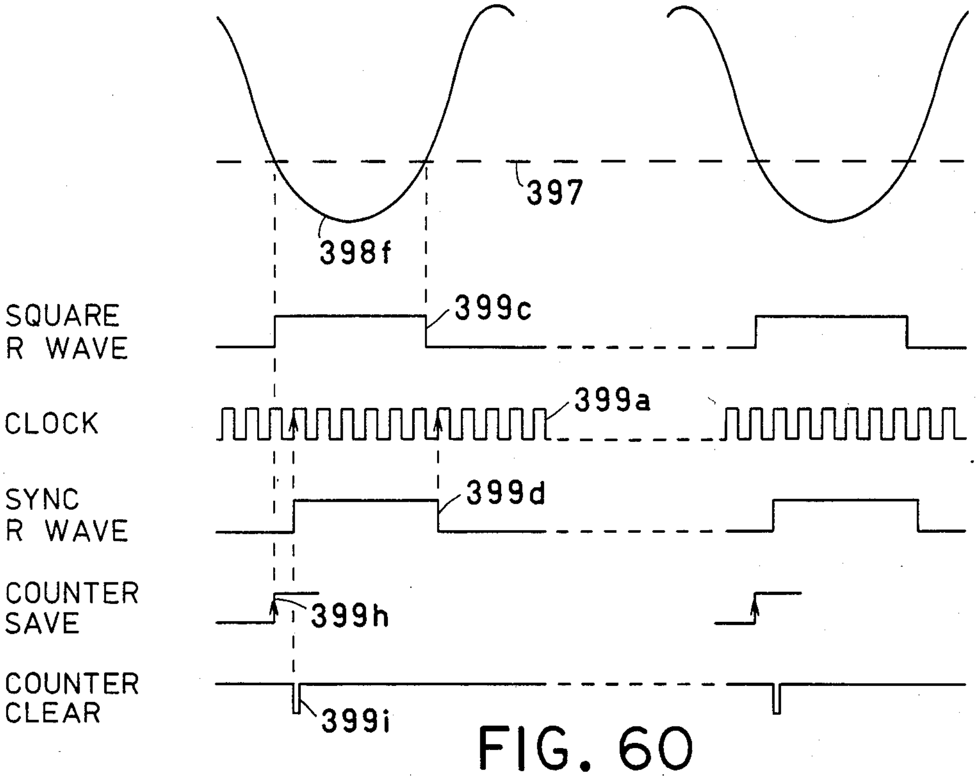
FIG. 60 is a timing diagram showing the relationship between the measured R wave and generated COUNTER SAVE and COUNTER CLEAR signals.

By referring now, more particularly, to the timing diagram shown in FIG. 60, the heart rate measuring method may be briefly summarized. Measured R wave is amplified and inverted, to obtain a wave 398*f*, and squared, to obtain a SQUARE R WAVE 399*c*. The interval between the adjacent R waves is measured by counting the number of stable clock pulses 399*a*. The leading edge of the SQUARE R WAVE 399*c* is used to generate the COUNTER SAVE pulse 399*h*, which is applied to the counter 345 to effect the transfer of its instant count, representing the distance between the previous R wave and the instant one, to the counter's internal register. The counter 345 is reset immediately after that, by the COUNTER CLEAR pulse 399*i*, which was generated in response to the leading edge of the SYNC R WAVE 399*d*, and starts accumulating clock pulses 399*a* again until the next R wave is detected, at which moment the total number of accumulated clock pulses is transferred to the counter's internal register, and the process is repeated. The heart rate may be calculated by dividing the number of clock pulses per minute by the number of clock pulses measured between the adjacent R waves.

Figure 61:
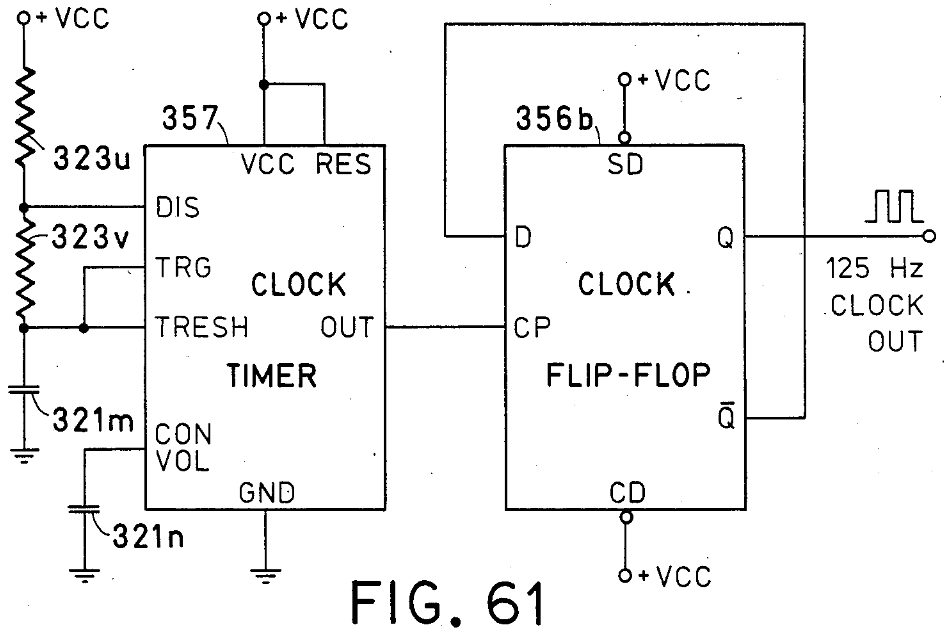
FIG. 61 is a schematic diagram of an oscillator shown generally in FIGS. 53 and 54.

FIG. 61 is a schematic diagram of the oscillator shown generally in FIGS. 53 and 54. A CLOCK TIMER 357 is used in its astable configuration to generate at its output OUT square wave pulses of a frequency 250 Hz, determined by the values of resistors 323*u*, 323*v* and capacitor 321*m*. The square wave pulses are applied to the Clock Pulse input CP of a CLOCK FLIP-FLOP 356*b* which will divide the frequency by two, to provide at its Q output clock pulses of 125 Hz frequency and of equal duty cycle which are used in the circuits for heart rate measurements. Alternately, it would be obvious that the clock pulses may be derived from the master clock which is used to generate the second, minute, and hour signals in the clock chip.

Figures 62, 63:
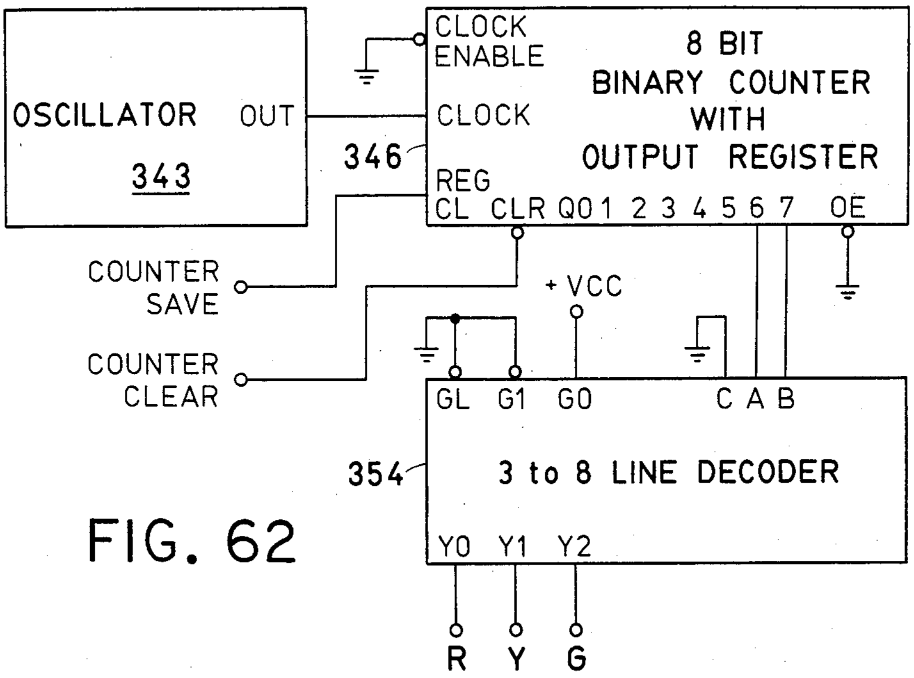
FIG. 62 is a detail of the counter and decoder combination shown generally in FIG. 53 for controlling the color of the display in three steps.
FIG. 63 is a chart showing the relationship between the recorded count of the counter shown in FIG. 62, calculated heart rate, and color of the display.

FIG. 62 is a detail of the counter and decoder combination, shown generally in FIG. 53, for generating color control signals to cause the display to illuminate in one of three possible colors in accordance with the accumulated count in the counter's internal register. The description of the circuit should be considered together with its associated chart shown in FIG. 63. The 8-bit binary counter 346 contains internal register with outputs Q0 to Q7 available. Two most significant outputs Q6 and Q7 are connected to respective inputs A and B of the 3-to-8 line decoder 354; the decoder's most significant input C is grounded. In response to the conditions of the counter outputs Q6 and Q7, the decoder 354 will develop output signals Y0, Y1, and Y2. It is readily apparent that the output Y0 will rise to a high logic level when both counter outputs Q6 and Q7 are at a low logic level (which is typical for counts less than 63), to generate active color control signal R (red). When the counter output Q6 rises to a high logic level, while the output Q7 is low (which is typical for counts between 64 and 127), the decoder output Y1 will rise to a high logic level to generate active color control signal Y (yellow). When the counter output Q7 rises to a high logic level and Q6 drops to a low logic level (which is typical for counts between 128 and 191), the decoder output Y2 will rise to a high logic level to generate active color control signal G (green). The values of the heart rate in the chart were calculated by dividing the number of clock pulses per minute (7500) by particular counts in the left column. The decoder outputs Y0 to Y2 may be connected as shown in FIG. 19.

Figures 64, 65:
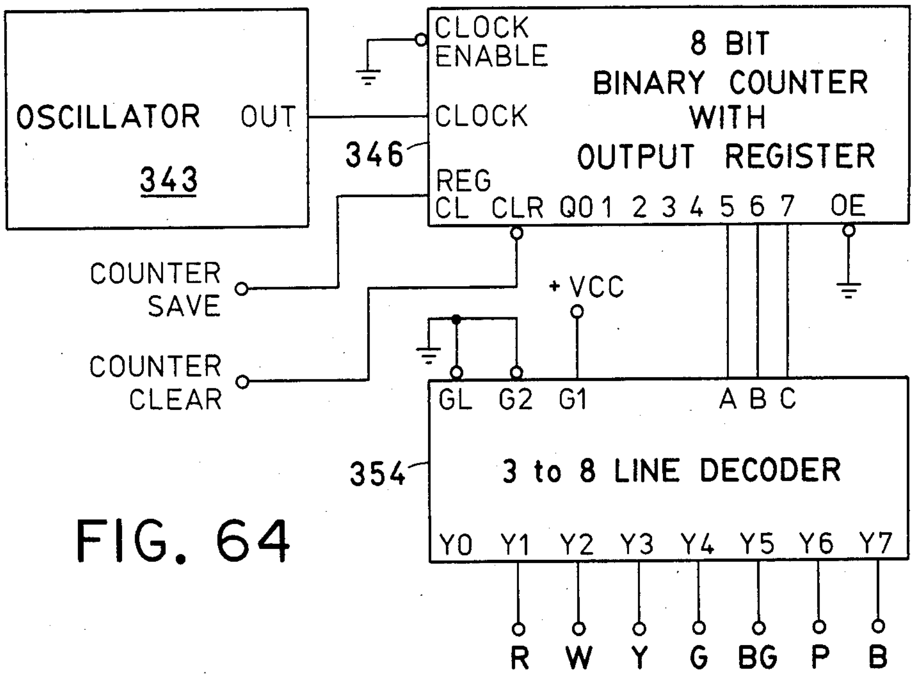
FIG. 64 is a detail of the counter and decoder combination shown generally in FIG. 53 for controlling the color of the display in seven steps.
FIG. 65 is a chart showing the relationship between the recorded count of the counter shown in FIG. 64, calculated heart rate, and color of the display.

FIG. 64 is a like detail of the counter and decoder combination for generating color control signals to cause the display to illuminate in one of seven possible colors, depending on the accumulated count in the counter's internal register. The associated chart is shown in FIG. 65. This circuit differs from the one shown in FIG. 62 in that three counter outputs Q5, Q6, and Q7 are connected to respective inputs A, B, and C of the decoder 354, to develop color control signals R, W, G, BG, P, and B at respective decoder outputs Y1 to Y7. When the counter output Q5 is at a high logic level and Q6, Q7 are at a low logic level (which is typical for counts between 32 and 63), the decoder output Y1 will rise to a high logic level to generate active color control signal R (red). The remaining color control signals are generated similarly. The decoder outputs Y1 to Y7 may be connected as shown in FIG. 20.

Although not shown in the drawings, it will be appreciated that the timepiece of this invention may have any conceivable form or shape, such as a wristwatch, pocket watch, clock, alarm clock, and the like. Alternately, the timepiece may have characteristics of an article for wearing on a body of wearer or for securing to wearer's clothing, such as a bracelet, ring, ear-ring, necklace, tie tack, button, cuff link, brooch, hair ornament, and the like, or it may be built into, or associated with, an object such as a pen, pencil, ruler, lighter, briefcase, purse, and the like.

In brief summary, the invention describes a method and a device for simultaneously displaying values of time and values of a physiological quantity, on a single variable color digital display device, by causing the values of time to be indicated in a digital format, and by controlling the color of the display in accordance with the values of the physiological quantity. In the most preferred embodiment, a timepiece with a variable color digital display was disclosed which can indicate time in digital format and in a color variable in accordance with the heart rate of its user.

All matter herein described and illustrated in the accompanying drawings should be interpreted as illustrative and not in a limiting sense. It would be obvious that numerous modifications can be made in the construction of the preferred embodiments shown herein, without departing from the spirit of the invention as defined in the appended claims. It is contemplated that the principles of the invention may be also applied to numerous diverse types of display devices, such are liquid crystal, plasma devices, and the like.

CORRELATION TABLE

This is a correlation table of reference characters used in the drawings herein, their descriptions, and examples of commercially available parts.

| # | DESCRIPTION | EXAMPLE |
|---|---|---|
| 1 | display segment | |
| 2 | red LED | |
| 3 | green LED | |
| 4 | blue LED | |
| 5 | red bus | |
| 6 | green bus | |
| 7 | blue bus | |
| 10 | device developing electric signals | |
| 11 | analog voltage source | |
| 12 | digital device | |
| 15 | segment body | |
| 16 | light scattering material | |
| 20 | decoder | |
| 21 | digital decoder driver | |
| 22 | 7-segment display decoder driver | |
| 23 | common cathode 7-segment decoder | 74LS49 |
| 24 | common anode 7-segment decoder | 74LS47 |
| 30 | monochromatic digital display | |
| 40 | variable color digital display | |
| 41 | multiplexed variable color display | |
| 42 | variable color 7-segment display (2 LEDs) | |
| 43 | variable color 7-segment display (3 LEDs) | |
| 44 | 4-digit variable color display (2 LEDs) | |
| 45 | 4-digit variable color display (3 LEDs) | |
| 46 | one variable color display character (2 LEDs) | |
| 47 | one variable color display character (3 LEDs) | |
| 50 | color control | |
| 51 | step variable color control | |
| 52 | color control (2 LEDs) | |
| 53 | color control (3 LEDs) | |
| 55 | color converter | |
| 56 | continuously variable color converter | |

-continued

CORRELATION TABLE

This is a correlation table of reference characters used in the drawings herein, their descriptions, and examples of commercially available parts.

| # | DESCRIPTION | EXAMPLE |
|---|---|---|
| 57 | 2-primary color converter | |
| 58 | 3-primary color converter | |
| 59 | single color converter | |
| 60 | 2-input OR gate | 74HC32 |
| 61 | 4-input OR gate | 4072 |
| 62 | non-inverting buffer | 74LS244 |
| 63 | inverting buffer | 74LS240 |
| 64 | inverter | part of 74LS240,4 |
| 65 | inverter | 74HC04 |
| 66 | 2-input AND gate | 74HC08 |
| 67 | priority encoder | 74HC147 |
| 68 | 3-to-8 line decoder | 74HC138 |
| 69 | logic circuit | |
| 70 | counter | |
| 71 | 8-bit counter | 74F579 |
| 72 | flip-flop | |
| 73 | D type flip-flop | 74HC74 |
| 74 | A/D converter | |
| 75 | 8-bit A/D converter | AD570 |
| 76 | memory | |
| 77 | 2k × 8 bit PROM | 2716 |
| 80 | scaling circuit | |
| 81 | op amp | LM741 |
| 82 | analog comparator | LM339 |
| 85 | signal converter | |
| 91 | resistor | |
| 92 | potentiometer | |
| 93 | capacitor | |
| 99 | pulse | |
| 301 | timekeeping device | |
| 302 | timekeeping device with multiplexed display | |
| 304 | Intersil stopwatch chip | ICM7045 |
| 310 | transducer | |
| 312 | Analog Devices temperature transducer | AD590J |
| 314 | SenSym atmospheric pressure transducer | LX1802AN |
| 321 | capacitor | |
| 323 | resistor | |
| 325 | potentiometer | |
| 329 | crystal | |
| 331 | op amp | LM741 |
| 332 | op amp | MC1776G |
| 334 | inverter | 74HC04 |
| 338 | electrode | |
| 339 | Beakman electrode | 650944 |
| 341 | shaping circuit | |
| 343 | oscillator | |
| 345 | counter | |
| 346 | 8-bit counter with register | 74HC590 |
| 347 | counter control | |
| 349 | amplifier | |
| 351 | color control latch | |
| 352 | counter latch | |
| 353 | decoder | |
| 354 | 3-to-8 line decoder | 74HC237 |
| 356 | D-type flip-flop | 74HC74 |
| 357 | timer | NE555 |
| 358 | one shot multivibrator | 74HC123 |
| 397 | treshold | |
| 398 | wave | |
| 399 | pulse | |

The examples of commercially available components should be considered as merely illustrative. It will be appreciated that other components may be readily and effectively used. The integrated circuits used in the description of the invention are manufactured by several well known companies, such are National Semiconductor Incorporated, Motorola Semiconductor Products Inc., Fairchild Camera and Instrument Corporation, Texas Instruments Incorporated, Intel Corporation, Analog Devices, Inc., Teledyne Semiconductor, Intersil, Inc., Precision Monolithics Incorporated, etc.

TABLE 1

| Input Voltage (Volts) | PROM Address (Hex) | DATA PORTIONS 'Red' PROM (Hex) | red | green |
|---|---|---|---|---|
| 0.0 | 00 | 00 | 0.0 | 1.0 |
| 0.039 | 01 | 00 | 0.0 | 1.0 |
| 0.078 | 02 | 00 | 0.0 | 1.0 |
| 0.117 | 03 | 00 | 0.0 | 1.0 |
| 0.156 | 04 | 00 | 0.0 | 1.0 |
| 0.195 | 05 | 00 | 0.0 | 1.0 |
| 0.234 | 06 | 00 | 0.0 | 1.0 |
| 0.273 | 07 | 00 | 0.0 | 1.0 |
| 0.312 | 08 | 00 | 0.0 | 1.0 |
| 0.352 | 09 | 00 | 0.0 | 1.0 |
| 0.391 | 0A | 00 | 0.0 | 1.0 |
| 0.430 | 0B | 00 | 0.0 | 1.0 |
| 0.469 | 0C | 00 | 0.0 | 1.0 |
| 0.508 | 0D | 00 | 0.0 | 1.0 |
| 0.547 | 0E | 00 | 0.0 | 1.0 |
| 0.586 | 0F | 00 | 0.0 | 1.0 |
| 0.625 | 10 | 40 | 0.25 | 0.75 |
| 0.664 | 11 | 40 | 0.25 | 0.75 |
| 0.703 | 12 | 40 | 0.25 | 0.75 |
| 0.742 | 13 | 40 | 0.25 | 0.75 |
| 0.781 | 14 | 40 | 0.25 | 0.75 |
| 0.820 | 15 | 40 | 0.25 | 0.75 |
| 0.859 | 16 | 40 | 0.25 | 0.75 |
| 0.898 | 17 | 40 | 0.25 | 0.75 |
| 0.937 | 18 | 40 | 0.25 | 0.75 |
| 0.977 | 19 | 40 | 0.25 | 0.75 |
| 1.016 | 1A | 40 | 0.25 | 0.75 |
| 1.055 | 1B | 40 | 0.25 | 0.75 |
| 1.094 | 1C | 40 | 0.25 | 0.75 |
| 1.133 | 1D | 40 | 0.25 | 0.75 |
| 1.172 | 1E | 40 | 0.25 | 0.75 |
| 1.211 | 1F | 40 | 0.25 | 0.75 |
| 1.250 | 20 | 80 | 0.5 | 0.5 |
| 1.289 | 21 | 80 | 0.5 | 0.5 |
| 1.328 | 22 | 80 | 0.5 | 0.5 |
| 1.367 | 23 | 80 | 0.5 | 0.5 |
| 1.406 | 24 | 80 | 0.5 | 0.5 |
| 1.445 | 25 | 80 | 0.5 | 0.5 |
| 1.484 | 26 | 80 | 0.5 | 0.5 |
| 1.523 | 27 | 80 | 0.5 | 0.5 |
| 1.562 | 28 | 80 | 0.5 | 0.5 |
| 1.602 | 29 | 80 | 0.5 | 0.5 |
| 1.641 | 2A | 80 | 0.5 | 0.5 |
| 1.680 | 2B | 80 | 0.5 | 0.5 |
| 1.719 | 2C | 80 | 0.5 | 0.5 |
| 1.758 | 2D | 80 | 0.5 | 0.5 |
| 1.797 | 2E | 80 | 0.5 | 0.5 |
| 1.836 | 2F | 80 | 0.5 | 0.5 |
| 1.875 | 30 | C0 | 0.75 | 0.25 |
| 1.914 | 31 | C0 | 0.75 | 0.25 |
| 1.953 | 32 | C0 | 0.75 | 0.25 |
| 1.992 | 33 | C0 | 0.75 | 0.25 |
| 2.031 | 34 | C0 | 0.75 | 0.25 |
| 2.070 | 35 | C0 | 0.75 | 0.25 |
| 2.109 | 36 | C0 | 0.75 | 0.25 |
| 2.148 | 37 | C0 | 0.75 | 0.25 |
| 2.187 | 38 | C0 | 0.75 | 0.25 |
| 2.227 | 39 | C0 | 0.75 | 0.25 |
| 2.266 | 3A | C0 | 0.75 | 0.25 |
| 2.305 | 3B | C0 | 0.75 | 0.25 |
| 2.344 | 3C | C0 | 0.75 | 0.25 |
| 2.389 | 3D | C0 | 0.75 | 0.25 |
| 2.422 | 3E | C0 | 0.75 | 0.25 |
| 2.461 | 3F | C0 | 0.75 | 0.25 |
| 2.500 | 40 | FF | 1.0 | 0.0 |
| 2.539 | 41 | FF | 1.0 | 0.0 |
| 2.578 | 42 | FF | 1.0 | 0.0 |
| 2.617 | 43 | FF | 1.0 | 0.0 |
| 2.656 | 44 | FF | 1.0 | 0.0 |
| 2.695 | 45 | FF | 1.0 | 0.0 |
| 2.734 | 46 | FF | 1.0 | 0.0 |
| 2.773 | 47 | FF | 1.0 | 0.0 |
| 2.812 | 48 | FF | 1.0 | 0.0 |
| 2.852 | 49 | FF | 1.0 | 0.0 |
| 2.891 | 4A | FF | 1.0 | 0.0 |
| 2.930 | 4B | FF | 1.0 | 0.0 |
| 2.969 | 4C | FF | 1.0 | 0.0 |
| 3.008 | 4D | FF | 1.0 | 0.0 |
| 3.047 | 4E | FF | 1.0 | 0.0 |
| 3.086 | 4F | FF | 1.0 | 0.0 |
| 3.125 | 50 | 00 | 0.0 | 1.0 |
| 3.164 | 51 | 00 | 0.0 | 1.0 |
| 3.203 | 52 | 00 | 0.0 | 1.0 |
| 3.242 | 53 | 00 | 0.0 | 1.0 |
| 3.281 | 54 | 00 | 0.0 | 1.0 |
| 3.320 | 55 | 00 | 0.0 | 1.0 |
| 3.359 | 56 | 00 | 0.0 | 1.0 |
| 3.398 | 57 | 00 | 0.0 | 1.0 |
| 3.437 | 58 | 00 | 0.0 | 1.0 |
| 3.477 | 59 | 00 | 0.0 | 1.0 |
| 3.516 | 5A | 00 | 0.0 | 1.0 |
| 3.555 | 5B | 00 | 0.0 | 1.0 |
| 3.594 | 5C | 00 | 0.0 | 1.0 |
| 3.633 | 5D | 00 | 0.0 | 1.0 |
| 3.672 | 5E | 00 | 0.0 | 1.0 |
| 3.711 | 5F | 00 | 0.0 | 1.0 |
| 3.750 | 60 | 40 | 0.25 | 0.75 |
| 3.789 | 61 | 40 | 0.25 | 0.75 |
| 3.828 | 62 | 40 | 0.25 | 0.75 |
| 3.867 | 63 | 40 | 0.25 | 0.75 |
| 3.906 | 64 | 40 | 0.25 | 0.75 |
| 3.945 | 65 | 40 | 0.25 | 0.75 |
| 3.984 | 66 | 40 | 0.25 | 0.75 |
| 4.023 | 67 | 40 | 0.25 | 0.75 |
| 4.062 | 68 | 40 | 0.25 | 0.75 |
| 4.102 | 69 | 40 | 0.25 | 0.75 |
| 4.141 | 6A | 40 | 0.25 | 0.75 |
| 4.178 | 6B | 40 | 0.25 | 0.75 |
| 4.219 | 6C | 40 | 0.25 | 0.75 |
| 4.258 | 6D | 40 | 0.25 | 0.75 |
| 4.299 | 6E | 40 | 0.25 | 0.75 |
| 4.336 | 6F | 40 | 0.25 | 0.75 |
| 4.375 | 70 | 80 | 0.5 | 0.5 |
| 4.414 | 71 | 80 | 0.5 | 0.5 |
| 4.453 | 72 | 80 | 0.5 | 0.5 |
| 4.492 | 73 | 80 | 0.5 | 0.5 |
| 4.531 | 74 | 80 | 0.5 | 0.5 |
| 4.570 | 75 | 80 | 0.5 | 0.5 |
| 4.609 | 76 | 80 | 0.5 | 0.5 |
| 4.648 | 77 | 80 | 0.5 | 0.5 |
| 4.687 | 78 | 80 | 0.5 | 0.5 |
| 4.727 | 79 | 80 | 0.5 | 0.5 |
| 4.766 | 7A | 80 | 0.5 | 0.5 |
| 4.805 | 7B | 80 | 0.5 | 0.5 |
| 4.844 | 7C | 80 | 0.5 | 0.5 |
| 4.883 | 7D | 80 | 0.5 | 0.5 |
| 4.922 | 7E | 80 | 0.5 | 0.5 |
| 4.961 | 7F | 80 | 0.5 | 0.5 |
| 5.000 | 80 | C0 | 0.75 | 0.25 |
| 5.039 | 81 | C0 | 0.75 | 0.25 |
| 5.078 | 82 | C0 | 0.75 | 0.25 |
| 5.117 | 83 | C0 | 0.75 | 0.25 |
| 5.156 | 84 | C0 | 0.75 | 0.25 |
| 5.195 | 85 | C0 | 0.75 | 0.25 |
| 5.234 | 86 | C0 | 0.75 | 0.25 |
| 5.273 | 87 | C0 | 0.75 | 0.25 |
| 5.312 | 88 | C0 | 0.75 | 0.25 |
| 5.352 | 89 | C0 | 0.75 | 0.25 |
| 5.391 | 8A | C0 | 0.75 | 0.25 |
| 5.430 | 8B | C0 | 0.75 | 0.25 |
| 5.469 | 8C | C0 | 0.75 | 0.25 |
| 5.508 | 8D | C0 | 0.75 | 0.25 |
| 5.547 | 8E | C0 | 0.75 | 0.25 |
| 5.586 | 8F | C0 | 0.75 | 0.25 |
| 5.625 | 90 | FF | 1.0 | 0.0 |
| 5.664 | 91 | FF | 1.0 | 0.0 |
| 5.703 | 92 | FF | 1.0 | 0.0 |
| 5.742 | 93 | FF | 1.0 | 0.0 |
| 5.781 | 94 | FF | 1.0 | 0.0 |
| 5.820 | 95 | FF | 1.0 | 0.0 |
| 5.859 | 96 | FF | 1.0 | 0.0 |
| 5.898 | 97 | FF | 1.0 | 0.0 |

TABLE 1-continued

| Input Voltage (Volts) | PROM Address (Hex) | DATA PORTIONS 'Red' PROM (Hex) | red | green |
|---|---|---|---|---|
| 5.937 | 98 | FF | 1.0 | 0.0 |
| 5.977 | 99 | FF | 1.0 | 0.0 |
| 6.016 | 9A | FF | 1.0 | 0.0 |
| 6.055 | 9B | FF | 1.0 | 0.0 |
| 6.094 | 9C | FF | 1.0 | 0.0 |
| 6.133 | 9D | FF | 1.0 | 0.0 |
| 6.172 | 9E | FF | 1.0 | 0.0 |
| 6.211 | 9F | FF | 1.0 | 0.0 |
| 6.250 | A0 | 00 | 0.0 | 1.0 |
| 6.289 | A1 | 00 | 0.0 | 1.0 |
| 6.328 | A2 | 00 | 0.0 | 1.0 |
| 6.367 | A3 | 00 | 0.0 | 1.0 |
| 6.406 | A4 | 00 | 0.0 | 1.0 |
| 6.445 | A5 | 00 | 0.0 | 1.0 |
| 6.484 | A6 | 00 | 0.0 | 1.0 |
| 6.524 | A7 | 00 | 0.0 | 1.0 |
| 6.562 | A8 | 00 | 0.0 | 1.0 |
| 6.602 | A9 | 00 | 0.0 | 1.0 |
| 6.641 | AA | 00 | 0.0 | 1.0 |
| 6.680 | AB | 00 | 0.0 | 1.0 |
| 6.719 | AC | 00 | 0.0 | 1.0 |
| 6.758 | AD | 00 | 0.0 | 1.0 |
| 6.797 | AE | 00 | 0.0 | 1.0 |
| 6.836 | AF | 00 | 0.0 | 1.0 |
| 6.875 | B0 | 40 | 0.25 | 0.75 |
| 6.914 | B1 | 40 | 0.25 | 0.75 |
| 6.953 | B2 | 40 | 0.25 | 0.75 |
| 6.992 | B3 | 40 | 0.25 | 0.75 |
| 7.031 | B4 | 40 | 0.25 | 0.75 |
| 7.070 | B5 | 40 | 0.25 | 0.75 |
| 7.109 | B6 | 40 | 0.25 | 0.75 |
| 7.148 | B7 | 40 | 0.25 | 0.75 |
| 7.187 | B8 | 40 | 0.25 | 0.75 |
| 7.227 | B9 | 40 | 0.25 | 0.75 |
| 7.266 | BA | 40 | 0.25 | 0.75 |
| 7.305 | BB | 40 | 0.25 | 0.75 |
| 7.344 | BC | 40 | 0.25 | 0.75 |
| 7.383 | BD | 40 | 0.25 | 0.75 |
| 7.422 | BE | 40 | 0.25 | 0.75 |
| 7.461 | BF | 40 | 0.25 | 0.75 |
| 7.500 | C0 | 80 | 0.5 | 0.5 |
| 7.539 | C1 | 80 | 0.5 | 0.5 |
| 7.587 | C2 | 80 | 0.5 | 0.5 |
| 7.617 | C3 | 80 | 0.5 | 0.5 |
| 7.656 | C4 | 80 | 0.5 | 0.5 |
| 7.695 | C5 | 80 | 0.5 | 0.5 |
| 7.734 | C6 | 80 | 0.5 | 0.5 |
| 7.773 | C7 | 80 | 0.5 | 0.5 |
| 7.812 | C8 | 80 | 0.5 | 0.5 |
| 7.852 | C9 | 80 | 0.5 | 0.5 |
| 7.891 | CA | 80 | 0.5 | 0.5 |
| 7.930 | CB | 80 | 0.5 | 0.5 |

TABLE 1-continued

| Input Voltage (Volts) | PROM Address (Hex) | DATA PORTIONS 'Red' PROM (Hex) | red | green |
|---|---|---|---|---|
| 7.969 | CC | 80 | 0.5 | 0.5 |
| 8.008 | CD | 80 | 0.5 | 0.5 |
| 8.047 | CE | 80 | 0.5 | 0.5 |
| 8.086 | CF | 80 | 0.5 | 0.5 |
| 8.125 | D0 | C0 | 0.75 | 0.25 |
| 8.164 | D1 | C0 | 0.75 | 0.25 |
| 8.203 | D2 | C0 | 0.75 | 0.25 |
| 8.242 | D3 | C0 | 0.75 | 0.25 |
| 8.281 | D4 | C0 | 0.75 | 0.25 |
| 8.320 | D5 | C0 | 0.75 | 0.25 |
| 8.359 | D6 | C0 | 0.75 | 0.25 |
| 8.398 | D7 | C0 | 0.75 | 0.25 |
| 8.437 | D8 | C0 | 0.75 | 0.25 |
| 8.477 | D9 | C0 | 0.75 | 0.25 |
| 8.516 | DA | C0 | 0.75 | 0.25 |
| 8.555 | DB | C0 | 0.75 | 0.25 |
| 8.594 | DC | C0 | 0.75 | 0.25 |
| 8.633 | DD | C0 | 0.75 | 0.25 |
| 8.672 | DE | C0 | 0.75 | 0.25 |
| 8.711 | DF | C0 | 0.75 | 0.25 |
| 8.750 | E0 | FF | 1.0 | 0.0 |
| 8.789 | E1 | FF | 1.0 | 0.0 |
| 8.828 | E2 | FF | 1.0 | 0.0 |
| 8.867 | E3 | FF | 1.0 | 0.0 |
| 8.906 | E4 | FF | 1.0 | 0.0 |
| 8.945 | E5 | FF | 1.0 | 0.0 |
| 8.984 | E6 | FF | 1.0 | 0.0 |
| 9.023 | E7 | FF | 1.0 | 0.0 |
| 9.062 | E8 | FF | 1.0 | 0.0 |
| 9.102 | E9 | FF | 1.0 | 0.0 |
| 9.141 | EA | FF | 1.0 | 0.0 |
| 9.180 | EB | FF | 1.0 | 0.0 |
| 9.219 | EC | FF | 1.0 | 0.0 |
| 9.258 | ED | FF | 1.0 | 0.0 |
| 9.299 | EE | FF | 1.0 | 0.0 |
| 9.336 | EF | FF | 1.0 | 0.0 |
| 9.375 | F0 | 00 | 0.0 | 1.0 |
| 9.414 | F1 | 00 | 0.0 | 1.0 |
| 9.453 | F2 | 00 | 0.0 | 1.0 |
| 9.492 | F3 | 00 | 0.0 | 1.0 |
| 9.531 | F4 | 00 | 0.0 | 1.0 |
| 9.570 | F5 | 00 | 0.0 | 1.0 |
| 9.609 | F6 | 00 | 0.0 | 1.0 |
| 9.648 | F7 | 00 | 0.0 | 1.0 |
| 9.687 | F8 | 00 | 0.0 | 1.0 |
| 9.727 | F9 | 00 | 0.0 | 1.0 |
| 9.766 | FA | 00 | 0.0 | 1.0 |
| 9.805 | FB | 00 | 0.0 | 1.0 |
| 9.844 | FC | 00 | 0.0 | 1.0 |
| 9.883 | FD | 00 | 0.0 | 1.0 |
| 9.922 | FE | 00 | 0.0 | 1.0 |
| 9.961 | FF | 00 | 0.0 | 1.0 |

TABLE 2

| Input Voltage (Volts) | PROM Address (Hex) | DATA PORTIONS 'Red' PROM (Hex) | 'Green' PROM (Hex) | 'Blue' PROM (Hex) | red | green | blue |
|---|---|---|---|---|---|---|---|
| 0.0 | 00 | FF | 00 | 00 | 1.0 | 0.0 | 0.0 |
| 0.039 | 01 | FE | 02 | 00 | 0.992 | 0.008 | 0.0 |
| 0.078 | 02 | FC | 04 | 00 | 0.984 | 0.016 | 0.0 |
| 0.117 | 03 | FA | 06 | 00 | 0.976 | 0.024 | 0.0 |
| 0.156 | 04 | F8 | 08 | 00 | 0.969 | 0.031 | 0.0 |
| 0.195 | 05 | F6 | 0A | 00 | 0.961 | 0.039 | 0.0 |
| 0.234 | 06 | F4 | 0C | 00 | 0.953 | 0.047 | 0.0 |
| 0.273 | 07 | F2 | 0E | 00 | 0.945 | 0.055 | 0.0 |
| 0.312 | 08 | F0 | 10 | 00 | 0.937 | 0.063 | 0.0 |
| 0.352 | 09 | EE | 12 | 00 | 0.930 | 0.070 | 0.0 |
| 0.391 | 0A | EC | 14 | 00 | 0.922 | 0.078 | 0.0 |
| 0.430 | 0B | EA | 16 | 00 | 0.914 | 0.086 | 0.0 |
| 0.469 | 0C | E8 | 18 | 00 | 0.906 | 0.094 | 0.0 |
| 0.508 | 0D | E6 | 1A | 00 | 0.899 | 0.101 | 0.0 |
| 0.547 | 0E | E4 | 1C | 00 | 0.891 | 0.109 | 0.0 |
| 0.586 | 0F | E2 | 1E | 00 | 0.883 | 0.117 | 0.0 |
| 0.625 | 10 | E0 | 20 | 00 | 0.875 | 0.125 | 0.0 |

TABLE 2-continued

| Input Voltage (Volts) | PROM Address (Hex) | DATA PORTIONS 'Red' PROM (Hex) | 'Green' PROM (Hex) | 'Blue' PROM (Hex) | red | green | blue |
|---|---|---|---|---|---|---|---|
| 0.664 | 11 | DE | 22 | 00 | 0.867 | 0.133 | 0.0 |
| 0.703 | 12 | DC | 24 | 00 | 0.859 | 0.141 | 0.0 |
| 0.742 | 13 | DA | 26 | 00 | 0.851 | 0.149 | 0.0 |
| 0.781 | 14 | D8 | 28 | 00 | 0.844 | 0.156 | 0.0 |
| 0.820 | 15 | D6 | 2A | 00 | 0.836 | 0.164 | 0.0 |
| 0.859 | 16 | D4 | 2C | 00 | 0.828 | 0.172 | 0.0 |
| 0.898 | 17 | D2 | 2E | 00 | 0.820 | 0.180 | 0.0 |
| 0.937 | 18 | D0 | 30 | 00 | 0.812 | 0.188 | 0.0 |
| 0.977 | 19 | CE | 32 | 00 | 0.804 | 0.196 | 0.0 |
| 1.016 | 1A | CC | 34 | 00 | 0.796 | 0.204 | 0.0 |
| 1.055 | 1B | CA | 36 | 00 | 0.788 | 0.212 | 0.0 |
| 1.094 | 1C | C8 | 38 | 00 | 0.781 | 0.219 | 0.0 |
| 1.133 | 1D | C6 | 3A | 00 | 0.773 | 0.227 | 0.0 |
| 1.172 | 1E | C4 | 3C | 00 | 0.766 | 0.234 | 0.0 |
| 1.211 | 1F | C2 | 3E | 00 | 0.758 | 0.242 | 0.0 |
| 1.250 | 20 | C0 | 40 | 00 | 0.75 | 0.25 | 0.0 |
| 1.289 | 21 | BE | 42 | 00 | 0.742 | 0.258 | 0.0 |
| 1.328 | 22 | BC | 44 | 00 | 0.734 | 0.266 | 0.0 |
| 1.367 | 23 | BA | 46 | 00 | 0.726 | 0.274 | 0.0 |
| 1.406 | 24 | B8 | 48 | 00 | 0.719 | 0.281 | 0.0 |
| 1.445 | 25 | B6 | 4A | 00 | 0.711 | 0.289 | 0.0 |
| 1.484 | 26 | B4 | 4C | 00 | 0.703 | 0.297 | 0.0 |
| 1.523 | 27 | B2 | 4E | 00 | 0.695 | 0.305 | 0.0 |
| 1.562 | 28 | B0 | 50 | 00 | 0.687 | 0.313 | 0.0 |
| 1.602 | 29 | AE | 52 | 00 | 0.680 | 0.320 | 0.0 |
| 1.641 | 2A | AC | 54 | 00 | 0.672 | 0.328 | 0.0 |
| 1.680 | 2B | AA | 56 | 00 | 0.664 | 0.336 | 0.0 |
| 1.719 | 2C | A8 | 58 | 00 | 0.656 | 0.344 | 0.0 |
| 1.758 | 2D | A6 | 5A | 00 | 0.648 | 0.352 | 0.0 |
| 1.797 | 2E | A4 | 5C | 00 | 0.641 | 0.359 | 0.0 |
| 1.836 | 2F | A2 | 5E | 00 | 0.633 | 0.367 | 0.0 |
| 1.875 | 30 | A0 | 60 | 00 | 0.625 | 0.375 | 0.0 |
| 1.914 | 31 | 9E | 62 | 00 | 0.613 | 0.383 | 0.0 |
| 1.953 | 32 | 9C | 64 | 00 | 0.609 | 0.391 | 0.0 |
| 1.992 | 33 | 9A | 66 | 00 | 0.602 | 0.398 | 0.0 |
| 2.031 | 34 | 98 | 68 | 00 | 0.594 | 0.406 | 0.0 |
| 2.070 | 35 | 96 | 6A | 00 | 0.586 | 0.414 | 0.0 |
| 2.109 | 36 | 94 | 6C | 00 | 0.578 | 0.422 | 0.0 |
| 2.148 | 37 | 92 | 6E | 00 | 0.570 | 0.430 | 0.0 |
| 2.187 | 38 | 90 | 70 | 00 | 0.562 | 0.438 | 0.0 |
| 2.227 | 39 | 8E | 72 | 00 | 0.554 | 0.446 | 0.0 |
| 2.266 | 3A | 8C | 74 | 00 | 0.547 | 0.453 | 0.0 |
| 2.305 | 3B | 8A | 76 | 00 | 0.539 | 0.461 | 0.0 |
| 2.344 | 3C | 88 | 78 | 00 | 0.531 | 0.469 | 0.0 |
| 2.389 | 3D | 86 | 7A | 00 | 0.524 | 0.476 | 0.0 |
| 2.422 | 3E | 84 | 7C | 00 | 0.516 | 0.484 | 0.0 |
| 2.461 | 3F | 82 | 7E | 00 | 0.508 | 0.492 | 0.0 |
| 2.500 | 40 | 80 | 80 | 00 | 0.5 | 0.5 | 0.0 |
| 2.539 | 41 | 7C | 84 | 00 | 0.484 | 0.516 | 0.0 |
| 2.578 | 42 | 78 | 88 | 00 | 0.469 | 0.531 | 0.0 |
| 2.617 | 43 | 74 | 8C | 00 | 0.453 | 0.547 | 0.0 |
| 2.656 | 44 | 70 | 90 | 00 | 0.437 | 0.563 | 0.0 |
| 2.695 | 45 | 6C | 94 | 00 | 0.422 | 0.578 | 0.0 |
| 2.734 | 46 | 68 | 98 | 00 | 0.406 | 0.594 | 0.0 |
| 2.773 | 47 | 64 | 9C | 00 | 0.391 | 0.609 | 0.0 |
| 2.812 | 48 | 60 | A0 | 00 | 0.375 | 0.625 | 0.0 |
| 2.852 | 49 | 5C | A4 | 00 | 0.359 | 0.641 | 0.0 |
| 2.891 | 4A | 58 | A8 | 00 | 0.344 | 0.656 | 0.0 |
| 2.930 | 4B | 54 | AC | 00 | 0.328 | 0.672 | 0.0 |
| 2.969 | 4C | 50 | B0 | 00 | 0.312 | 0.688 | 0.0 |
| 3.008 | 4D | 4C | B4 | 00 | 0.297 | 0.703 | 0.0 |
| 3.047 | 4E | 48 | B8 | 00 | 0.281 | 0.719 | 0.0 |
| 3.086 | 4F | 44 | BC | 00 | 0.266 | 0.734 | 0.0 |
| 3.125 | 50 | 40 | C0 | 00 | 0.25 | 0.75 | 0.0 |
| 3.164 | 51 | 3C | C4 | 00 | 0.234 | 0.766 | 0.0 |
| 3.203 | 52 | 38 | C8 | 00 | 0.219 | 0.781 | 0.0 |
| 3.242 | 53 | 34 | CC | 00 | 0.203 | 0.797 | 0.0 |
| 3.281 | 54 | 30 | D0 | 00 | 0.187 | 0.813 | 0.0 |
| 3.320 | 55 | 2C | D4 | 00 | 0.172 | 0.828 | 0.0 |
| 3.359 | 56 | 28 | D8 | 00 | 0.156 | 0.844 | 0.0 |
| 3.398 | 57 | 24 | DC | 00 | 0.141 | 0.859 | 0.0 |
| 3.437 | 58 | 20 | E0 | 00 | 0.125 | 0.875 | 0.0 |
| 3.477 | 59 | 1C | E4 | 00 | 0.109 | 0.891 | 0.0 |
| 3.516 | 5A | 18 | E8 | 00 | 0.094 | 0.906 | 0.0 |
| 3.555 | 5B | 14 | EC | 00 | 0.078 | 0.922 | 0.0 |
| 3.594 | 5C | 10 | F0 | 00 | 0.062 | 0.938 | 0.0 |
| 3.633 | 5D | 0C | F4 | 00 | 0.047 | 0.953 | 0.0 |
| 3.672 | 5E | 08 | F8 | 00 | 0.031 | 0.967 | 0.0 |

TABLE 2-continued

| Input Voltage (Volts) | PROM Address (Hex) | DATA PORTIONS 'Red' PROM (Hex) | 'Green' PROM (Hex) | 'Blue' PROM (Hex) | red | green | blue |
|---|---|---|---|---|---|---|---|
| 3.711 | 5F | 04 | FC | 00 | 0.016 | 0.984 | 0.0 |
| 3.750 | 60 | 00 | FF | 00 | 0.0 | 1.0 | 0.0 |
| 3.789 | 61 | 00 | F8 | 08 | 0.0 | 0.969 | 0.031 |
| 3.828 | 62 | 00 | F0 | 10 | 0.0 | 0.937 | 0.063 |
| 3.867 | 63 | 00 | E8 | 18 | 0.0 | 0.906 | 0.094 |
| 3.906 | 64 | 00 | E0 | 20 | 0.0 | 0.875 | 0.125 |
| 3.945 | 65 | 00 | D8 | 28 | 0.0 | 0.844 | 0.156 |
| 3.984 | 66 | 00 | D0 | 30 | 0.0 | 0.812 | 0.188 |
| 4.023 | 67 | 00 | C8 | 38 | 0.0 | 0.781 | 0.219 |
| 4.062 | 68 | 00 | C0 | 40 | 0.0 | 0.75 | 0.25 |
| 4.102 | 69 | 00 | B8 | 48 | 0.0 | 0.719 | 0.281 |
| 4.141 | 6A | 00 | B0 | 50 | 0.0 | 0.687 | 0.313 |
| 4.178 | 6B | 00 | A8 | 58 | 0.0 | 0.656 | 0.344 |
| 4.219 | 6C | 00 | A0 | 60 | 0.0 | 0.625 | 0.375 |
| 4.258 | 6D | 00 | 98 | 68 | 0.0 | 0.594 | 0.406 |
| 4.299 | 6E | 00 | 90 | 70 | 0.0 | 0.562 | 0.438 |
| 4.336 | 6F | 00 | 88 | 78 | 0.0 | 0.531 | 0.469 |
| 4.375 | 70 | 00 | 80 | 80 | 0.0 | 0.5 | 0.5 |
| 4.414 | 71 | 00 | 78 | 88 | 0.0 | 0.469 | 0.531 |
| 4.453 | 72 | 00 | 70 | 90 | 0.0 | 0.437 | 0.563 |
| 4.492 | 73 | 00 | 68 | 98 | 0.0 | 0.406 | 0.594 |
| 4.531 | 74 | 00 | 60 | A0 | 0.0 | 0.375 | 0.625 |
| 4.570 | 75 | 00 | 58 | A8 | 0.0 | 0.344 | 0.656 |
| 4.609 | 76 | 00 | 50 | B0 | 0.0 | 0.312 | 0.688 |
| 4.648 | 77 | 00 | 48 | B8 | 0.0 | 0.281 | 0.719 |
| 4.687 | 78 | 00 | 40 | C0 | 0.0 | 0.25 | 0.75 |
| 4.727 | 79 | 00 | 38 | C8 | 0.0 | 0.219 | 0.781 |
| 4.766 | 7A | 00 | 30 | D0 | 0.0 | 0.187 | 0.813 |
| 4.805 | 7B | 00 | 28 | D8 | 0.0 | 0.156 | 0.844 |
| 4.844 | 7C | 00 | 20 | E0 | 0.0 | 0.125 | 0.875 |
| 4.883 | 7D | 00 | 18 | E8 | 0.0 | 0.094 | 0.906 |
| 4.922 | 7E | 00 | 10 | FO | 0.0 | 0.062 | 0.938 |
| 4.961 | 7F | 00 | 08 | F8 | 0.0 | 0.031 | 0.967 |
| 5.000 | 80 | 00 | 00 | FF | 0.0 | 0.0 | 1.0 |
| 5.039 | 81 | 04 | 00 | FC | 0.016 | 0.0 | 0.984 |
| 5.078 | 82 | 08 | 00 | F8 | 0.031 | 0.0 | 0.969 |
| 5.117 | 83 | 0C | 00 | F4 | 0.047 | 0.0 | 0.953 |
| 5.156 | 84 | 10 | 00 | F0 | 0.063 | 0.0 | 0.937 |
| 5.195 | 85 | 14 | 00 | EC | 0.078 | 0.0 | 0.922 |
| 5.234 | 86 | 18 | 00 | E8 | 0.094 | 0.0 | 0.906 |
| 5.273 | 87 | 1C | 00 | E4 | 0.109 | 0.0 | 0.891 |
| 5.312 | 88 | 20 | 00 | E0 | 0.125 | 0.0 | 0.875 |
| 5.352 | 89 | 24 | 00 | DC | 0.141 | 0.0 | 0.859 |
| 5.391 | 8A | 28 | 00 | D8 | 0.156 | 0.0 | 0.844 |
| 5.430 | 8B | 2C | 00 | D4 | 0.172 | 0.0 | 0.828 |
| 5.469 | 8C | 30 | 00 | D0 | 0.188 | 0.0 | 0.812 |
| 5.508 | 8D | 34 | 00 | CC | 0.2 | 0.0 | 0.8 |
| 5.547 | 8E | 38 | 00 | C8 | 0.219 | 0.0 | 0.781 |
| 5.586 | 8F | 3C | 00 | C4 | 0.234 | 0.0 | 0.766 |
| 5.625 | 90 | 40 | 00 | C0 | 0.25 | 0.0 | 0.75 |
| 5.664 | 91 | 44 | 00 | BC | 0.266 | 0.0 | 0.734 |
| 5.703 | 92 | 48 | 00 | B8 | 0.281 | 0.0 | 0.719 |
| 5.742 | 93 | 4C | 00 | B4 | 0.297 | 0.0 | 0.703 |
| 5.781 | 94 | 50 | 00 | B0 | 0.313 | 0.0 | 0.687 |
| 5.820 | 95 | 54 | 00 | AC | 0.328 | 0.0 | 0.672 |
| 5.859 | 96 | 58 | 00 | A8 | 0.344 | 0.0 | 0.656 |
| 5.898 | 97 | 5C | 00 | A4 | 0.359 | 0.0 | 0.641 |
| 5.937 | 98 | 60 | 00 | AO | 0.375 | 0.0 | 0.625 |
| 5.977 | 99 | 64 | 00 | 9C | 0.391 | 0.0 | 0.609 |
| 6.016 | 9A | 68 | 00 | 98 | 0.406 | 0.0 | 0.594 |
| 6.055 | 9B | 6C | 00 | 94 | 0.422 | 0.0 | 0.578 |
| 6.094 | 9C | 70 | 00 | 90 | 0.438 | 0.0 | 0.562 |
| 6.133 | 9D | 74 | 00 | 8C | 0.453 | 0.0 | 0.547 |
| 6.172 | 9E | 78 | 00 | 88 | 0.469 | 0.0 | 0.531 |
| 6.211 | 9F | 7C | 00 | 84 | 0.484 | 0.0 | 0.516 |
| 6.250 | A0 | 80 | 00 | 80 | 0.5 | 0.0 | 0.5 |
| 6.289 | A1 | 84 | 00 | 7C | 0.516 | 0.0 | 0.484 |
| 6.328 | A2 | 88 | 00 | 78 | 0.531 | 0.0 | 0.469 |
| 6.367 | A3 | 8C | 00 | 74 | 0.547 | 0.0 | 0.453 |
| 6.406 | A4 | 90 | 00 | 70 | 0.563 | 0.0 | 0.437 |
| 6.445 | A5 | 94 | 00 | 6C | 0.578 | 0.0 | 0.422 |
| 6.484 | A6 | 98 | 00 | 68 | 0.594 | 0.0 | 0.406 |
| 6.524 | A7 | 9C | 00 | 64 | 0.609 | 0.0 | 0.391 |
| 6.562 | A8 | A0 | 00 | 60 | 0.625 | 0.0 | 0.375 |
| 6.602 | A9 | A4 | 00 | 5C | 0.641 | 0.0 | 0.359 |
| 6.641 | AA | A8 | 00 | 58 | 0.656 | 0.0 | 0.344 |
| 6.680 | AB | AC | 00 | 54 | 0.672 | 0.0 | 0.328 |
| 6.719 | AC | B0 | 00 | 50 | 0.688 | 0.0 | 0.312 |

TABLE 2-continued

| Input Voltage (Volts) | PROM Address (Hex) | DATA PORTIONS 'Red' PROM (Hex) | 'Green' PROM (Hex) | 'Blue' PROM (Hex) | red | green | blue |
|---|---|---|---|---|---|---|---|
| 6.758 | AD | B4 | 00 | 4C | 0.703 | 0.0 | 0.297 |
| 6.797 | AE | B8 | 00 | 48 | 0.719 | 0.0 | 0.281 |
| 6.836 | AF | BC | 00 | 44 | 0.734 | 0.0 | 0.266 |
| 6.875 | B0 | C0 | 00 | 40 | 0.75 | 0.0 | 0.25 |
| 6.914 | B1 | C4 | 00 | 3C | 0.766 | 0.0 | 0.234 |
| 6.953 | B2 | C8 | 00 | 38 | 0.781 | 0.0 | 0.219 |
| 6.992 | B3 | CC | 00 | 34 | 0.797 | 0.0 | 0.203 |
| 7.031 | B4 | D0 | 00 | 30 | 0.813 | 0.0 | 0.187 |
| 7.070 | B5 | D4 | 00 | 2C | 0.828 | 0.0 | 0.172 |
| 7.109 | B6 | D8 | 00 | 28 | 0.844 | 0.0 | 0.156 |
| 7.148 | B7 | DC | 00 | 24 | 0.859 | 0.0 | 0.141 |
| 7.187 | B8 | E0 | 00 | 20 | 0.875 | 0.0 | 0.125 |
| 7.227 | B9 | E4 | 00 | 1C | 0.891 | 0.0 | 0.109 |
| 7.266 | BA | E8 | 00 | 18 | 0.906 | 0.0 | 0.094 |
| 7.305 | BB | EC | 00 | 14 | 0.922 | 0.0 | 0.078 |
| 7.344 | BC | F0 | 00 | 10 | 0.938 | 0.0 | 0.062 |
| 7.383 | BD | F4 | 00 | 0C | 0.953 | 0.0 | 0.047 |
| 7.422 | BE | F8 | 00 | 08 | 0.967 | 0.0 | 0.031 |
| 7.461 | BF | FC | 00 | 04 | 0.984 | 0.0 | 0.016 |

What I claim is:

1. The method of simultaneously indicating values of time and values of a physiological quantity, on a single variable color digital display means, by causing said values of time to be indicated on said variable color digital display means in a digital format, and by controlling the color of said variable color digital display means in accordance with said values of said physiological quantity.

2. The method as defined in the claim 1 wherein the color of said variable color digital display means may be controlled substantially continuously such that its color changes are proportional to changes in said values of said physiological quantity.

3. The method as defined in the claim 1 wherein the color of said variable color digital display means may be controlled in a plurality of steps.

4. A timepiece comprising:

timekeeping means;

variable color digital display means for indicating time in a digital format;

physiological transducer means for measuring a physiological quantity and for developing output electrical signals related to said physiological quantity; and color control means responsive to said output electrical signals of said physiological transducer means for controlling the color of said variable color digital display means in accordance with said measured physiological quantity.

5. A timepiece as defined in the claim 4 more characterized by:

said color control means controlling the color of said variable color digital display means substantially continuously such that its color changes are proportional to changes in said measured physiological quantity.

6. A timepiece as defined in the claim 4 more characterized by:

said color control means controlling the color of said variable color digital display means in a plurality of steps.

7. A timepiece comprising:

timekeeping means;

variable color digital display means for indicating time in a digital format;

heart rate transducer means for measuring heart rate of a user of said timepiece and for developing output electrical signals related to the functioning of a heart beating within the user's body; and color control means responsive to said output electrical signals of said heart rate transducer means for controlling the color of said variable color digital display means in accordance with functioning of said heart beating.

8. A timepiece as defined in the claim 7 more characterized by:

said color control means controlling the color of said variable color digital display means substantially continuously such that its color changes are proportional to changes in the functioning of said heart beating.

9. A timepiece as defined in the claim 7 more characterized by:

said heart rate transducer means including comparison means for effecting a comparison of the measured value of the heart rate with a plurality of respectively different predetermined limits to determine the range in which the measured value of the heart rate lies, and for developing comparison signals accordingly;

said color control means being responsive to said comparison signals for controlling the color of said variable color digital display means in a plurality of steps such that its color corresponds to the range in which said measured value of the heart rate lies.

10. A timepiece as defined in the claim 7 more characterized by:

said heart rate transducer means including comparison means for effecting a comparison of the measured value of the heart rate with a low and high predetermined limits to determine whether said measured value of the heart rate is lower than said low predetermined limit, or higher than said high predetermined limit, or within the bounds of said low and high predetermined limits, and for developing comparison signals accordingly;

said color control means being responsive to said comparison signals for illuminating said variable color digital display means in a first color when said measured value of the heart rate is lower than said low predetermined limit, in a second color when said measured value of the heart rate is higher than said high predetermined limit, and in a third color when said measured value of the heart rate is within the bounds of said low and high predetermined limits, said first, second, and third colors being respectively different.

11. A timepiece as defined in the claim 7 more characterized by:

said heart rate transducer means including comparison means for effecting a comparison of the measured value of the heart rate with six progressively increasing predetermined limits, defining seven ranges, to determine in which one of said seven ranges said measured value of the heart rate lies, and for developing comparison signals accordingly;

said color control means being responsive to said comparison signals for illuminating said variable color digital display means in one of seven respectively different colors according to the range in which said measured value of the heart rate lies.

* * * * *